US006900016B1

(12) United States Patent
Venter et al.

(10) Patent No.: US 6,900,016 B1
(45) Date of Patent: May 31, 2005

(54) POLYMORPHISMS IN KNOWN GENES ASSOCIATED WITH INFLAMMATORY AUTOIMMUNE DISEASE, METHODS OF DETECTION AND USES THEREOF

(75) Inventors: J. Craig Venter, Rockville, MD (US); Jinghui N. Zhang, Rockville, MD (US); Xiangjun Liu, Olney, MD (US); William Rowe, Rockville, MD (US); Anibal Cravchik, Gaithersburg, MD (US); Francis Kalush, Rockville, MD (US); Ashwinikumar Naik, Gaithersburg, MD (US); Gangadharan Subramanian, Columbia, MD (US); Trevor Woodage, Washington, DC (US)

(73) Assignee: Applera Corporation, Norwalk, CT (US)

( * ) Notice: Subject to any disclaimer, the term of this patent is extended or adjusted under 35 U.S.C. 154(b) by 312 days.

(21) Appl. No.: 09/949,002

(22) Filed: Sep. 10, 2001

Related U.S. Application Data

(60) Provisional application No. 60/231,401, filed on Sep. 8, 2000.

(51) Int. Cl.$^7$ .......................... C12Q 1/68; C12P 19/34; C07K 13/00; C07H 21/04
(52) U.S. Cl. ...................... 435/6; 435/91.2; 435/320.1; 530/350; 536/23.4
(58) Field of Search ....................... 435/6, 91.2, 320.1; 530/350; 536/23.4

(56) References Cited

PUBLICATIONS

Genebank entry for gi: 15718696 (NM_001227).
Genebank entry for gi: 4502581 (NM_001218).
OMIM entry for Caspase 7 (omim No. 601761).

Primary Examiner—Kenneth R. Horlick
Assistant Examiner—Joyce Tung
(74) Attorney, Agent, or Firm—Celera Genomics; Justin D. Karjala

(57) ABSTRACT

The present invention is based on the discovery of novel polymorphisms (SNPs) in the genes known in the art to contribute to inflammatory and autoimmune disorders. Such polymorphisms can lead to a variety of disorders that are mediated/modulated by a variant inflammatory and autoimmune disorders associated protein. The present invention provides reagents used for detecting and expressing the variant nucleic acid/protein sequence as well as methods of identifying and using these variants.

20 Claims, 1 Drawing Sheet

POLYMORPHISMS IN KNOWN GENES ASSOCIATED WITH INFLAMMATORY AUTOIMMUNE DISEASE, METHODS OF DETECTION AND USES THEREOF

This application claims benefit of 60/231,401 filed Sep. 08, 2000.

FIELD OF THE INVENTION

The present invention is in the field of inflammatory and autoimmune disorders diagnosis and therapy. The present invention specifically provides previously unknown single nucleotide polymorphisms (SNPs) in genes that have been identified as being involved in pathologies associated with inflammatory and autoimmune disorders. Since these genes are known to be associated with inflammatory and autoimmune disorders, the presently disclosed naturally occurring polymorphisms (variants) are valuable for association and linkage analysis. Specifically, the identified SNPs are useful for such applications as screening for inflammatory and autoimmune disorders susceptibility, prevention of inflammatory and autoimmune disorders, development of diagnostics and therapies for inflammatory and autoimmune disorders, development of drugs for inflammatory and autoimmune disorders, and development of individualized drug treatments based on an individual's SNP profile. The SNPs provided by the present invention are also useful for human identification. Methods and reagents for detecting the presence of these polymorphisms are provided.

BACKGROUND OF THE INVENTION

Inflammatory and Autoimmune Diseases

Autoimmune diseases are characterized by the body's immune responses being directed against its own tissues, resulting in inflammation and destruction. A wide range of degenerative diseases are caused as a result. For example, immune dysfunction can cause immune responsive cells to attack the linings of the joints, resulting in rheumatoid arthritis, or prompt defectively functioning immune cells to attack the insulin-producing islet cells of the pancreas, resulting in insulin-dependent diabetes.

There is a whole class of degenerative diseases that are caused by changes in the immune system that result in the immune system attacking normal cells in the body. Any disease is considered autoimmune if antibodies or cytotoxic cells are directed against self-antigens in the body's own tissues. Diseases such as lupus erythematosus, autoimmune hepatitis, diabetes, pancreatitis, and rheumatoid arthritis can develop and become dangerous diseases requiring drastic measures to control and correct. Allergy is also the result of disordered immune function. Additionally, there are other diseases that may be the result of autoimmune dysfunction, such as multiple sclerosis.

Studies in both humans and in animal models of specific disorders suggest that polymorphisms of multiple genes are involved in conferring either a predisposition to or protection from autoimmune diseases. Genes encoding polymorphic proteins that regulate immune responses or the rates and extent of metabolism of certain chemical structures have been the focus of much of the research regarding genetic susceptibility. Twin studies of rheumatoid arthritis (RA), systemic lupus erythematosus (SLE), type I diabetes, and multiple sclerosis (MS) indicate that disease concordance in monozygotic twins is 4 or more times higher than in dizygotic twins. Strong familial associations (odds ratio ranging from 5–10) are seen in studies of MS, type I diabetes, Graves disease, discoid lupus, and SLE. Familial association studies have also reported an increased risk of several systemic autoimmune diseases among relatives of patients with a systemic autoimmune disease. This association may reflect a common etiologic pathway with shared genetic or environmental influences among these diseases. Recent genome-wide searches in RA, SLE, and MS provide evidence for multiple susceptibility genes involving major histocompatibility complex (MHC) and non-MHC loci; there is also evidence that many autoimmune diseases share a common set of susceptibility genes.

Lupus

Lupus is a chronic, systemic, inflammatory form of Arthritis that is an autoimmune disease. Lupus is an autoimmune disease. Essentially this means that the body attacks itself. Arthritic symptoms of joint pain and swelling are common with Lupus but inflammation and injury can occur in other body tissues and organs. Lupus is an unpredictable disease characterized by periods of flare-up and remission. Although, there is no cure, Lupus is treatable. Eight to ten times more women suffer from Lupus than men.

Asthma

Between 12 and 15 million people, including close to five million children, in the United States have asthma. Asthma is a chronic disease in which airflow in and out of the lungs may be blocked by muscle squeezing, swelling and excess mucus. Patients with asthma may respond to factors in the environment, called triggers, which do not affect non-asthmatics. In response to a trigger, an asthmatic's airways become narrowed and inflamed, resulting in wheezing and/or coughing symptoms.

Experimental results indicate linkage of asthma to a region on chromosome 12. (Wilkinson, J., et al., Genomics 53: 251–259, 1998. PubMed ID): 9799590) Another region of linkage mapping was identified by Holroyd et al. (Genomics 52: 233–235, 1998. PubMed ID: 9782093). The researchers examined the long arm XY pseudoautosomal region for linkage to asthma, serum IgE, and bronchial hyperresponsiveness. In 57 Caucasian families, multipoint nonparametric analyses provided evidence for linkage between DXYS154 and bronchial hyperresponsiveness (P=0.000057) or asthma (P=0.00065). This genomic region is approximately 320 kb long and contains the interleukin-9 receptor gene (300007). These results suggested that a gene controlling asthma and bronchial hyperresponsiveness may be located in this region and that IL9R is a candidate.

Analyses of sib pairs showed linkage of bronchial hyperresponsiveness with several genetic markers on chromosome 5q, including D5S436. The results were interpreted as indicating that a gene governing bronchial hyperresponsiveness is located near a major locus that regulates serum IgE levels on 5q. (Postma, D. S., et al., New Eng. J. Med. 333: 894–900, 1995. PubMed ID: 7666875)

Genes identified in the art as being associated with asthma include, but are not limited to, genes encoding the proteins listed in the following table. The table lists the art-known protein name, an NCBI GI identifying number for the protein, and an NCBI PubMed PMID identifying number and citation information for a reference or references associating the gene or protein with asthma.

| Name | GI | PMID | Citation |
| --- | --- | --- | --- |
| alpha-1-antichymotrypsin | 4501843 | 1351206 | Poller W, et al., Lancet Jun. 20, 1992; 339(8808): 1538. |
| adrenergic, alpha-1A-, receptor | 4501961 | 1970822, 8396931 | Schwinn DA, et al., J Biol Chem. May 15, 1990; 265(14): 8183–9. Hirasawa A, et al., Biochem Biophys Res Commun. Sep. 15, 1993; 195(2): 902–9. |
| adrenergic, beta-2-, receptor, surface | 4501969 | 3034889 | Kobilka BK, et al., J Biol Chem. May 25, 1987; 262(15): 7321–7. |
| interleukin 4 receptor | 4557669 | 1679753, 2307934 | Pritchard MA, et al., Genomics. July 1991 ; 10(3): 801–6. Idzerda RL, et al., J Exp Med. Mar. 1, 1990; 171(3): 861–73. |

Inflammatory Bowel Disease

In developed countries as many as two individuals in every thousand suffer from inflammatory bowel disease (ulcerative colitis and Crohn's disease). Inflammatory bowel disease—a collective term embracing both ulcerative colitis and Crohn's disease—is a significant health-care problem affecting between 0.1% and 0.2% of the population in developed countries. These important and disabling conditions are characterized by diarrhea, pain, and other intestinal symptoms, and by lifelong relapses. Ulcerative colitis is confined to the mucosal layer of the large bowel, whereas Crohn's disease can affect any portion of the intestinal tract. The pathogenesis of inflammatory bowel disease is complex but appears to involve interactions among three essential ingredients: host genetic susceptibility, intestinal bacteria, and the gut mucosal immune response. Despite impressive advances in drug therapy, most treatment strategies have two major limitations: first, they suppress or otherwise alter the host immune response, thereby neglecting the contribution of enteric bacterial microflora to disease pathogenesis; and second, current immunomodulatory drugs lack organ specificity, affecting both mucosal and systemic host responses and resulting in unpleasant side effects.

The immune response in the intestinal mucosa is conditioned by the indigenous bacterial microflora with which it exchanges regulatory signals. In susceptible individuals, inflammatory bowel disease arises when the immune system misperceives danger within the normal gut microflora and interprets the harmless enteric bacteria as pathogenic invaders; this leads to a breakdown in the normal regulatory constraints on mucosal immune responses to enteric bacteria. The profile of cytokines generated within the gut mucosa, which is genetically controlled and may differ from person to person, determines the features of the inflammatory process. Crohn's disease is associated with a predominance of type 1 helper T cell (TH1) cytokines such as tumor necrosis factor-a (TNF-a), interferon-g and IL-12, whereas type 2 helper T cell (TH2) cytokines such as IL-4 and particularly IL-S are usually found in ulcerative colitis. Despite redundancy among mediators of inflammation, a hierarchy of importance has emerged with TNF-a as a key effector and regulatory molecule in TH1 responses. This explains the rationale and efficacy of therapies that are designed to manipulate the intestinal cytokine milieu, for example, the treatment of Crohn's disease patients with antibodies to TNF-a.

Genes identified in the art as being associated with inflammatory bowel disease include, but are not limited to, genes encoding the proteins listed in the following table. The table lists the art-known protein name, an NCBI GI identifying number for the protein, and an NCBI PubMed PMID identifying number and citation information for a reference or references associating the gene or protein with inflammatory bowel disease.

| Name | GI | PMID | Citation |
| --- | --- | --- | --- |
| interleukin 2 receptor, beta | 4504665 | 2785715, 10940280, | Hatakeyama M, et al., Science. May 5, 1989; 244(4904): 551–6. Frieri G, et al., Gut. September 2000; 47(3): 410–4. |
| interleukin 10 receptor, alpha | 4504633 | 8120391, 10958782 | Liu Y, et al., J Immunol. Feb. 15, 1994; 152(4): 1821–9. Steidler L, et al., Science. Aug. 25, 2000; 289(5483): 1352–5. |
| gamma-glutamyltransferase 1 | 4885271 | 1378736, 1968061 2568315, 2885259, 2904146, 2907498, 7689219, 7906515, 8104826, 9738450, 10392451, | Courtay C, et al., Biochem Pharmacol. Jun. 23, 1992; 43(12): 2527–33. Pawlak A, et al., J Biol Chem. Feb. 25, 1990; 265(6): 3256–62. Goodspeed DC, et al., Gene. Mar. 15, 1989; 76(1): 1–9. Bulle F, et al., Hum Genet. July 1987; 76(3): 283–6. Rajpert-De Meyts E, et al., Proc Natl Acad Sci USA. December 1988; 85(23): 8840–4. |

-continued

| Name | GI | PMID | Citation |
|------|----|----|----------|
| | | 1348588 | Sakamuro D, et al., Gene. Dec. 15, 1988; 73(1): 1–9.<br>Wetmore LA, et al., Proc Natl Acad Sci USA. Aug. 15, 1993; 90(16): 7461–5.<br>Courtay C, et al., Biochem J. Feb. 1, 1994; 297 (Pt 3): 503–8.<br>Diederich M, et al., FEBS Lett. Oct. 11, 1993; 332(1–2): 88–92.<br>Leh H, et al., FEBS Lett. Aug. 28, 1998; 434(1–2): 51–6.<br>Chikhi N, et al., Comp Biochem Physiol B Biochem Mol Biol. April 1999; 122(4): 367–80. Review.<br>D'Argenio G, et al., Scand J Gastroenterol. 1992; 27(2): 111–4. |

Diabetes Type 1

Diabetes is a chronic disease that requires long-term medical attention to limit the development of its devastating complications and manage them when they do occur. It is a disproportionately expensive disease; patients diagnosed with diabetes accounted for 4.6% of the U.S. population, yet were responsible for 14.6% of all direct care expenditures in 1994. This chapter focuses on the ED evaluation and treatment of the acute and chronic complications of diabetes other than those directly associated with hypoglycemia and severe metabolic disturbances, such as diabetic ketoacidosis (DKA) and hyperosmolar nonketotic syndrome (HNKS).

Type 1 diabetes generally occurs in younger, lean patients and is characterized by the marked inability of the pancreas to secrete insulin, due to autoimmune destruction of the beta-cells. The distinguishing characteristic of a patient with Type 1 diabetes is that if insulin is withdrawn, ketosis and eventually ketoacidosis develop. These patients are therefore insulin-dependent (i.e., insulin is life-sustaining) since they produce no endogenous insulin.

The early symptoms of IDDM can be gradual or sudden. They include frequent urination (particularly at night), increased thirst, unexplained weight loss (in spite of increased appetite), and extreme tiredness. These symptoms are caused by the build-up of sugar in the blood and its loss in the urine.

To eliminate sugar in the urine, the kidney "borrows" water from the body. The loss of this extra sugar and water in the urine results in dehydration, which causes increased thirst. In addition to causing high blood glucose, the lack of insulin causes the body to break down stored fats and proteins. As fats are broken down, the body can convert these fats into waste products called ketones. If ketone production is excessive, abnormal amounts of ketones in the blood can spill into the urine. If blood ketone levels rise too high, a life-threatening condition called ketoacidosis can develop, which requires immediate medical attention.

Symptoms of ketoacidosis include abdominal pain, vomiting, rapid breathing, extreme tiredness, and drowsiness.

Diabetes requires constant attention and daily care to keep blood sugar levels in balance. Injecting insulin, following a diet, exercising, and testing blood sugar are some of the day-to-day requirements. To feel good and stay healthy, a person with IDDM must follow a daily management routine. For this reason, diabetes is often referred to as a "24-hour" disease.

Diabetes can affect many parts of the body. Over time, it can damage a person's kidneys, eyes, nerves, and heart. These long-term complications can result in kidney disease, vision loss, nerve damage, heart attack, and other problems.

The cause of type 1 diabetes is multifactorial and includes the effects of perhaps as many as 11 to 16 genes, interacting with unknown environmental agents. However, the IDDM1 locus (including the HLA-DR and DQ genes) is the only major genetic determinant, accounting for up to 50% of the familial clustering of type 1 diabetes. Among non-HLA loci, the IDDM2 locus near the insulin gene on chromosome 11p is currently partially characterized.

The remaining loci, reported from genome screening of affected sibling pairs, are only tentatively mapped to wide regions on several chromosomes. It may turn out that some of these findings are falsely-positive, and for the loci truly associated with IDDM, it may take years before the actual genes and their functions are known. However, even with the incomplete information available today, HLA-DR and DQ typing can help to predict who is at risk.

Genes identified in the art as being associated with IDDM include, but are not limited to, genes encoding the proteins listed in the following table. The table lists the art-known protein name, an NCBI GI identifying number for the protein, and an NCBI PubMed PMID identifying number and citation information for a reference or references associating the gene or protein with IDDM.

| Name | GI | PMID | Citation |
|------|----|------|----------|
| constitutive glucose transporter | 121751, 5730051 | 2834252, 3170580, 3839598, | Fukumoto H, et al., Diabetes. May 1988; 37(5): 657–61.<br>Kayano T, et al., J Biol Chem. |

-continued

| Name | GI | PMID | Citation |
|---|---|---|---|
| | | 3028891, | Oct. 25, 1988; 263(30): 15245–8. Mueckler M, et al., Science. Sep. 6, 1985; 229(4717): 941–5. Shows TB, et al., Diabetes. April 1987; 36(4): 546–9. |
| low-affinity glucose transporter | 121756 | 3399500 | Fukumoto H, et al., Proc Natl Acad Sci USA. August 1988; 85(15): 5434–8. |
| high-affinity glucose transporter | 3878426 | 9851916 | Science. Dec. 11,1998; 11; 282(5396): 2012–8. Review. |
| insulin-responsive glucose transporter | 121761 | 1397719, 1918382, 2656669, 7916714 | Buse JB, et al., Diabetes. November 1992; 41(11): 1436–45. Kusari J, et al., J Clin Invest. October 1991; 88(4): 1323–30. Fukumoto H, et al., J Biol Chem. May 15, 1989; 264(14): 7776–9. Chiaramonte R, et al., Gene. Aug. 25, 1993; 130(2): 307–8. |
| fructose transporter | 121764 | 1695905 | Kayano T, et al., J Biol Chem. Aug. 5, 1990; 265(22): 13276–82. |
| insulin-responsive-aminopeptidase*, synaptobrevin (also known as vesicle-associated membrane protein-2) | O75558 | 9553086, 9571206, 10036234 | Advani RJ, et al., J Biol Chem. Apr. 24, 1998; 273(17): 10317–24. Tang BL, et al., Biochem Biophys Res Commun. Apr. 17, 1998; 245(2): 627–32. Valdez AC, et al., J Cell Sci. March 1999; 112 (Pt 6): 845–54. |
| small guanosine triphosphate-binding protein | 1707886 | 1286667, 7543319, 7585614, 7849400, 9620768, 9668174 | Rasmussen HH, et al., Electrophoresis. December 1992; 13(12): 960–9. Bachner D, et al., Hum Mol Genet. April 1995; 4(4): 701–8. Nishimura N, et al., Cancer Res. Nov. 15, 1995; 55(22): 5445–50. Sedlacek Z, et al., Mamm Genome. October 1994; 5(10): 633–9. D'Adamo P, et al., Nat Genet. June 1998; 19(2): 134–9. Bienvenu T, et al., Hum Mol Genet. August 1998; 7(8): 1311–5. |
| syntaxin, also known as target synaptosome-associated protein receptor, or t-SNARE | 3041737 | 8206394, 8760387 | Li H, et al., Gene. Jun. 10, 1994; 143(2): 303–4. Jagadish MN, et al., Biochem J. Aug. 1, 1996; 317 (Pt 3): 945–54. |
| insulin | 124617, 4557671 | 503234, 1433291, 1601997, 1406615, 6243748, 7027261 | Bell GI, et al., Nature. Nov. 29, 1979; 282(5738): 525–7. Jorgensen AM, et al., J Mol Biol. Oct. 20, 1992; 227(4): 1146–63. Yano H, et al., J Clin Invest. June 1992; 89(6): 1902–7. Chekhranova MK, et al., Mol Biol (Mosk). May–June 1992; 26(3): 596–600. Russian. Bell GI, et al., Nature. Mar. 6, 1980; 284(5751): 26–32. Harper ME, et al., Proc Natl Acad Sci USA. July 1981; 78(7): 4458–60. |
| insulin receptor substrate | 547738, 5031805 | 1311924, 8104271, 8513971, 8599766, 8723689, 8513971 | Nishiyama M, et al., Biochem Biophys Res Commun. Feb. 28, 1992; 183(1): 280–5. Almind K, et al., Lancet. Oct. 2, 1993; 342(8875): 828–32. Araki E, et al., Diabetes. July 1993; 42(7): 1041–54. Zhou MM, et al., Nat Struct Biol. April 1996; 3(4): 388–93. Esposito DL, et al., Hum Mutat. 1996; 7(4): 364–6. Araki E, et al., Diabetes. July 1993; 42(7): 1041–54. |
| phosphatidylinositol 3-kinase | 1709513, 4505803 | 7624799 | Stoyanov B, et al., Science. Aug. 4, 1995; 269(5224): 690–3. |
| 5'-AMP-activated kinase | 3023235 | | |

-continued

| Name | GI | PMID | Citation |
|---|---|---|---|
| bradykinin | 125512, 4504893 | 2989293, 2989294, 4952632, 6441591 | Takagaki Y, et al., J Biol Chem. Jul. 15, 1985; 260(14): 8601–9. Kitamura N, et al., J Biol Chem. Jul. 15, 1985; 260(14): 8610–7. Pierce JV. Fed Proc. January–February 1968; 27(1): 52–7. Ohkubo I, et al., Biochemistry. Nov. 20, 1984; 23(24): 5691–7. |
| bradykinin receptor | 1787258, 4502391 | 9278503, 8063797 | Blattner FR, et al., Science. Sep. 5, 1997; 277(5331): 1453–74. Menke JG, et al., J Biol Chem. Aug. 26, 1994; 269(34): 21583–6. |
| IGF-I receptor | 124240, 4557665 | 1316909, 1711844, 2877871, 8247543, 1316909, 2877871, 3003744, 3107886, 8710868, 9745438 | Abbott AM, et al., J Biol Chem. May 25, 1992; 267(15): 10759–63. Cooke DW, et al., Biochem Biophys Res Commun. Jun. 28 1991; 177(3): 1113–20. Ullrich A, et al., EMBO J. October 1986; 5(10): 2503–12. Lee ST, et al., Oncogene. December 1993; 8(12): 3403–10. Abbott AM, et al., J Biol Chem. May 25, 1992; 267(15): 10759–63. Ullrich A, et al., EMBO J. October 1986; 5(10): 2503–12. Flier JS, et al., Proc Natl Acad Sci USA. February 1986; 83(3): 664–8. Francke U, et al., Cold Spring Harb Symp Quant Biol. 1986; 51 Pt 2: 855–66. Werner H, et al., Proc Natl Acad Sci USA. Aug. 6, 1996; 93(16): 8318–23. Grant ES, et al., J Clin Endocrinol Metab. September 1998; 83(9): 3252–7. |
| IGF-II receptor | 127296, 4504611 | 2957598, 2963003, 2957598, | Morgan DO, et al., Nature. Sep. 24–30, 1987; 329(6137): 301–7. Oshima A, et al., J Biol Chem. Feb. 15, 1988; 263(5): 2553–62. Morgan DO, et al., Nature. Sep. 24–30, 1987; 329(6137): 301–7. |
| leptin | 730218, 4557715 | 7499240, 7789654 | Isse N, et al., J Biol Chem. Nov. 17, 1995; 270(46): 27728–33. Masuzaki H, et al., Diabetes. July 1995; 44(7): 855–8. |
| thyroid autoantigen 70 kD (Ku antigen) | 4503841 | 2917966 | Chan JY, et al., J Biol Chem. Mar. 5, 1989; 264(7): 3651–4. |
| thyroglobulin | 4507459 | 3595599 | Malthiery Y, Eur J Biochem. Jun. 15, 1987; 165(3): 491–8. Berge-Lefranc JL, et al., Hum Genet. 1985; 69(1): 28–31. |
| thyroid hormone receptor-associated protein complex component | 4885647 | 10198638 | Ito M, et al., Mol Cell. March 1999; 3(3): 361–70. |
| thyroid hormone receptor coactivating protein | 5730053 | 8611617, 9368056 | Nielsen MS, et al., Biochim Biophys Acta. Apr. 10, 1996; 1306(1): 14–6. Monden T, et al., J Biol Chem. Nov. 21, 1997; 272(47): 29834–41. |
| thyroid hormone sulfotransferase | 7657621 | 9443824 | Fujita K, et al., J Biochem (Tokyo). November 1997; 122(5): 1052–61. |
| insulin-like 3 (Leydig cell) | 5031803 | 8020942 | Burkhardt E, et al., Genomics. Mar. 1, 1994; 20(1): 13–9. |

Genes Associated with Inflammatory Autoimmune Disease

Genes identified in the art as being associated with inflammatory autoimmune diseases include, but are not limited to, genes encoding the proteins listed in the following table. The table lists the art-known protein name, an NCBI GI identifying number for the protein, and an NCBI PubMed PMID identifying number and citation information for a reference or references associating the gene or protein with inflammatory autoimmune diseases.

| Name | GI | PMID | Citation |
|---|---|---|---|
| Granulocyte colony stimulating factor | 138971, NP_000751.1 | | Briedis DJ, Lamb RA. J Virol. April 1982; 42(1): 186–93. PMID: 6283137; UI: 82216985 Fukunaga R, Seto Y, Mizushima S, Nagata S. Proc Natl Acad Sci USA. November 1990; 87(22): 8702–6. PMID: 1701053; UI: 91062348 |
| Macrophage colony stimulating factor I | 164770 | | Oikawa S, Imai M, Inuzuka C, Tawaragi Y, Nakazato H, Matsuo H. Biochem Biophys Res Commun. Nov. 15, 1985; 132(3): 892–9. PMID: 2934062; UI: 86076957 |
| Granulocyte-macrophage | 306250 | | Robertson BH, Jansen RW, Khanna B, Totsuka A, Nainan OV, Siegl G, Widell A, Margolis HS, Isomura S, Ito K, et al. J Gen Virol. June 1992; 73 (Pt 6): 1365–77. PMID: 1318940; UI: 92300330 |
| Mast/stem cell growth factor receptor | 4557695, NP_000213.1 | | Yarden Y, Kuang WJ, Yang-Feng T, Coussens L, Munemitsu S, Dull TJ, Chen E, Schlessinger J, Francke U, Ullrich A. EMBO J. November 1987; 6(11): 3341–51. PMID: 2448137; UI: 88111521 Andre C, Hampe A, Lachaume P, Martin E, Wang XP, Manus V, Hu WX, Galibert F. Genomics. Jan. 15, 1997; 39(2): 216–26. PMID: 9027509; UI: 97179223 |
| Interferon-gamma receptor alpha chain | NP_000407.1 | | Le Coniat M, Alcaide-Loridan C, Fellous M, Berger R. Hum Genet. December 1989; 84(1): 92–4. PMID: 2532616; UI: 90109176 Aguet M, Dembic Z, Merlin G. Cell. Oct. 21, 1988; 55(2): 273–80. PMID: 2971451; UI: 89003065 |
| Analogs of macrophage stimulating protein | 123114 | | U.S. Pat. No. 5,948,892 Han S, Stuart LA, Degen SJ. Biochemistry. Oct. 8, 1991; 30(40): 9768–80. PMID: 1655021; UI: 92002016 |
| Anti-inflammatory CD14 polypeptides | 115956 | | U.S. Pat. No. 5,869,055 Ferrero E, Goyert SM. Nucleic Acids Res. May 11, 1988; 16(9): 4173. No abstract available. PMID: 2453848; UI: 88234022 Simmons DL, Tan S, Tenen DG, Nicholson-Weller A, Seed B. Blood. January 1989; 73(1): 284–9. PMID: 2462937; UI: 89088540 |
| adenosine deaminase, RNA-specific, isoform ADAR-a | 4501917 | | Wang Y, Zeng Y, Murray JM, Nishikura K. J Mol Biol. Nov. 24, 1995; 254(2): 184–95. PMID: 7490742; UI: 96083821 Patterson JB, Samuel CE. Mol Cell Biol. October 1995; 15(10): 5376–88. PMID: 7565688; UI: 96009564 |
| ADP-ribosyltransferase (NAD+; poly (ADP-ribose) polymerase) | 4501955 | | Cherney BW, McBride OW, Chen DF, Alkhatib H, Bhatia K, Hensley P, Smulson ME. Proc Natl Acad Sci USA. December 1987; 84(23): 8370–4. PMID: 2891139; UI: 88068596 |
| aggrecan 1, isoform 1 | 4501991 | | Doege KJ, Sasaki M, Kimura T, Yamada Y. J Biol Chem. Jan. 15, 1991; 266(2): 894–902. PMID: 1985970; UI: 91093289 Baldwin CT, Reginato AM, Prockop DJ. |

-continued

| Name | GI | PMID | Citation |
|---|---|---|---|
| | | | J Biol Chem. Sep. 25, 1989; 264(27): 15747–50. PMID: 2789216; UI: 89380154 Barry FP, Neame PJ, Sasse J, Pearson D. Matrix Biol. August 1994; 14(4): 323–8. PMID: 7827755; UI: 95128522 Korenberg JR, Chen XN, Doege K, Grover J, Roughley PJ. Genomics. May 1993; 16(2): 546–8. No abstract available. PMID: 8314595; UI: 93300539 |
| A kinase (PRKA) anchor protein 1 | 4502015 | | Lin RY, Moss SB, Rubin CS. J Biol Chem. Nov. 17, 1995; 270(46): 27804. PMID: 7499250; UI: 96070913 Trendelenburg G, Hummel M, Riecken EO, Hanski C. Biochem Biophys Res Commun. Aug. 5, 1996; 225(1): 313–9. PMID: 8769136; UI: 96332447 |
| A kinase (PRKA) anchor protein 4 | 4502017 | | Mohapatra B, Verna S, Shankar S, Suri A. Biochem Biophys Res Commun. Mar. 17, 1998; 244(2): 540–5. PMID: 9514854; UI: 98189217 Turner RM, Johnson LR, Haig-Ladewig L, Gerton GL, Moss SB. J Biol Chem. Nov. 27, 1998; 273(48): 32135–41. PMID: 9822690; UI: 99041985 |
| arachidonate 12-lipoxygenase | 4502051 | | Izumi T, Hoshiko S, Radmark O, Samuelsson B. Proc Natl Acad Sci USA. October 1990; 87(19): 7477–81. PMID: 2217179; UI: 91017529 |
| arachidonate 15-lipoxygenase | 4502055 | | Sigal E, Craik CS, Highland E, Grunberger D, Costello LL, Dixon RA, Nadel JA. Biochem Biophys Res Commun. Dec. 15, 1988; 157(2): 457–64. PMID: 3202857; UI: 89076270 |
| alkaline phosphatase, liver/bone/kidney | 4502063 | | Weiss MJ, Ray K, Henthorn PS, Lamb B, Kadesch T, Harris H. J Biol Chem. Aug. 25, 1988; 263(24): 12002–10. PMID: 3165380; UI: 88298884 Weiss MJ, Henthorn PS, Lafferty MA, Slaughter C, Raducha M, Harris H. Proc Natl Acad Sci USA. October 1986; 83(19): 7182–6. PMID: 3532105; UI: 87016911 |
| annexin VIII | 4502113 | | Chang KS, Wang G, Freireich EJ, Daly M, Naylor SL, Trujillo JM, Stass SA. Blood. Apr. 1, 1992; 79(7): 1802–10. PMID: 1313714; UI: 92216091 Chambers JA, Gardner E, Hauptmann R, Ponder BA, Mulligan LM. Hum Mol Genet. October 1992; 1(7): 550. PMID: 1364010; UI: 93338455 Sarkar A, Yang P, Fan YH, Mu ZM, Hauptmann R, Adolf GR, Stass SA, Chang KS. Blood. Jul. 1, 1994; 84(1): 279–86. PMID: 8018923; UI: 94289712 |
| acyloxyacyl hydrolase large subunit | 4502115 | | Hagen FS, Grant FJ, Kuijper JL, Slaughter CA, Moomaw CR, Orth K, O'Hara PJ, Munford RS. Biochemistry. Aug. 27, 1991; 30(34): 8415–23. PMID: 1883828; UI: 91355197 Whitmore TE, Mathewes SL, O'Hara PJ, Durnam DM. Genomics. May 15, 1994; 21(2): 457–8. PMID: 8088847; UI: 94375080 |

-continued

| Name | GI | PMID | Citation |
|---|---|---|---|
| arylsulfatase D isoform a | 4502239 | | Franco B, Meroni G, Parenti G, Levilliers J, Bernard L, Gebbia M, Cox L, Maroteaux P, Sheffield L, Rappold GA, et al. Cell. Apr. 7, 1995; 81(1): 15–25. PMID: 7720070; UI: 95236447 Meroni G, Franco B, Archidiacono N, Messali S, Andolfi G, Rocchi M, Ballabio A. Hum Mol Genet. April 1996; 5(4): 423–31. PMID: 8845834; UI: 96254971 |
| ADP-ribosylation factor[arf]-directed GTPase activating protein | 4502249 | | Ishikawa K, Nagase T, Nakajima D, Seki N, Ohira M, Miyajima N, Tanaka A, Kotani H, Nomura N, Ohara O. DNA Res. Oct. 31, 1997; 4(5): 307–13. PMID: 9455477; UI: 98116655 Brown MT, Andrade J, Radhakrishna H, Donaldson JG, Cooper JA, Randazzo PA. Mol Cell Biol. December 1998; 18(12): 7038–51. PMID: 9819391; UI: 99038209 |
| B-factor, properdin | 4502397 | | Horiuchi T, Kim S, Matsumoto M, Watanabe I, Fujita S, Volanakis JE. Mol Immunol. December 1993; 30(17): 1587–92. PMID: 8247029; UI: 94067177 |
| beta-transducin repeat containing | 4502477 | | Margottin F, Bour SP, Durand H, Selig L, Benichou S, Richard V, Thomas D, Strebel K, Benarous R. Mol Cell. March 1998; 1(4): 565–74. PMID: 9660940; UI: 98325370 Fujiwara T, Suzuki M, Tanigami A, Ikenoue T, Omata M, Chiba T, Tanaka K. Genomics. May 15, 1999; 58(1): 104–5. No abstract available. PMID: 10331953; UI: 99265980 |
| complement component 1, r subcomponent | 4502493 | | Journet A, Tosi M. Biochem J. Dec. 15, 1986; 240(3): 783–7. PMID: 3030286; UI: 87156625 |
| complement component 4B | 4502501 | | Belt KT, Carroll MC, Porter RR. Cell. April 1984; 36(4): 907–14. PMID: 6546707; UI: 84156544 |
| caspase 10, apoptosis-related cysteine protease | 4502569 | | Fernandes-Alnemri T, Armstrong RC, Krebs J, Srinivasula SM, Wang L, Bullrich F, Fritz LC, Trapani JA, Tomaselli KJ, Litwack G, Alnemri ES. Proc Natl Acad Sci USA. July 23, 1996; 93(15): 7464–9. PMID: 8755496; UI: 96353838 |
| caspase 6, apoptosis-related cysteine protease | 4502579 | | Fernandes-Alnemri T, Litwack G, Alnemri ES. Cancer Res. July 1, 1995; 55(13): 2737–42. PMID: 7796396; UI: 95316841 Fernandes-Alnemri T, Litwack G, Alnemri ES. J Biol Chem. Dec. 9, 1994; 269(49): 30761 |
| caspase 7, apoptosis-related cysteine protease | 4502581 | | Fernandes-Alnemri T, Litwack G, Alnemri ES. J Biol Chem. Dec. 9, 1994; 269(49): 30761–4. PMID: 7983002; UI: 95074098 Fernandes-Alnemri T, Takahashi A, Armstrong R, Krebs J, Fritz L, Tomaselli KJ, Wang L, Yu Z, Croce CM, Salveson G, et al. Cancer Res. Dec. 15, 1995; 55(24): 6045–52. PMID: 8521391; UI: 96105019 |
| calpastatin | 4502587 | | Inazawa J, Nakagawa H, Misawa S, Abe T, Minoshima S, Fukuyama R, Maki M, Murachi T, Hatanaka M, Shimizu N. Cytogenet Cell Genet. 1990; 54(3– |

-continued

| Name | GI | PMID | Citation |
|---|---|---|---|
| | | | 4): 156–8. PMID: 2265559; UI: 91092124 |
| | | | Asada K, Ishino Y, Shimada M, Shimojo T, Endo M, Kimizuka F, Kato I, Maki M, Hatanaka M, Murachi T. J Enzyme Inhib. 1989; 3(1): 49–56. PMID: 2577276; UI: 91124109 |
| chemokine (C—C motif) receptor 5 | 4502639 | | Samson M, Labbe O, Mollereau C, Vassart G, Parmentier M. Biochemistry. Mar. 19, 1996; 35(11): 3362–7. PMID: 8639485; UI: 96241590
Raport CJ, Gosling J, Schweickart VL, Gray PW, Charo IF. J Biol Chem. Jul. 19, 1996; 271(29): 17161–6. PMID: 8663314; UI: 96291862
Mummidi S, Ahuja SS, McDaniel BL, Ahuja SK. J Biol Chem. Dec. 5, 1997; 272(49): 30662–71. PMID: 9388201; UI: 98049523 |
| CD22 antigen | 4502651 | | Wilson GL, Fox CH, Fauci AS, Kehrl JH. J Exp Med. Jan. 1, 1991; 173(1): 137–46. PMID: 1985119; UI: 91086838 |
| CD2 antigen (p50), sheep red blood cell receptor | 4502653 | | Seed B, Aruffo A. Proc Natl Acad Sci USA. May 1987; 84(10): 3365–9. PMID: 2437578; UI: 87204137 |
| cadherin 11 (OB-cadherin, osteoblast) | 4502717 | | Suzuki S, Sano K, Tanihara H. Cell Regul. April 1991; 2(4): 261–70. PMID: 2059658; UI: 91283540 |
| cadherin 5, VE-cadherin (vascular epithelium) | 4502727 | | Breviario F, Caveda L, Corada M, Martin-Padura I, Navarro P, Golay J, Introna M, Gulino D, Lampugnani MG, Dejana E. Arterioscler Thromb Vasc Biol. August 1995; 15(8): 1229–39. PMID: 7627717; UI: 95353875 |
| mature G-CSF protein | 4503079 | | Nagata S, Tsuchiya M, Asano S, Yamamoto O, Hirata Y, Kubota N, Oheda M, Nomura H, Yamazaki T. EMBO J. March 1986; 5(3): 575–81. PMID: 2423327; UI: 86220137
Nagata S, Tsuchiya M, Asano S, Kaziro Y, Yamazaki T, Yamamoto O, Hirata Y, Kubota N, Oheda M, Nomura H, et al. Nature. Jan. 30–Feb. 5, 1986; 319(6052): 415–8. PMID: 3484805; UI: 86118679
Le Beau MM, Lemons RS, Carrino JJ, Pettenati MJ, Souza LM, Diaz MO, Rowley JD. Leukemia. December 1987; 1(12): 795–9. PMID: 3501046; UI: 88092852 |
| endothelin converting enzyme 1 | 4503443 | | Yorimitsu K, Moroi K, Inagaki N, Saito T, Masuda Y, Masaki T, Seino S, Kimura S. Biochem Biophys Res Commun. Mar. 17, 1995; 208(2): 721–7. PMID: 7695628; UI: 95209687 |
| coagulation factor XII (Hageman factor) | 4503629 | | Cool DE, MacGillivray RT. J Biol Chem. Oct. 5, 1987; 262(28): 13662–73. PMID: 2888762; UI: 88007593
Que BG, Davie EW. Biochemistry. Apr. 8, 1986; 25(7): 1525–8. PMID: 3011063; UI: 86216049
Royle NJ, Nigli M, Cool D, MacGillivray RT, Hamerton JL. Somat Cell Mol Genet. March 1988; 14(2): 217–21. PMID: 3162339; UI: 88159410 |
| coagulation factor XIII, A1 polypeptide | 4503631 | | Grundmann U, Amann E, Zettlmeissl G, Kupper HA. Proc Natl Acad Sci USA. November 1986; 83(21): 8024–8. PMID: 2877457; UI: 87041394 |

| Name | GI | PMID | Citation |
|---|---|---|---|
| | | | Ichinose A, Davie EW. Proc Natl Acad Sci USA. August 1988; 85(16): 5829–33. PMID: 2901091; UI: 88320337
Board PG, Webb GC, McKee J, Ichinose A. Cytogenet Cell Genet. 1988; 48(1): 25–7. PMID: 2903011; UI: 89029959
Takahashi N, Tsukamoto H, Umeyama H, Castaman G, Rodeghiero F, Ichinose A. Blood. Apr. 15, 1998; 91(8): 2830–8. PMID: 9531593; UI: 98200589 |
| coagulation factor V (proaccelerin, labile factor) | 4503643 | | |
| IgG Fc binding protein | 4503681 | | Harada N, Iijima S, Kobayashi K, Yoshida T, Brown WR, Hibi T, Oshima A, Morikawa M. J Biol Chem. Jun. 13, 1997; 272(24): 15232–41. PMID: 9182547; UI: 97326096 |
| fibrinogen, A alpha polypeptide | 4503689 | | Fu Y, Weissbach L, Plant PW, Oddoux C, Cao Y, Liang TJ, Roy SN, Redman CM, Grieninger G. Biochemistry. Dec. 8, 1992; 31(48): 11968–72. PMID: 1457396; UI: 93090725
Humphries SE, Imam AM, Robbins TP, Cook M, Carritt B, Ingle C, Williamson R. Hum Genet. 1984; 68(2): 148–53. PMID: 6500566; UI: 85053129
Kant JA, Lord ST, Crabtree GR. Proc Natl Acad Sci USA. July 1983; 80(13): 3953–7. PMID: 6575389; UI: 83247396
Baumann RE, Henschen AH. Blood. Oct. 1, 1993; 82(7): 2117–24. PMID: 8400261; UI: 94003263 |
| major histocompatibility complex, class II, DO beta | 4504403 | | Tonnelle C, DeMars R, Long EO. EMBO J. November 1985; 4(11): 2839–47. PMID: 2998758; UI: 86055719 |
| major histocompatibility complex, class I-like sequence | 4504417 | | Hashimoto K, Hirai M, Kurosawa Y. Science. Aug. 4, 1995; 269(5224): 693–5. PMID: 7624800; UI: 95350662 |
| intercellular adhesion molecule 5, telencephalin | 4504563 | | Mizuno T, Yoshihara Y, Inazawa J, Kagamiyama H, Mori K. J Biol Chem. Jan. 10, 1997; 272(2): 1156–63. PMID: 8995416; UI: 97150880
Kilgannon P, Turner T, Meyer J, Wisdom W, Gallatin WM. Genomics. Dec. 1, 1998; 54(2): 328–30. PMID: 9828136; UI: 99047540 |
| interferon, alpha 10 | 4504589 | | Goeddel DV, Leung DW, Dull TJ, Gross M, Lawn RM, McCandliss R, Seeburg PH, Ullrich A, Yelverton E, Gray PW. Nature. Mar. 5, 1981; 290(5801): 20–6. PMID: 6163083; UI: 81148795 |
| interferon (alpha, beta and omega) receptor 2 | 4504601 | | Novick D, Cohen B, Rubinstein M. Cell. May 6, 1994; 77(3): 391–400. PMID: 8181059; UI: 94236684 |
| immunoglobulin mu binding protein 2 | 4504623 | | ita Y, Mizuta TR, Shirozu M, Ozawa K, Shimizu A, Honjo T. J Biol Chem. Aug. 15, 1993; 268(23): 17463–70. PMID: 8349627; UI: 93352537 |
| immunoglobin superfamily, member 3 | 4504627 | | Saupe S, Roizes G, Peter M, Boyle S, Gardiner K, De Sario A. Genomics. Sep. 15, 1998; 52(3): 305–11. PMID: 9790749; UI: 99009315 |
| interleukin 15 receptor, alpha | 4504649 | | Anderson DM, Kumaki S, Ahdieh M, Bertles J, Tometsko M, Loomis A, Giri J, Copeland NG, Gilbert DJ, Jenkins NA, et al. J Biol |

-continued

| Name | GI | PMID | Citation |
|---|---|---|---|
| | | | Chem. Dec. 15, 1995; 270(50): 29862–9. PMID: 8530383; UI: 96102040 |
| interleukin 18 receptor 1 | 4504655 | | Parnet P, Garka KE, Bonnert TP, Dower SK, Sims JE. J Biol Chem. Feb 23, 1996; 271(8): 3967–70. PMID: 8626725; UI: 96223957 Torigoe K, Ushio S, Okura T, Kobayashi S, Taniai M, Kunikata T, Murakami T, Sanou O, Kojima H, Fujii M, Ohta T, Ikeda M, Ikegami H, Kurimoto M. J Biol Chem. Oct. 10, 1997; 272(41): 25737–42. PMID: 9325300; UI: 97467370 Dale M, Nicklin MJ. Genomics. Apr. 1, 1999; 57(1): 177–9. PMID: 10191101; UI: 99208678 |
| interleukin 18 receptor accessory protein | 4504657 | | Born TL, Thomassen E, Bird TA, Sims JE. J Biol Chem. Nov. 6, 1998; 273(45): 29445–50. PMID: 9792649; UI: 99009050 |
| interleukin 1 receptor-like 2 | 4504663 | | Lovenberg TW, Crowe PD, Liu C, Chalmers DT, Liu XJ, Liaw C, Clevenger W, Oltersdorf T, De Souza EB, Maki RA. J Neuroimmunol. November 1996; 70(2): 113–22. PMID: 8898719; UI: 97054422 Dale M, Nicklin MJ. Genomics. Apr. 1, 1999; 57(1): 177–9. PMID: 10191101; UI: 99208678 |
| interleukin 6 signal transducer (gp130, oncostatin M receptor) | 4504675 | | ibi M, Murakami M, Saito M, Hirano T, Taga T, Kishimoto T. Cell. Dec. 21, 1990; 63(6): 1149–57. PMID: 2261637; UI: 91084844 Rodriguez C, Grosgeorge J, Nguyen VC, Gaudray P, Theillet C. Cytogenet Cell Genet. 1995; 70(1–2): 64–7. PMID: 7736792; UI: 95254881 |
| interleukin 7 receptor | 4504679 | | Goodwin RG, Friend D, Ziegler SF, Jerzy R, Falk BA, Gimpel S, Cosman D, Dower SK, March CJ, Namen AE, et al. Cell. Mar. 23, 1990; 60(6): 941–51. PMID: 2317865; UI: 90199875 |
| interleukin 8 receptor, alpha | 4504681 | | Ahuja SK, Ozcelik T, Milatovitch A, Francke U, Murphy PM. Nat Genet. September 1992; 2(1): 31–6. PMID: 1303245; UI: 93265118 Morris SW, Nelson N, Valentine MB, Shapiro DN, Look AT, Kozlosky CJ, Beckmann MP, Cerretti DP. Genomics. November 1992; 14(3): 685–91. PMID: 1427896; UI: 93052400 Holmes WE, Lee J, Kuang WJ, Rice GC, Wood WI. Science. Sept. 13, 1991; 253(5025): 1278–80. PMID: 1840701; UI: 91368199 Ahuja SK, Shetty A, Tiffany HL, Murphy PM. J Biol Chem. Oct. 21, 1994; 269(42): 26381–9. PMID: 7929358; UI: 95014476 |
| interleukin-1 receptor-associated kinase 2 | 4504719 | | Muzio M, Ni J, Feng P, Dixit VM. Science. Nov. 28, 1997; 278(5343): 1612–5. PMID: 9374458; UI: 98043813 Auron PE. Cytokine Growth Factor Rev. September–December 1998; 9(3–4): 221–37. Review. PMID: 9918122; UI: 99114654 |
| integrin alpha 10 | 4504741 | | Brakebusch C, Hirsch E, Potocnik A, Fassler R. J Cell Sci. December 1997; 110 (Pt 23): 2895–904. Review. PMID: 9359872; UI: |

-continued

| Name | GI | PMID | Citation |
|---|---|---|---|
| | | | 98028692<br>Camper L, Hellman U, Lundgren-Akerlund E. J Biol Chem. Aug. 7, 1998; 273(32): 20383–9. PMID: 9685391; UI: 98352078<br>Svoboda KK. Microsc Res Tech. Oct. 15, 1998; 43(2): 111–22. Review. PMID: 9822998; UI: 99040332 |
| integrin alpha 2b light chain | 4504745 | | Heidenreich R, Eisman R, Surrey S, Delgrosso K, Bennett JS, Schwartz E, Poncz M. Biochemistry. Feb. 6, 1990; 29(5): 1232–44. PMID: 2322558; UI: 90212612<br>Poncz M, Eisman R, Heidenreich R, Silver SM, Vilaire G, Surrey S, Schwartz E, Bennett JS. J Biol Chem. Jun. 25, 1987; 262(18): 8476–82. PMID: 2439501; UI: 87250457 |
| integrin alpha 4 | 4504749 | | Fernandez-Ruiz E, Pardo-Manuel de Villena F, Rubio MA, Corbi AL, Rodriguez de Cordoba S, Sanchez-Madrid F. Eur J Immunol. February 1992; 22(2): 587–90. PMID: 1537388; UI: 92164743<br>Proc Natl Acad Sci USA. May 15, 1991; 88(10): 4094–8. PMID: 2034655; UI: 91239513<br>Takada Y, Elices MJ, Crouse C, Hemler ME. EMBO J. May 1989; 8(5): 1361–8. PMID: 2788572; UI: 89356603 |
| integrin alpha 7 | 4504753 | | Song WK, Wang W, Foster RF, Bielser DA, Kaufman SJ. J Cell Biol. 1992 May; 117(3): 643–57. PMID: 1315319; UI: 92242309<br>Wang W, Wu W, Desai T, Ward DC, Kaufman SJ. Genomics. Apr. 10, 1995; 26(3): 568–70. PMID: 7607681; UI: 95331793<br>Mayer U, Saher G, Fassler R, Bornemann A, Echtermeyer F, von der Mark H, Miosge N, Poschl E, von der Mark K. Nat Genet. November 1997; 17(3): 318–23. PMID: 9354797; UI: 98016417 |
| integrin alpha L | 4504757 | | Larson RS, Corbi AL, Berman L, Springer T. J Cell Biol. February 1989; 108(2): 703–12. PMID: 2537322; UI: 89139587<br>Corbi AL, Larson RS, Kishimoto TK, Springer TA, Morton CC. J Exp Med. May 1, 1988; 167(5): 1597–607. PMID: 3284962; UI: 88214266 |
| integrin alpha M | 4504759 | | Arnaout MA, Gupta SK, Pierce MW, Tenen DG. J Cell Biol. June 1988; 106(6): 2153–8. PMID: 2454931; UI: 88257215<br>Corbi AL, Kishimoto TK, Miller LJ, Springer TA. J Biol Chem. Sep. 5, 1988; 263(25): 12403–11. PMID: 2457584; UI: 88315033<br>Hickstein DD, Hickey MJ, Ozols J, Baker DM, Back AL, Roth GJ. Proc Natl Acad Sci USA. January 1989; 86(1): 257–61. PMID: 2563162; UI: 89098893 |
| integrin alpha X | 4504765 | | Corbi AL, Garcia-Aguilar J, Springer TA. J Biol Chem. Feb. 15, 1990; 265(5): 2782–8. PMID: 2303426; UI: 90153906<br>Corbi AL, Larson RS, Kishimoto TK, Springer TA, Morton CC. J |

-continued

| Name | GI | PMID | Citation |
|---|---|---|---|
| | | | Exp Med. May 1, 1988; 167(5): 1597–607. PMID: 3284962; UI: 88214266 |
| integrin, beta 4 | 4504769 | | Suzuki S, Naitoh Y. EMBO J. March 1990; 9(3): 757–63. PMID: 2311577; UI: 90183973 |
| integrin, beta 5 | 4504773 | | Suzuki S, Huang ZS, Tanihara H. Proc Natl Acad Sci USA. July 1990; 87(14): 5354–8. PMID: 2371275; UI: 90319111 |
| killer cell immunoglobulin-like receptor, two domains, long cytoplasmic tail, 4 | 4504871 | | |
| killer cell lectin-like receptor subfamily B, member 1 | 4504879 | | Lanier LL, Chang C, Phillips JH. J Immunol. Sep. 15, 1994; 153(6): 2417–28. PMID: 8077657; UI: 94358407 Renedo M, Arce I, Rodriguez A, Carretero M, Lanier LL, Lopez-Botet M, Fernandez-Ruiz E. 1997; 46(4): 307–11. PMID: 9218532; UI: 97364686 Poggi A, Costa P, Zocchi MR, Moretta L. Eur J Immunol. September 1997; 27(9): 2345–50. PMID: 9341779; UI: 98000986 |
| kininogen | 4504893 | | |
| latent transforming growth factor beta binding protein 4 | 4505037 | | Giltay R, Kostka G, Timpl R. FEBS Lett. Jul. 14, 1997; 411(2–3): 164–8. PMID: 9271198; UI: 97415399 |
| leukocyte tyrosine kinase | 4505045 | | Krolewski JJ, Dalla-Favera R. EMBO J. October 1991; 10(10): 2911–9. PMID: 1655406; UI: 92007735 |
| lymphocyte antigen 75 | 4505053 | | Kato M, Neil TK, Clark GJ, Morris CM, Sorg RV, Hart DNJ. Immunogenetics. May 1998; 47(6): 442–50. PMID: 9553150; UI: 98221117 |
| MAP-kinase activating death domain | 4505071 | | |
| matrix metalloproteinase 3 (stromelysin 1, progelatinase) | 4505217 | | Whitham SE, Murphy G, Angel P, Rahmsdorf HJ, Smith BJ, Lyons A, Harris TJ, Reynolds JJ, Herrlich P, Docherty AJ. Biochem J. Dec. 15, 1986; 240(3): 913–6. PMID: 3030290; UI: 87156645 |
| matrix metalloproteinase 8 (neutrophil collagenase) | 4505221 | | Hasty KA, Pourmotabbed TF, Goldberg GI, Thompson JP, Spinella DG, Stevens RM, Mainardi CL. J Biol Chem. Jul. 15, 1990; 265(20): 11421–4. PMID: 2164002; UI: 90307647 |
| macrophage stimulating 1 receptor (c-met-related tyrosine kinase) | 4505265 | | Ronsin C, Muscatelli F, Mattei MG, Breathnach R. Oncogene. May 1993; 8(5): 1195–202. PMID: 8386824; UI: 93241719 |
| phosphodiesterase 4C, cAMP-specific (dunce (Drosophila)-homolog phosphodiesterase E1) | 4505665 | | Engels P, Sullivan M, Muller T, Lubbert H. FEBS Lett. Jan. 30, 1995; 358(3): 305–10. PMID: 7843419; UI: 95145731 |
| phosphodiesterase 5A | 4505667 | | Yanaka N, Kotera J, Ohtsuka A, Akatsuka H, Imai Y, Michibata H, Fujishige K, Kawai E, Takebayashi S, Okumura K, Omori K. Eur J Biochem. Jul. 15, 1998; 255(2): 391–9. PMID: 9716380; UI: 98380237 |
| phosphotipase A2, group IVC (cytosolic) | 4505851 | | Underwood KW, Song C, Kriz RW, Chang XJ, Knopf JL, Lin LL. J Biol Chem. Aug. 21, 1998; 273(34): 21926–32. PMID: 9705332; UI: 98371032 |
| plasminogen activator, urokinase | 4505863 | | |
| plasminogen activator, | 4505865 | | Vagnarelli P, Raimondi E, |

-continued

| Name | GI | PMID | Citation |
|---|---|---|---|
| urokinase receptor | | | Mazzieri R, De Carli L, Mignatti P. Cytogenet Cell Genet. 1992; 60(3–4): 197–9. PMID: 1324136; UI: 92371014 Casey JR, Petranka JG, Kottra J, Fleenor DE, Rosse WF. Blood. Aug. 15, 1994; 84(4): 1151–6. PMID: 8049431; UI: 94325556 |
| peptidylprolyl isomerase C (cyclophilin C) | 4505991 | | Schneider H, Charara N, Schmitz R, Wehrli S, Mikol V, Zurini MG, Quesniaux VF, Movva NR. Biochemistry. Jul. 12, 1994; 33(27): 8218–24. PMID: 8031755; UI: 94304830 |
| protein kinase, cAMP-dependent, catalytic, gamma | 4506059 | | Foss KB, Simard J, Berube D, Beebe SJ, Sandberg M, Grzeschik KH, Gagne R, Hansson V, Jahnsen T. Cytogenet Cell Genet. 1992; 60(1): 22–5. PMID: 1339328; UI: 92258087 Beebe SJ, Oyen O, Sandberg M, Froysa A, Hansson V, Jahnsen T. Mol Endocrinol. March 1990; 4(3): 465–75. PMID: 2342480; UI: 90258940 |
| mitogen-activated protein kinase 4 | 4506089 | | Gonzalez FA, Raden DL, Rigby MR, Davis RJ. FEBS Lett. Jun. 15, 1992; 304(2–3): 170–8. PMID: 1319925; UI: 92316223 Seger R, Krebs EG. FASEB J. June 1995; 9(9): 726–35. Review. PMID: 7601337; UI: 95324793 Li L, Wysk M, Gonzalez FA, Davis RJ. Oncogene. February 1994; 9(2): 647–9. PMID: 8290275; UI: 94119607 |
| protease, serine, 7 (enterokinase) | 4506151 | | Kitamoto Y, Veile RA, Donis-Keller H, Sadler JE. Biochemistry. Apr. 11, 1995; 34(14): 4562–8. PMID: 7718557; UI: 95234679 Kitamoto Y, Yuan X, Wu Q, McCourt DW, Sadler JE. Proc Natl Acad Sci USA. Aug. 2, 1994; 91(16): 7588–92.PMID: 8052624; UI: 94329561 |
| small inducible cytokine subfamily A (Cys—Cys), member 22 | 4506837 | | Godiska R, Chantry D, Raport CJ, Sozzani S, Allavena P, Leviten D, Mantovani A, Gray PW. J Exp Med. May 5, 1997; 185(9): 1595–604. PMID: 9151897; UI: 97296313 |
| small inducible cytokine subfamily A (Cys—Cys), member 24 | 4506839 | | |
| signaling lymphocytic activation molecule | 4506969 | | |
| TAP binding protein (tapasin) | 4507365 | | |
| thrombomodulin | 4507483 | | Jackman RW, Beeler DL, Fritze L, Soff G, Rosenberg RD. Proc Natl Acad Sci USA. September 1987; 84(18): 6425–9. PMID: 2819876; UI: 87317665 Maglott DR, Feldblyum TV, Durkin AS, Nierman WC. Mamm Genome. May 1996; 7(5): 400–1 No abstract available. PMID: 8661740; UI: 96269623 |
| thrombospondin 1 | 4507485 | | Hennessy SW, Frazier BA, Kim DD, Deckwerth TL, Baumgartel DM, Rotwein P, Frazier WA. J Cell Biol. February 1989; 108(2): 729–36. PMID: 2918029; UI: 89139590 |
| toll-like receptor1 | 4507527 | | Rock FL, Hardiman G, Timans JC, Kastelein RA, Bazan JF. Proc Natl Acad Sci USA. Jan. 20, 1998; 95(2): 588–93. PMID: 9435236; |

-continued

| Name | GI | PMID | Citation |
|---|---|---|---|
| toll-like receptor3 | 4507531 | | UI: 98118556<br>Rock FL, Hardiman G, Timans JC, Kastelein RA, Bazan JF. Proc Natl Acad Sci USA. Jan. 20, 1998; 95(2): 588–93. PMID: 9435236; UI: 98118556 |
| tumor necrosis factor receptor superfamily, member 10d, decoy with truncated death domain | 4507563 | | Marsters SA, Sheridan JP, Pitti RM, Huang A, Skubatch M, Baldwin D, Yuan J, Gurney A, Goddard AD, Godowski P, Ashkenazi A. Curr Biol. Dec. 1, 1997; 7(12): 1003–6. PMID: 9382840; UI: 98044290<br>Degli-Esposti MA, Dougall WC, Smolak PJ, Waugh JY, Smith CA, Goodwin RG. Immunity. December 1997; 7(6): 813–20. PMID: 9430226; UI: 98090091 |
| CD40 antigen | 4507581 | | Stamenkovic I, Clark EA, Seed B. EMBO J. May 1989; 8(5): 1403–10. PMID: 2475341; UI: 89356608 |
| tumor necrosis factor (ligand) superfamily, member 13 | 4507599 | | Hahne M, Kataoka T, Schroter M, Hofmann K, Irmler M, Bodmer JL, Schneider P, Bornand T, Holler N, French LE, Sordat B, Rimoldi D, Tschopp J. J Exp Med. Sep. 21, 1998; 188(6): 1185–90. PMID: 9743536; UI: 98416181 |
| alpha-2-macroglobulin | 4557225 | | Kan CC, Solomon E, Belt KT, Chain AC, Hiorns LR, Fey G. Proc Natl Acad Sci USA. April 1985; 82(8): 2282–6. PMID: 2581245; UI: 85190481 |
| angio-associated, migratory cell protein | 4557229 | | Beckner ME, Krutzsch HC, Stracke ML, Williams ST, Gallardo JA, Liotta LA. Cancer Res. May 15, 1995; 55(10): 2140–9. PMID: 7743515; UI: 95262124 |
| disintegrin and metalloprotease domain 8 | 4557253 | | Yoshiyama K, Higuchi Y, Kataoka M, Matsuura K, Yamamoto S. Genomics. April 1, 1997; 41(1): 56–62. PMID: 9126482; UI: 97271556 |
| autoimmune regulator AIRE isoform 1 | 4557291 | | Aaltonen J, Bjorses P, Sandkuijl L, Perheentupa J, Peltonen L. Nat Genet. September 1994; 8(1): 83–7. PMID: 7987397; UI: 95078929<br>Aaltonen J, Horelli-Kuitunen N, Fan JB, Bjorses P, Perheentupa J, Myers R, Palotie A, Peltonen L. Genome Res. August 1997; 7(8): 820–9. PMID: 9267805; UI: 97413162<br>Nagamine K, Peterson P, Scott HS, Kudoh J, Minoshima S, Heino M, Krohn KJ, Lalioto MD, Mullis PE, Antonarakis SE, Kawasaki K, Asakawa S, Ito F, Shimizu N. Nat Genet. December 1997; 17(4): 393–8. PMID: 9398839; UI: 98061086<br>[No authors listed] Nat Genet. December 1997; 17(4): 399–403. PMID: 9398840; UI: 98061087<br>Bjorses P, Aaltonen J, Horelli-Kuitunen N, Yaspo ML, Peltonen L. Hum Mol Genet. 1998; 7(10): 1547–53. Review. PMID: 9735375; UI: 98407935 |
| arylsulfatase B mature peptide | 4557333 | | Schuchman EH, Jackson CE, Desnick RJ. Genomics. January 1990; 6(1): 149–58. PMID: 1968043; UI: 90152677<br>Peters C, Schmidt B, Rommerskirch W, Rupp K, Zuhlsdorf M, Vingron M, Meyer HE, Pohlmann R, von Figura K. J Biol Chem. Feb. 25, 1990; 265(6): 3374–81. PMID: 2303452; UI: 90153994 |

-continued

| Name | GI | PMID | Citation |
|---|---|---|---|
| | | | Modaressi S, Rupp K, von Figura K, Peters C. Biol Chem Hoppe Seyler. May 1993; 374(5): 327–35. PMID: 7687847; UI: 93332648 |
| cell death-inducing DFFA-like effector a | 4557465 | | Inohara N, Koseki T, Chen S, Wu X, Nunez G. EMBO J. May 1, 1998; 17(9): 2526–33. PMID: 9564035; UI: 98232498 |
| endothelin 3 | 4557545 | | O'Reilly G, Charnock-Jones DS, Davenport AP, Cameron IT, Smith SK. J Clin Endocrinol Metab. December 1992; 75(6): 1545–9. PMID: 1464662; UI: 93100396 Arinami T, Ishikawa M, Inoue A, Yanagisawa M, Masaki T, Yoshida MC, Hamaguchi H. Am J Hum Genet. May 1991; 48(5): 990–6. PMID: 2018043; UI: 91206413 Onda H, Ohkubo S, Ogi K, Kosaka T, Kimura C, Matsumoto H, Suzuki N, Fujino M. FEBS Lett. Feb. 26, 1990; 261(2): 327–30. PMID: 2178974; UI: 90184472 Bloch KD, Eddy RL, Shows TB, Quertermous T. J Biol Chem. Oct. 25, 1989; 264(30): 18156–61. PMID: 2509452; UI: 90036893 |
| integrin alpha chain, alpha 6 | 4557675 | | Tamura RN, Rozzo C, Starr L, Chambers J, Reichardt LF, Cooper HM, Quaranta V. J Cell Biol. October 1990; 111(4): 1593–604. PMID: 1976638; UI: 91009492 |
| MHC class II transactivator | 4557749 | | Riley JL, Westerheide SD, Price JA, Brown JA, Boss JM. Immunity. May 1995; 2(5): 533–43. PMID: 7749984; UI: 95269136 Steimle V, Otten LA, Zufferey M, Mach B. Cell. Oct. 8, 1993; 75(1): 135–46. PMID: 8402893; UI: 94006536 |
| Notch (Drosophila) homolog 3 | 4557799 | | Larsson C, Lardelli M, White I, Lendahl U. Genomics. Nov. 15, 1994; 24(2): 253–8. PMID: 7698746; UI: 95213014 |
| integrin beta chain, beta 2 | 4557886 | | Kishimoto TK, O'Connor K, Lee A, Roberts TM, Springer TA. Cell. Feb. 27, 1987; 48(4): 681–90. PMID: 3028646; UI: 87131080 |
| mature complement component 6 | 4559406 | | Coto E, Martinez-Naves E, Dominguez O, DiScipio RG, Urra JM, Lopez-Larrea C. Immunogenetics. 1991; 33(3): 184–7. PMID: 1672663; UI: |
| proprotein convertase subtilisin/kexin type 1 | 4585714 | | Creemers JW, Roebroek AJ, Van de Ven WJ. FEBS Lett. Mar. 23, 1992; 300(1): 82–8. PMID: 1547893; UI: 92192290 |
| annexin A13 | 4757754 | | Wice BM, Gordon JI. J Cell Biol. January 1992; 116(2): 405–22. PMID: 1530946; UI: 92112982 Morgan RO, Bell DW, Testa JR, Fernandez MP. Genomics. Feb. 15, 1998; 48(1): 100–10. PMID: 9503022; UI: 98163752 |
| caspase 5, apoptosis-related cysteine protease | 4757914 | | Munday NA, Vaillancourt JP, Ali A, Casano FJ, Miller DK, Molineaux SM, Yamin TT, Yu VL, Nicholson DW. J Biol Chem. Jun. 30, 1995; 270(26): 15870–6. PMID: 7797592; UI: 95318183 |
| CD83 antigen (activated B lymphocytes, immunoglobulin superfamily) | 4757946 | | Zhou LJ, Schwarting R, Smith HM, Tedder TF. J Immunol. Jul. 15, 1992; 149(2): 735–42. PMID: 1378080; UI: 92325513 Kozlow EJ, Wilson GL, Fox CH, |

-continued

| Name | GI | PMID | Citation |
|---|---|---|---|
| | | | Kehrl JH. Blood. Jan. 15, 1993; 81(2): 454–61. PMID: 8422464; UI: 93136434 |
| cathepsin S | 4758098 | | Shi GP, Munger JS, Meara JP, Rich DH, Chapman HA. J Biol Chem. Apr. 15, 1992; 267(11): 7258–62. PMID: 1373132; UI: 92218373 |
| HLA-B associated transcript-2 | 4758108 | | Banerji J, Sands J, Strominger JL, Spies T. Proc Natl Acad Sci USA. March 1990; 87(6): 2374–8. PMID: 2156268; UI: 90192810 |
| HLA–B associated transcript-3 | 4758110 | | Banerji J, Sands J, Strominger JL, Spies T. Proc Natl Acad Sci USA. March 1990; 87(6): 2374–8. PMID: 2156268; UI: 90192810 |
| defensin, alpha 1, myeloid-related sequence | 4758146 | | Valore EV, Ganz: T. Blood. Mar. 15, 1992; 79(6): 1538–44. PMID: 1339298; UI: 92190492 Wagner MJ, Ge Y, Siciliano M, Wells DE. Genomics. May 1991; 10(1): 114–25. PMID: 2045096; UI: 91257818 |
| ephrin A1 | 4758246 | | 1: Holzman LB, Marks RM, Dixit VM. Mol Cell Biol. November 1990; 10(11): 5830–8. PMID: 2233719; UI: 91042512 |
| fibrinogen-like 1 | 4758372 | | Yamamoto T, Gotoh M, Sasaki H, Terada M, Kitajima M, Hirohashi S. Biochem Biophys Res Commun. Jun. 15, 1993; 193(2): 681–7. PMID: 8390249; UI: 93290661 |
| FK506-binding protein 2 (13 kD) | 4758382 | | Jin YJ, Albers MW, Lane WS, Bierer BE, Schreiber SL, Burakoff SJ. Proc Natl Acad Sci USA. Aug. 1, 1991; 88(15): 6677–81. PMID: 1713687; UI: 91319747 |
| heparan sulfate 6-O-sulfotransferase | 4758566 | | 1: Habuchi H, Kobayashi M, Kimata K. J Biol Chem. Apr. 10, 1998; 273(15): 9208–13. PMID: 9535912; UI: 98204920 |
| interferon-induced protein 41, 30 kD | 4758586 | | 1: Kadereit S, Gewert DR, Galabru J, Hovanessian AG, Meurs EF. J Biol Chem. Nov. 15, 1993; 268(32): 24432–41. PMID: 7693701; UI: 94043285 |
| interferon-induced protein 75, 52 kD | 4758588 | | Kadereit S, Gewert DR, Galabru J, Hovanessian AG, Meurs EF. J Biol Chem. Nov. 15, 1993; 268(32): 24432–41. PMID: 7693701; UI: 94043285 |
| immunoglobulin superfamily, member 2 | 4758590 | | Ruegg CL, Rivas A, Madani ND, Zeitung J, Laus R, Engleman EG. J Immunol. May 1, 1995; 154(9): 4434–43. PMID: 7722300; UI: 95238941 |
| interleukin enhancer binding factor 1 | 4758600 | | Li C, Lusis AJ, Sparkes R, Nirula A, Gaynor R. Genomics. July 1992; 13(3): 665–71. PMID: 1339390; UI: 92347863 Li C, Lai CF, Sigman DS, Gaynor RB. Proc Natl Acad Sci USA. Sep. 1, 1991; 88(17): 7739–43. PMID: 1909027; UI: 91352065 |
| interferon regulatory factor 7 isoform a | 4758610 | | Zhang L, Pagano JS. Mol Cell Biol. October 1997; 17(10): 5748–57. PMID: 9315633; UI: 97459673 Wathelet MG, Lin CH, Parekh BS, Ronco LV, Howley PM, Maniatis T. Mol Cell. March 1998; 1(4): 507–18. PMID: 9660935; UI: 98325365 |
| integrin, beta-like 1 (with EGF-like repeat domains) | 4758614 | | Berg RW, Leung B, Gough S, Morris C, Yao WP, Wang SX, Ni J, Krissansen GW. Genomics. Mar. 1, 1999; 56(2): 169–78. PMID: 10051402; UI: 99162403 |
| apoptosis-associated tyrosine kinase | 4758642 | | Ishikawa K, Nagase T, Suyama M, Miyajima N, Tanaka A, Kotani H, |

-continued

| Name | GI | PMID | Citation |
|---|---|---|---|
| protease, serine, 15 | 4758682 | | Nomura N, Ohara O. DNA Res. Jun. 30, 1998; 5(3): 169–76. PMID: 9734811; UI: 98403880<br>Seki N, Hayashi A, Hattori A, Kozuma S, Ohira M, Hori T, Saito T. J Hum Genet. 1999; 44(2): 141–2. PMID: 10083745; UI: 99183314<br>Amerik AYu, Petukhova GV, Grigorenko VG, Lykov IP, Yarovoi SV, Lipkin VM, Gorbalenya AE. FEBS Lett. Feb. 28, 1994; 340(1–2): 25–8. PMID: 8119403; UI: 94164302 |
| lymphocyte antigen 95 (activating NK-receptor; NK-p44) | 4758694 | | Cantoni C, Bottino C, Vitale M, Pessino A, Augugliaro R, Malaspina A, Parolini S, Moretta L, Moretta A, Biassoni R. J Exp Med. Mar. 1, 1999; 189(5): 787–96. PMID: 10049942; UI: 99160625 |
| matrix metalloproteinase 17 (membrane-inserted) | 4758726 | | |
| neuronal apoptosis inhibitory protein | 4758752 | | Roy N, Mahadevan MS, McLean M, Shutler G, Yaraghi Z, Farahani R, Baird S, Besner-Johnston A, Lefebvre C, Kang X, et al. Cell. Jan. 13, 1995; 80(1): 167–78. PMID: 7813013; UI: 95112344 |
| Notch (Drosophila) homolog 4 | 4758818 | | Li L, Huang GM, Banta AB, Deng Y, Smith T, Dong P, Friedman C, Chen L, Trask BJ, Spies T, Rowen L, Hood L. Genomics. Jul. 1, 1998; 51(1): 45–58. PMID: 9693032; UI: 98360091 |
| proprotein convertase subtilisin/kexin type 7 | 4758888 | | Meerabux 3, Yaspo ML, Roebroek AJ, Van de Ven WJ, Lister TA, Young BD. Cancer Res. Feb. 1, 1996; 56(3): 448–51. PMID: 8564950; UI: 96147248 |
| TNF receptor-associated factor 6 | 4759254 | | Cao Z, Xiong J, Takeuchi M, Kurama T, Goeddel DV. Nature. Oct. 3, 1996; 383(6599): 443–6. PMID: 8837778; UI: 96434892 |
| TGF beta receptor associated protein −1 | 4759260 | | Charng MJ, Zhang D, Kinnunen P, Schneider MD. J Biol Chem. Apr. 17, 1998; 273(16): 9365–8. PMID: 9545258; UI: 98211955 |
| interferon regulatory factor 7 isoform b | 4809284 | | Zhang L, Pagano JS. Mol Cell Biol. October 1997; 17(10): 5748–57. PMID: 9315633; UI: 97459673<br>Wathelet MG, Lin CH, Parekh BS, Ronco LV, Howley PM, Maniatis T. Mol Cell. March 1998; 1(4): 507–18. PMID: 9660935; UI: 98325365 |
| interferon regulatory factor 7 isoform d | 4809288 | | Zhang L, Pagano JS. Mol Cell Biol. October 1997; 17(10): 5748–57. PMID: 9315633; UI: 97459673 |
| a disintegrin-like and metalloprotease (reprolysin type) with thrombospondin type 1 motif, 4 | 4826641 | | Ishikawa K, Nagase T, Suyama M, Miyajima N, Tanaka A, Kotani H, Nomura N, Ohara O. DNA Res. Jun. 30, 1998; 5(3): 169–76. PMID: 9734811; UI: 98403880 |
| death-associated protein kinase 1 | 4826684 | | Deiss LP, Feinstein E, Berissi H, Cohen O, Kimchi A. Genes Dev. Jan. 1, 1995; 9(1): 15–30. PMID: 7828849; UI: 95129831<br>Feinstein E, Druck T, Kastury K, Berissi H, Goodart SA, Overhauser J, Kimchi A, Huebner K. Genomics. Sep. 1, 1995; 29(1): 305–7. No abstract available. PMID: 8530096; UI: 96079132 |
| ephrin-A3 | 4826708 | | Kozlosky CJ, Maraskovsky E, McGrew JT, VandenBos T, Teepe M, Lyman SD, Srinivasan S, Fletcher FA, Gayle RB 3rd, Cerretti DP, et al. Oncogene. Jan. 19, |

-continued

| Name | GI | PMID | Citation |
|---|---|---|---|
| A kinase (PRKA) anchor protein (gravin) 12- (myaesthenia gravis) | 4826750 | | 1995; 10(2): 299–306. PMID: 7838529; UI: 95140419 Kozlosky CJ, Maraskovsky E, McGrew JT, VandenBos T, Teepe M, Lyman SD, Srinivasan S, Fletcher FA, Gayle RB 3rd, Cerretti DP, et al. Oncogene. Jan. 19, 1995; 10(2): 299–306. PMID: 7838529; UI: 95140419 |
| matrix metalloproteinase 14 (membrane-inserted) | 4826834 | | Will H, Hinzmann B. Eur J Biochem. Aug. 1, 1995; 231(3): 602–8. PMID: 7649159; UI: 95377289 |
| phospholipase A2, group VII (platelet-activating factor acetylhydrolase, plasma) | 4826884 | | Tjoelker LW, Wilder C, Eberhardt C, Stafforini DM, Dietsch G, Schimpf B, Hooper S, Le Trong H, Cousens LS, Zimmerman GA, et al. Nature. Apr. 6, 1995; 374(6522): 549–53. PMID: 7700381; UI: 95214779 Tew DG, Southan C, Rice SQ, Lawrence MP, Li H, Boyd HF, Moores K, Gloger IS, Macphee CH. Arterioscler Thromb Vasc Biol. April 1996; 16(4): 591–9. PMID: 8624782; UI: 96197208 Hiramoto M, Yoshida H, Imaizumi T, Yoshimizu N, Satoh K. Stroke. December 1997; 28(12): 2417–20. PMID: 9412624; UI: 98074100 |
| phospholipase A2, group IVB (cytosolic) | 4826914 | | Pickard RT, Strifler BA, Kramer RM, Sharp JD. J Biol Chem. Mar. 26, 1999; 274(13): 8823–31. PMID: 10085124; UI: 99185108 |
| tumor necrosis factor (ligand) superfamily, member 15 | 4827032 | | |
| defensin, alpha 3, neutrophil-specific | 4885179 | | Linzmeier R, Michaelson D, Liu L, Ganz T. FEBS Lett. Apr. 26, 1993; 321 (2–3): 267–73. PMID: 8477861; UI: 93238968 |
| epidermal growth factor receptor (avian erythroblastic leukemia viral (v-erb-b) oncogene homolog) | 4885199 | | Ullrich A, Coussens L, Hayflick JS, Dull TJ, Gray A, Tam AW, Lee J, Yarden Y, Libermann TA, Schlessinger J, et al. Nature. May 31–Jun. 6, 1984; 309(5967): 418–25. PMID: 6328312; UI: 84219729 |
| lymphocyte adaptor protein | 4885455 | | |
| interferon gamma receptor 2 (interferon gamma transducer 1) | 5031783 | | Soh J, Donnelly RJ, Kotenko S, Mariano TM, Cook JR, Wang N, Emanuel S, Schwartz B, Miki T, Pestka S. Cell. Mar. 11, 1994; 76(5): 793–802. PMID: 8124716; UI: 94170380 |
| leukocyte immunoglobulin-like receptor, subfamily B (with TM and ITIM domains), member 2 | 5031911 | | Wagtmann N, Rojo S, Eichler E, Mohrenweiser H, Long EO. Curr Biol. Aug. 1, 1997; 7(8): 615–8. No abstract available. PMID: 9259559; UI: 97411157 Colonna M, Navarro F, Bellon T, Llano M, Garcia P, Samaridis J, Angman L, Cella M, Lopez-Botet M. J Exp Med. Dec. 1, 1997; 186(11): 1809–18. PMID: 9382880; UI: 98044246 |
| MHC class I polypeptide-related sequence B | 5174565 | | Bahram S; Bresnahan M, Geraghty DE, Spies T. Proc Natl Acad Sci USA. Jul. 5, 1994; 91(14): 6259–63. PMID: 8022771; UI: 94294361 Bahram S, Shiina T, Oka A, Tamiya G, Inoko H. Immunogenetics. 1996; 45(2): 161–2. No abstract available. PMID: 8952966; UI: 97113304 |
| caspase recruitment domain 4 | 5174617 | | Bertin J, Nir WJ, Fischer CM, Tayber OV, Errada PR, Grant JR, Keilty JJ, Gosselin ML, Robison |

-continued

| Name | GI | PMID | Citation |
|---|---|---|---|
| | | | KE, Wong GH, Glucksmann MA, DiStefano PS. J Biol Chem. May 7, 1999; 274(19): 12955–8. PMID: 10224040; UI: 99240667 |
| toll-like receptor 6 | 5174721 | | Takeuchi O, Kawai T, Sanjo H, Copeland NG, Gilbert DJ, Jenkins NA, Takeda K, Akira S. Gene. Apr. 29, 1999; 231(1–2): 59–65. PMID: 10231569; UI: 99250250 |
| adenylyl cyclase-associated protein | 5453595 | | Matviw H, Yu G, Young D. Mol Cell Biol. November 1992; 12(11): 5033–40. PMID: 1406678; UI: 93024449 |
| phospholipase C, epsilon | 5453912 | | Kohno T, Otsuka T, Takano H, Yamamoto T, Hamaguchi M, Terada M, Yokota J. Hum Mol Genet. April 1995; 4(4): 667–74. PMID: 7633416; UI: 95359973 |
| protein tyrosine phosphatase, non-receptor type 13 (APO-1/CD95 (Fas)-associated phosphatase) | 5453992 | | Sato T, Irie S, Kitada S, Reed JC. Science. Apr. 21, 1995; 268(5209): 411–5. PMID: 7536343; UI: 95232528 |
| A kinase (PRKA) anchor protein 3 | 5454076 | | Vijayaraghavan S, Liberty GA, Mohan J, Winfrey VP, Olson GE, Carr DW. Mol Endocrinol. May 1999; 13(5): 705–17. PMID: 10319321; UI: 99252879 Lefevre A, Duquenne C, Rousseau-Merck MF, Rogier E, Finaz C. Biochem Biophys Res Commun. May 27, 1999; 259(1): 60–6. PMID: 10334916; UI: 99268798 |
| tumor necrosis factor, alpha-induced protein 2 | 5454134 | | Sarma V, Wolf FW, Marks RM, Shows TB, Dixit VM. J Immunol. May 15, 1992; 148(10): 3302–12. PMID: 1374453; UI: 92251199 |
| A kinase (PRKA) anchor protein 6 | 5729893 | | McCartney S, Little BM, Langeberg LK, Scott JD. J Biol Chem. Apr. 21, 1995; 270(16): 9327–33. PMID: 7721854; UI: 95238446 |
| leukocyte immunoglobulin-like receptor, subfamily B (with TM and ITIM domains), member 1 | 5729927 | | Samaridis J, Colonna M. Eur J Immunol. March 1997; 27(3): 660–5. PMID: 9079806; UI: 97234532 |
| MHC class I region ORF | 5729966 | | Vernet C, Ribouchon MT, Chimini G, Jouanolle AM, Sidibe I, Pontarotti P. Immunogenetics. 1993; 38(1): 47–53. PMID: 8462994; UI: 93216307 |
| tenascin R (restrictin, janusin) | 5730098 | | Carnemolla B, Leprini A, Borsi L, Querze G, Urbini S, Zardi L. J Biol Chem. Apr. 5, 1996; 271(14): 8157–60. PMID: 8626505; UI: 96215212 |
| CD6 antigen | 5802994 | | Aruffo A, Melnick MB, Linsley PS, Seed B. J Exp Med. Oct. 1, 1991; 174(4): 949–52. PMID: 1919444; UI: 92013796 Tsuge I, Utsumi KR, Ueda R, Takamoto S, Takahashi T. Somat Cell Mol Genet. May 1985; 11(3): 217–22. PMID: 3923629; UI: 85219054 |
| leukocyte immunoglobulin-like receptor, subfamily B (with TM and ITIM domains), member 5 | 5803070 | | Borges L, Hsu ML, Fanger N, Kubin M, Cosman D. J Immunol. Dec. 1, 1997; 159(11): 5192–6. PMID: 9548455; UI: 98208234 |
| macrophage receptor with collagenous structure | 5803080 | | Elomaa O, Sankala M, Pikkarainen T, Bergmann U, Tuuttila A, Raatikainen-Ahokas A, Sariola H, Tryggvason K. J Biol Chem. Feb. 20, 1998; 273(8): 4530–8. PMID: 9468508; UI: 98136152 Kangas M, Brannstrom A, Elomaa O, Matsuda Y, Eddy R, Shows TB, Tryggvason K. Genomics. May 15, |

-continued

| Name | GI | PMID | Citation |
|---|---|---|---|
| | | | 1999; 58(1): 82–9. PMID: 10331948; UI: 99265975 |
| a disintegrin-like and metalloprotease (reprolysin type) with thrombospondin type 1 motif, 1 | 5901886 | | Kuno K, Kanada N, Nakashima E, Fujiki F, Ichimura F, Matsushima K. J Biol Chem. Jan. 3, 1997; 272(1): 556–62. PMID: 8995297; UI: 97150761<br>Tang BL, Hong W. FEBS Lett. Feb. 26, 1999; 445(2–3): 223 |
| a disintegrin-like and metalloprotease (reprolysin type) with thrombospondin type 1 motif, 8 | 5901890 | | Vazquez F, Hastings G, Ortega MA, Lane TF, Oikemus S, Lombardo M, Iruela-Arispe ML. J Biol Chem. Aug. 13, 1999; 274(33): 23349–57. PMID: 10438512; UI: 99367466 |
| B7 protein | 5901898 | | Ansari-Lari MA, Muzny DM, Lu J, Lu F, Lilley CE, Spanos S, Malley T, Gibbs RA. Genome Res. April 1996; 6(4): 314–26, PMID: 8723724; UI: 96303695<br>Ansari-Lari MA, Shen Y, Muzny DM, Lee W, Gibbs RA. Genome Res. March 1997; 7(3): 268–80. PMID: 9074930; UI: 97228904 |
| A kinase (PRKA) anchor protein 10 | 6005707 | | Huang LJ, Durick K, Weiner JA, Chun J, Taylor SS. Proc Natl Acad Sci USA. Oct. 14, 1997; 94(21): 11184–9. PMID: 9326583; UI: 97470940 |
| A kinase (PRKA) anchor protein 2 | 6005709 | | Nagase T, Ishikawa K, Suyama M, Kikuno R, Hirosawa M, Miyajima N, Tanaka A, Kotani H, Nomura N, Ohara O. DNA Res. Feb. 26, 1999; 6(1): 63–70. PMID: 10231032; UI: 99246063 |
| arylsulfatase A | 6005990 | | DeLuca C, Brown JA, Shows TB. Proc Natl Acad Sci USA. April 1979; 76(4): 1957–61. PMID: 36611; UI: 79201719<br>Narahara K, Takahashi Y, Murakami M, Tsuji K, Yokoyama Y, Murakami R, Ninomiya S, Seino Y. J Med Genet. June 1992; 29(6): 432–3. Review. PMID: 1352356; UI: 92318248 |
| integrin alpha E heavy chain | 6007851 | | Austrup F, Rebstock S, Kilshaw PJ, Hamann A. Eur J Immunol. June 1995; 25(6): 1487–91. PMID: 7614974; UI: 95339856 |
| BCL2-associated athanogene 3 | 6631073 | | Takayama S, Xie Z, Reed JC. J Biol Chem. Jan. 8, 1999; 274(2): 781–6. PMID: 9873016; UI: 99091615 |
| natural killer-tumor recognition sequence | 6631100 | | Young HA, Jenkins NA, Copeland NG, Simek S, Lerman MI, Zbar B, Glenn G, Ortaldo JR, Anderson SK. Genomics. May 1993; 16(2): 548–9. PMID: 8314596; UI: 93300540 |
| arylsulfatase D isoform b | 6806885 | | Franco B, Meroni G, Parenti G, Levilliers J, Bernard L, Gebbia M, Cox L, Maroteaux P, Sheffield L, Rappold GA, et al. Cell. Apr. 7, 1995; 81(1): 15–25. PMID: 7720070; UI: 95236447<br>Meroni G, Franco B, Archidiacono N, Messali S, Andolfi G, Rocchi M, Ballabio A. Hum Mol Genet. April 1996; 5(4): 423–31. PMID: 8845834; UI: 96254971 |
| galectin 9, long isoform | 6806890 | | Tureci O, Schmitt H, Fadle N, Pfreundschuh M, Sahin U. J Biol Chem. Mar. 7, 1997; 272(10): 6416–22. PMID: 9045665; UI: 97197815<br>Matsumoto R, Matsumoto H, Seki M, Hata M, Asano Y, Kanegasaki S, Stevens RL, Hirashima M. J |

-continued

| Name | GI | PMID | Citation |
|---|---|---|---|
| | | | Biol Chem. Jul. 3, 1998; 273(27): 16976–84. PMID: 9642261; UI: 98307937 |
| lymphotoxin alpha | 6806893 | | Matsuyama N, Okawa N, Tsukii Y, Endo T, Kaji A. FEBS Lett. May 11, 1992; 302(2): 141–4. PMID: 1353024; UI: 92339500 |
| CD3-epsilon-associated protein; antisense to ERCC-1 | 6912246 | | Whitehead CM, Winkfein RJ, Fritzler MJ, Rattner JB. Chromosoma. December 1997; 106(8): 493–502. PMID: 9426281; UI: 98089111 Yamazaki T, Hamano Y, Tashiro H, Itoh K, Nakano H, Miyatake S, Saito T. J Biol Chem. Jun. 25, 1999; 274(26): 18173–80. PMID: 10373416; UI: 99303573 |
| COMPLEMENT COMPONENT C1q RECEPTOR | 6912282 | | Malhotra R, Willis AC, Jensenius JC, Jackson J, Sim RB. Immunology. March 1993; 78(3): 341–8. PMID: 8478019; UI: 93239200 Nepomuceno RR, Henschen-Edman AH, Burgess WH, Tenner AJ. Immunity. February 1997; 6(2): 119–29. PMID: 9047234; UI: 97199258 |
| killer cell immunoglobulin-like receptor, two domains, short cytoplasmic tail, 2 | 6912472 | | Colonna M, Samaridis J. Science. Apr. 21, 1995; 268(5209): 405–8. PMID: 7716543; UI: 95232526 |
| phospholipase A2, group IID | 6912596 | | Ishizaki J, Suzuki N, Higashino K, Yokota Y, Ono T, Kawamoto K, Fujii N, Arita H, Hanasaki K. J Biol Chem. Aug. 27, 1999; 274(35): 24973–9. PMID: 10455175; UI: 99386983 |
| spondin 2, extracellular matrix protein | 6912682 | | Manda R, Kohno T, Matsuno Y, Takenoshita S, Kuwano H, Yokota J. Genomics. Oct. 1, 1999; 61(1): 5–14. PMID: 10512675; UI: 99443867 |
| aggrecan 1, isoform 2 | 6995994 | | Doege KJ, Sasaki M, Kimura T, Yamada Y. J Biol Chem. Jan. 15, 1991; 266(2): 894–902. PMID: 1985970; UI: 91093289 Baldwin CT, Reginato AM, Prockop DJ. J Biol Chem. Sep. 25, 1989; 264(27): 15747–50. PMID: 2789216; UI: 89380154 |
| interleukin 19 | 7019575 | | |
| paired immunoglobin-like receptor beta | 7305387 | | Mousseau DD, Banville D, L'Abbe D, Bouchard P, Shen SH. J Biol Chem. Feb. 11, 2000; 275(6): 4467–74. PMID: 10660620; UI: 20127940 |
| a disintegrin and metalloproteinase domain 18 | 7656861 | | Frayne J, Jury JA, Barker HL, Perry AC, Jones R, Hall L. Mol Hum Reprod. May 1998; 4(5): 429–37. PMID: 9665629; UI: 98328566 Zhu GZ, Lin Y, Myles DG, Primakoff P. Gene. Jul. 8, 1999; 234(2): 227–37. PMID: 10395895; UI: 99326496 |
| a disintegrin and metalloproteinase domain 28 | 7656863 | | Jury JA, Perry AC, Hall L. Mol Hum Reprod. December 1999; 5(12): 1127–34. PMID: 10587367; UI: 20054911 |
| a disintegrin-like and metalloprotease (reprolysin type) with thrombospondin type 1 motif, 2 | 7656867 | | Tang BL, Hong W. FEBS Lett. Feb. 26, 1999; 445(2–3): 223–5. Review. PMID: 10094461; UI: 99192284 Colige A, Sieron AL, Li SW, Schwarze U, Petty E, Wertelecki W, Wilcox W, Krakow D, Cohn DH, Reardon W, Byers PH, Lapiere CM, Prockop D3, Nusgens BV. Am J Hum Genet. August 1999; 65(2): 308–17. PMID: 10417273; UI: 99347935 |

-continued

| Name | GI | PMID | Citation |
|---|---|---|---|
| cadherin EGF LAG seven-pass G-type receptor | 7656967 | | Hadjantonakis AK, Sheward WJ, Harmar AJ, de Galan L, Hoovers JM, Little PF. Genomics. Oct. 1, 1997; 45(1): 97–104. PMID: 9339365; UI: 97480720 Wu Q, Maniatis T. Cell. Jun. 11, 1999; 97(6): 779–90. PMID: 10380929; UI: 99308636 |
| Pro-(alpha)3(V) collagen | 7656989 | | Imamura Y, Scott JC, Greenspan DS. J Biol Chem. Mar. 24, 2000; 275(12): 8749–59. PMID: 10722718; UI: 20187594 |
| Interleukin-1 Superfamily 1 | 7657092 | | Smith DE, Renshaw BR, Ketchem RR, Kubin M, Garka KE, Sims JE. J Biol Chem. Jan. 14, 2000; 275(2): 1169–75. PMID: 10625660; UI: 20092888 |
| group III secreted phospholipase A2 | 7657126 | | Valentin E, Ghomashchi F, Gelb MH, Lazdunski M, Lambeau G. J Biol Chem. Mar. 17, 2000; 275(11): 7492–6. PMID: 10713052; UI: 20179839 |
| interleukin 17 receptor | 7657230 | | Yao Z, Spriggs MK, Derry JM, Strockbine L, Park LS, VandenBos T, Zappone JD, Painter SL, Armitage RJ. Cytokine. November 1997; 9(11): 794–800. PMID: 9367539; UI: 98035683 |
| killer cell immunoglobulin-like receptor, three domains, short cytoplasmic tail, 1 | 7657281 | | Dohring C, Samaridis J, Colonna M. Immunogenetics. 1996; 44(3): 227–30. PMID: 8662091; UI: 96270004 |
| metalloprotease 1 (pitrilysin family) | 7657343 | | Mzhavia N, Berman YL, Qian Y, Yan L, Devi LA. DNA Cell Biol. May 1999; 18(5): 369–80. PMID: 10360838; UI: 99287583 |
| protocadherin 11 | 7657443 | | Yoshida K, Sugano S. Genomics. Dec. 15, 1999; 62(3): 540–3. PMID: 10644456; UI: 20112772 |
| pM5 protein | 7657463 | | Templeton NS, Rodgers LA, Levy AT, Ting KL, Krutzsch HC, Liotta LA, Stetler-Stevenson WG. Genomics. January 1992; 12(1): 175–6. No abstract available. PMID: 1310294; UI: 92128984 |
| dendritic cell immunoreceptor | 7705338 | | Bates EE, Fournier N, Garcia E, Valladeau J, Durand I, Pin JJ, Zurawski SM, Patel S, Abrams JS, Lebecque S, Garrone P, Saeland S. J Immunol. Aug. 15, 1999; 163(4): 1973–83. PMID: 10438934; UI: 99370001 |
| pancreatic elastase IIB mature peptide | 7705648 | | Kawashima J, Tani T, Shimoda K, Takiguchi Y. DNA. April 1987; 6(2): 163–72. PMID: 3646943; UI: 87217962 |
| complement C1r-like proteinase precursor, | 7706083 | | |
| protocadherin 12 | 7706113 | | Wu Q, Maniatis T. Cell. Jun. 11, 1999; 97(6): 779–90. PMID: 10380929; UI: 99308636 Wu Q, Maniatis T. Proc Natl Acad Sci USA. Mar. 28, 2000; 97(7): 3124–9. PMID: 10716726; UI: 20202599 |
| tumor necrosis factor type 1 receptor associated protein | 7706485 | | |
| type 1 tumor necrosis factor receptor shedding aminopeptidase regulator | 7706545 | | Hattori A, Matsumoto H, Mizutani S, Tsujimoto M. J Biochem (Tokyo). May 1999; 125(5): 931–8. PMID: 10220586; UI: 99238715 |
| killer cell lectin-like receptor subfamily C, member 4 | 7710124 | | Plougastel B, Trowsdale J. Eur J Immunol. November 1997; 27(11): 2835–9. PMID: 9394807; UI: 98056789 |
| cytokine-like protein | 8922108 | | Liu X, Rapp N, Deans R, Cheng L. |

-continued

| Name | GI | PMID | Citation |
|---|---|---|---|
| C17 | | | Genomics. May 1, 2000; 65(3): 283–92. PMID: 10857752; UI: 20313895 |
| desmoglein 1 | 4503401 | | Wheeler GN, Parker AE, Thomas CL, Ataliotis P, Poynter D, Arnemann J, Rutman AJ, Pidsley SC, Watt FM, Rees DA, et al. Proc Natl Acad Sci USA. Jun. 1, 1991; 88(11): 4796–800. PMID: 1711210; UI: 91271279 |
| frizzled 6 | 4503831 | | Tokuhara M, Hirai M, Atomi Y, Terada M, Katoh M. Biochem Biophys Res Commun. February 13, 1998; 243(2): 622–7. PMID: 9480858; UI: 98153814 |
| kallikrein 10 | 4506157 | | Liu XL, Wazer DE, Watanabe K, Band V. Cancer Res. Jul. 15, 1996; 56(14): 3371–9. PMID: 8764136; UI: 96320486 Polikoff D, Kuo WL, Cochran JF, Wernick M, Kowbel D, Myambo K, Collins CC. Cytogenet Cell Genet. 1997; 79(1–2): 147–8. PMID: 9533035; UI: 98194229 |
| soggy-1 gene (Dickkopf gene family) | 7657554 | | Krupnik VE, Sharp JD, Jiang C, Robison K, Chickering TW, Amaravadi L, Brown DE, Guyot D, Mays G, Leiby K, Chang B, Duong T, Goodearl AD, Gearing DP, Sokol SY, McCarthy SA. Gene. Oct. 1, 1999; 238(2): 301–13. PMID: 10570958; UI: 20035735 |
| WNT16 protein | 7706773 | | |
| chemokine binding protein 2 | 4502911 | | Nibbs RJB, Wylie SM, Pragnell IB, Graham GJ. J Biol Chem. May 9, 1997; 272(19): 12495–504. PMID: 9139699; UI: 97284722 |
| putative chemokine receptor; GTP-binding protein | 5174461 | | Nomura H, Nielsen BW, Matsushima K. Int Immunol. October 1993; 5(10): 1239–49. PMID: 7505609; UI: 94092629 |
| orphan seven-transmembrane receptor, chemokine related | 7706769 | | Gosling J, Dairaghi DJ, Wang Y, Hanley M, Talbot D, Miao Z, Schall TJ. J Immunol. Mar. 15, 2000; 164(6): 2851–6. PMID: 10706668; UI: 20171478 Schweickart VL, Epp A, Raport CJ, Gray PW. J Biol Chem. Mar. 31, 2000; 275(13): 9550–6. PMID: 10734104; UI: 20200450 Khoja H) Wang G, Ng CT, Tucker J, Brown T, Shyamala V. Gene. Apr. 4, 2000; 246(1–2): 229–38. PMID: 10767544; UI: 20231748 |

SNPs

The genomes of all organisms undergo spontaneous mutation in the course of their continuing evolution, generating variant forms of progenitor sequences (Gusella, Ann. Rev. Biochem. 55, 831–854 (1986)). The variant form may confer an evolutionary advantage or disadvantage relative to a progenitor form or may be neutral. In some instances, a variant form confers a lethal disadvantage and is not transmitted to subsequent generations of the organism. In other instances, a variant form confers an evolutionary advantage to the species and is eventually incorporated into the DNA of many or most members of the species and effectively becomes the progenitor form. Additionally, the effect of a variant form may be both beneficial and detrimental, depending on the circumstances. For example, a heterozygous sickle cell mutation confers resistance to malaria, but a homozygous sickle cell mutation is usually lethal. In many instances, both progenitor and variant form(s) survive and co-exist in a species population. The coexistence of multiple forms of a sequence gives rise to polymorphisms, such as SNPs.

The reference allelic form is arbitrarily designated and may be, for example, the most abundant form in a population, or the first allelic form to be identified, and other allelic forms are designated as alternative, variant or polymorphic alleles. The allelic form occurring most frequently in a selected population is sometimes referred to as the "wild type" form.

Approximately 90% of all polymorphisms in the human genome are single nucleotide polymorphisms (SNPs). SNPs are single base pair positions in DNA at which different alleles, or alternative nucleotides, exist in some population. The SNP position, or SNP site, is usually preceded by and followed by highly conserved sequences of the allele (e.g., sequences that vary in less than 1/100 or 1/1000 members of the populations). An individual may be homozygous or heterozygous for an allele at each SNP position. As defined by the present invention, the least frequent allele at a SNP position can have any frequency that is less than the frequency of the more frequent allele, including a frequency of less than 1% in a population. A SNP can, in some instances, be referred to as a "cSNP" to denote that the nucleotide sequence containing the SNP is an amino acid coding sequence.

A SNP may arise due to a substitution of one nucleotide for another at the polymorphic site. Substitutions can be transitions or transversions. A transition is the replacement of one purine nucleotide by another purine nucleotide, or one pyrimidine by another pyrimidine. A transversion is the replacement of a purine by a pyrimidine, or vice versa. A SNP may also be a single base insertion/deletion variant (referred to as "indels"). A substitution that changes a codon coding for one amino acid to a codon coding for a different amino acid is referred to as a non-synonymous codon change, or missense mutation. A synonymous codon change, or silent mutation, is one that does not result in a change of amino acid due to the degeneracy of the genetic code. A nonsense mutation is a type of non-synonymous codon change that results in the formation of a stop codon, thereby leading to premature termination of a polypeptide chain and a defective protein.

SNPs, in principle, can be bi-, tri-, or tetra-allelic. However, tri- and tetra-allelic polymorphisms are extremely rare, almost to the point of nonexistence (Brookes, *Gene* 234 (1999) 177–186). For this reason, SNPs are often referred to as "bi-allelic markers", or "di-allelic markers".

Causative SNPs are those SNPs that produce alterations in gene expression or in the expression or function of a gene product, and therefore are most predictive of a possible clinical phenotype. One such class includes SNPs falling within regions of genes encoding a polypeptide product, i.e. cSNPs. These SNPs may result in an alteration of the amino acid sequence of the polypeptide product (i.e., non-synonymous codon changes) and give rise to the expression of a defective or other variant protein. Furthermore, in the case of nonsense mutations, a SNP may lead to premature termination of a polypeptide product. Such variant products can result in a pathological condition, e.g., genetic disease. Examples of genes in which a polymorphism within a coding sequence gives rise to genetic disease include sickle cell anemia and cystic fibrosis. Causative SNPs do not necessarily have to occur in coding regions; causative SNPs can occur in any region that can ultimately affect the expression and/or activity of the protein encoded by the nucleic acid. Such gene areas include those involved in transcription, such as SNPs in promoter regions, in gene areas involved in transcript processing, such as SNPs at intron-exon boundaries that may cause defective splicing, or SNPs in mRNA processing signal sequences such as polyadenylation signal regions. For example, a SNP may inhibit splicing of an intron and result in mRNA containing a premature stop codon, leading to a defective protein. Consequently, SNPs in regulatory regions can have substantial phenotypic impact.

Some SNPs that are not causative SNPs nevertheless are in close association with, and therefore segregate with, a disease-causing sequence. In this situation, the presence of the SNP correlates with the presence of, or susceptibility to, the disease. These SNPs are invaluable for diagnostics and disease susceptibility screening.

Clinical trials have shown that patient response to treatment with pharmaceuticals is often heterogeneous. Thus there is a need for improved approaches to pharmaceutical agent design and therapy. SNPs can be used to help identify patients most suited to therapy with particular pharmaceutical agents (this is often termed "pharmacogenomics"). Pharmacogenomics can also be used in pharmaceutical research to assist the drug selection process. (Linder et al. (1997), Clinical Chemistry, 43, 254; Marshall (1997), Nature Biotechnology, 15, 1249; International Patent Application WO 97/40462, Spectra Biomedical; and Schafer et al. (1998), Nature Biotechnology, 16, 3.).

Population Genetics

Population Genetics is the study of how Mendel's laws and other genetic principles apply to entire populations. Such a study is essential to a proper understanding of the genetic basis of inflammatory and autoimmune disorders and SNP-based association studies and linkage disequilibrium mapping. Population genetics thus seeks to understand and to predict the effects of such genetic phenomena as segregation, recombination, and mutation; at the same time, population genetics must take into account such ecological and evolutionary factors as population size, patterns of mating, geographic distribution of individuals, migration and natural selection.

Linkage is the coinheritance of two or more nonallelic genes because their loci are in close proximity on the same chromosome, such that after meiosis they remain associated more often than the 50% expected for unlinked genes. During meiosis, there is a physical crossing over, it is clear that during the production of germ cells there is a physical exchange of maternal and paternal genetic contributions between individual chromatids. This exchange necessarily separates genes in chromosomal regions that were contiguous in each parent and, by mixing them with retained linear order, results in "recombinants". The process of forming recombinants through meiotic crossing-over is an essential feature in the reassortment of genetic traits and is central to understanding the transmission of genes.

Recombination generally occurs between large segments of DNA. This means that contiguous stretches of DNA and genes are likely to be moved together. Conversely, regions of the DNA that are far apart on a given chromosome are more likely to become separated during the process of crossing-over than regions of the DNA that are close together.

It is possible to use polymorphic molecular markers, such as SNPs, to clarify the recombination events that take place during meiosis. They are used as position markers and regional identifying characters along chromosomes and can also be used to distinguish paternally derived gene regions from maternally derived gene regions.

The pattern of a set of markers along a chromosome is referred to as a "Haplotype". Therefore sets of alleles on the same small chromosomal segment tend to be transmitted as a block through a pedigree. By analyzing the haplotypes in a series of offspring of parents whose haplotypes are known, it is possible to establish which parental segment of which chromosome was transmitted to which child. When not broken up by recombination, haplotypes can be treated for mapping purposes as alleles at a single highly polymorphic locus.

The existence of a preferential occurrence of a disease gene in association with specific alleles of linked markers, such as SNPs, is called "Linkage Disequilibrium"(LD). This sort of disequilibrium generally implies that most of the disease chromosomes carry the same mutation and the markers being tested are quite close to the disease gene. For example, there is considerable linkage disequilibrium across the entire HLA locus. The A3 allele is in LD with the B7 and B14 alleles, and as a result B7 and B14 are also highly associated with hemochromatosis. Thus, HLA typing alone can significantly alter the estimate of risk for hemochromatosis, even if other family members are not available for formal linkage analysis. Consequently, by using a combination of several markers surrounding the presumptive location of the gene, a haplotype can be determined for affected and unaffected family members.

SNP-Based Association Analysis and Linkage Disequilibrium Mapping

SNPs are useful in association studies for identifying particular SNPs, or other polymorphisms, associated with pathological conditions, such as inflammatory and autoimmune disorders. Association studies may be conducted within the general population and are not limited to studies performed on related individuals in affected families (linkage studies). An association study using SNPs involves determining the frequency of the SNP allele in many patients with the disorder of interest, such as inflammatory and autoimmune disorders, as well as controls of similar age and race. The appropriate selection of patients and controls is critical to the success of SNP association studies. Therefore, a pool of individuals with well-characterized phenotypes is extremely desirable. For example, blood pressure and heart rate can be correlated with SNP patterns in hypertensive individuals in whom these physiological parameters are known in order to find associations between particular SNP genotypes and known phenotypes. Significant associations between particular SNPs or SNP haplotypes and phenotypic characteristics can be determined by standard statistical methods. Association analysis can either be direct or LD based. In direct association analysis, causative SNPs are tested that are candidates for the pathogenic sequence itself.

In LD based SNP association analysis, random SNPs are tested over a large genomic region, possibly the entire genome, in order to find a SNP in LD with the true pathogenic sequence or pathogenic SNP. For this approach, high density SNP maps are required in order for random SNPs to be located close enough to an unknown pathogenic locus to be in linkage disequilibrium with that locus in order to detect an association. SNPs tend to occur with great frequency and are spaced uniformly throughout the genome. The frequency and uniformity of SNPs means that there is a greater probability, compared with other types of polymorphisms such as tandem repeat polymorphisms, that a SNP will be found in close proximity to a genetic locus of interest. SNPs are also mutationally more stable than tandem repeat polymorphisms, such as VNTRs. LD-based association studies are capable of finding a disease susceptibility gene without any a priori assumptions about what or where the gene is.

Currently, however, it is not feasible to do SNP association studies over the entire human genome, therefore candidate genes associated with inflammatory and autoimmune disorders are targeted for SNP identification and association analysis. The candidate gene approach uses a priori knowledge of disease pathogenesis to identify genes that are hypothesized to directly influence development of the disease. The candidate gene approach may focus on a gene that is directly targeted by a drug used to treat the disorder. To discover SNPs associated with an increased susceptibility to inflammatory and autoimmune disorders, candidate genes can be selected from systems physiologically implicated in the disease pathway. SNPs found in these genes are then tested for statistical association with disease in individuals who have the disease compared with appropriate controls. The candidate gene approach has the advantages of drastically reducing the number of candidate SNPs, and the number of individuals, that need to be typed, compared with LD-based association studies of random SNPs over large areas of, or complete, genomes. Furthermore, in the candidate gene approach, no assumptions are made about the extent of LD over any particular area of the genome.

Combined with the use of a high density map of appropriately spaced, sufficiently informative SNP markers, association studies, including linkage disequilibrium-based genome wide association studies, will enable the identification of most genes involved in complex disorders, such as inflammatory and autoimmune disorders. This will enhance the selection of candidate genes most likely to contain causative SNPs associated with a particular disease. All of the SNPs disclosed by the present invention can be employed as part of genome-wide association studies or as part of candidate gene association studies.

The present invention advances the state of the art and provides commercially useful embodiments by providing previously unidentified SNPs in genes known in the art to be associated with inflammatory and autoimmune disorders.

SUMMARY OF THE INVENTION

The present invention is based on the identification of novel SNPs and previously unknown haplotypes in genes known in the art to be associated with the pathologies of inflammatory and autoimmune disorders. Such polymorphisms/haplotypes can lead to a variety of pathologies and disorders associated with inflammatory and autoimmune disorders that are mediated/modulated by a variant gene/protein. Further, such polymorphisms are important reagents in studying the pathologies of inflammatory and autoimmune disorders.

Based on these identifications, the present invention provides methods of detecting these novel variants as well as reagents needed to accomplish this task. The invention specifically provides novel SNPs in genes known to be involved in inflammatory and autoimmune disorders, variant proteins encoded by the novel SNP forms of these genes, antibodies to the variant proteins, computer-based and data storage systems containing the novel SNP information, methods of detecting these SNPs in a sample, methods of determining a risk of having or developing a disorder mediated by a variant gene/protein, methods of screening for compounds used to treat disorders mediated by a variant gene/protein, methods of treating disorders mediated by a variant gene/protein, and methods of using the novel SNPs of the present invention for human identification. The present invention also provides genomic nucleotide sequences, transcript sequences, encoded amino acid sequences, and context sequences that contain the SNPs of the present invention.

Description of the Files Contained on the CD-R Labeled CL00790CDR

NOTE: Two duplicate copies of the CD-R are submitted herewith, labeled "Copy 1" and "Copy 2". The material on each of the duplicate CD-R's is identical. Thus, descriptions or references herein to the CD-R labeled CL00790CDR and the files contained thereon apply to both "Copy 1" and "Copy 2".

The CD-R labeled CL00790CDR contains the following two files:

1) File SEQLIST_790.txt provides the Sequence Listing of the transcript sequences (SEQ ID NOS:1–286), protein sequences (SEQ ID NOS:287–572), and genomic sequences (SEQ ID NOS:573–858) for each inflammatory and autoimmune disorders-associated gene that contains a SNP of the present invention. Also provided are the context sequences (SEQ ID NOS:859–10,823) that flank each SNP of the present invention. The context sequences generally provide about 300 bp upstream (5') and 300 bp downstream (3') of each SNP, with the SNP about in the middle of the sequence, for a total of about 600 bp of context sequence surrounding each SNP. The transcript, protein, genomic, and context sequences provided in the Sequence Listing are also provided in Table 1, where they are identified by their SEQ ID NO. The Sequence Listing is provided in text (ASCII) format. SEQLIST_790.txt is 25,156 KB in size and was created on Sep. 10, 2001.

2) File TABLE1_790.txt provides Table 1 in text (ASCII) format, which discloses the SNP and associated gene information of the present invention as indicated below in the "Detailed Description of Table I", including the context sequences (SEQ ID NOS:859–10,823) flanking each SNP and the transcript (SEQ ID NOS:1–286), protein (SEQ ID NOS:287–572), and genomic sequences (SEQ ID NOS:573–858) of the inflammatory and autoimmune disorders—associated genes that contain each SNP. File TABLE1_790.txt is 20,571 KB in size and was created on Sep. 10, 2001.

The material contained on the CD-R labeled CL00790CDR is hereby incorporated by reference pursuant to 37 CFR 1.77(b)(4).

Description of Table 1

Table 1 discloses the SNP and associated gene information of the present invention. For each SNP, Table 1 provides gene information followed by SNP information.

The gene information includes: a gene number, a Celera hCT number and/or a RefSeq NM number (the NM number is a reference number to an annotated human gene that is publicly known and whose role in disease processes is understood to the point of providing commercial uses for the naturally occurring variants herein described; the public gene identified by the NM number may be the same as the gene identified by the hCT number, or may be a homolog, or paralog thereof), the art-known gene name, the art-known protein name, Celera genomic axis position and chromosomal position/cytoband of the gene where available, a public reference (e.g., OMIM reference information, which can readily be used by one of ordinary skill in the art to associate the allelic variants of each gene provided herein with medically significant disease conditions and pathologies, thus providing readily apparent commercial utilities for the SNP information of the present invention) to the gene/protein name supporting the medical significance of the gene/protein, transcript sequence (corresponding to SEQ ID NOS:1–286 of the Sequence Listing), protein sequence (corresponding to SEQ ID NOS:287–572 of the Sequence Listing), and genomic sequence (corresponding to SEQ ID NOS:573–858 of the Sequence Listing) of the assembled genomic region containing the gene. The SEQ ID NOS provided for each sequence in Table 1 correspond with the SEQ ID NOS in the Sequence Listing, provided in file SEQLIST_790.TXT on the accompanying CD-R, label CL00790CDR. NOTE: the genomic sequences always correspond to Celera genomic sequences; where both a Celera hCT number and an NM number are provided for a gene, the transcript and protein sequences correspond to the Celera sequences identified by the hCT number; where only an NM number is provided for a gene, the transcript and protein sequences correspond to the public sequences identified for the NM number.

The SNP information includes: 300 bp of 5' and 3' context sequence (corresponding to SEQ ID NOS:859–10,823 of the Sequence Listing; in some instances, the context sequences may be reverse complemented relative to the gene/transcript sequences), Celera CV identification number for internal tracking, identified alleles, populations seen with alleles ("cau"=Caucasian, "his"=Hispanic, "chn"=Chinese, and "afr"=African, "jpn"=Japanese, "ind"=Indian, "mex"= Mexican, "ain"="American Indian, "cra"=Celera donor, "no_pop"=no population information available), SNP type ["MIS-SENSE MUTATION"=SNP causes a change in the encoded amino acid (i.e., a non-synonymous coding SNP); "INTERGENIC/UNKNOWN"=SNP occurs in an intergenic region of the genome; "UNKNOWN"=SNP is located in an uncharacterized genomic region; "SILENT MUTATION"= SNP does not cause a change in the encoded amino acid (i.e., a synonymous coding SNP); "STOP CODON MUTATION"=SNP is located in a stop codon; "NON-SENSE MUTATION"=SNP creates a stop codon; "INTRON"=SNP is located in an intron, "UTR 5"=SNP is located in a 5' UTR of a transcript; "UTR 3"=SNP is located in a 3' UTR of a transcript; "PUTATIVE UTR 5"=SNP is located in a putative 5' UTR; "PUTATIVE UTR 3"=SNP is located in a putative 3' UTR; "DONOR SPLICE SITE"= SNP is located in a donor splice site (5' intron boundary); "ACCEPTOR SPLICE SITE"=SNP is located in an acceptor splice site (3' intron boundary); "REPEATS"=SNP is located in a repeat element; CODING REGION=generally, the SNP is an insertion/deletion ("indel") polymorphism that may cause a frameshift that alters the encoded protein downstream of the SNP; EXON=SNP is located in an exon; "HUMAN-MOUSE CONSERVED REGION"=SNP is located in a region of the human genome that shares a high degree of sequence similarity with the mouse; "CON-SERVED SEGMENT PUTATIVE"=generally, SNP is located in a segment of the genome that is a putative regulatory region conserved between human and mouse; "CORE PROMOTER PREDICTION PUTATIVE"=SNP is located in a predicted core promoter; "TRANSCRIPTION FACTOR SITE PUTATIVE"=SNP is located in a predicted transcription factor binding site; "REGULATORY REGION"=SNP is located in a regulatory region; and "PUTATIVE REGULATORY REGION"=SNP is located in a putative regulatory region], affected protein (including Celera hCP or Genbank GI number, position of the amino acid residue within the protein identified by the hCP or GI number that is encoded by the codon containing the SNP, and alternative amino acids represented by 1-letter amino acid codes that are encoded by the alternative SNP alleles), and source [whether the SNP is found only in Celera data and is novel to the present invention ("Celera"), or at least one SNP allele has been found in a public database as well as in Celera data but the map position of the SNP may not be publicly known ("Celera+")].

DETAILED DESCRIPTION OF THE INVENTION

General Description

Figure 1:
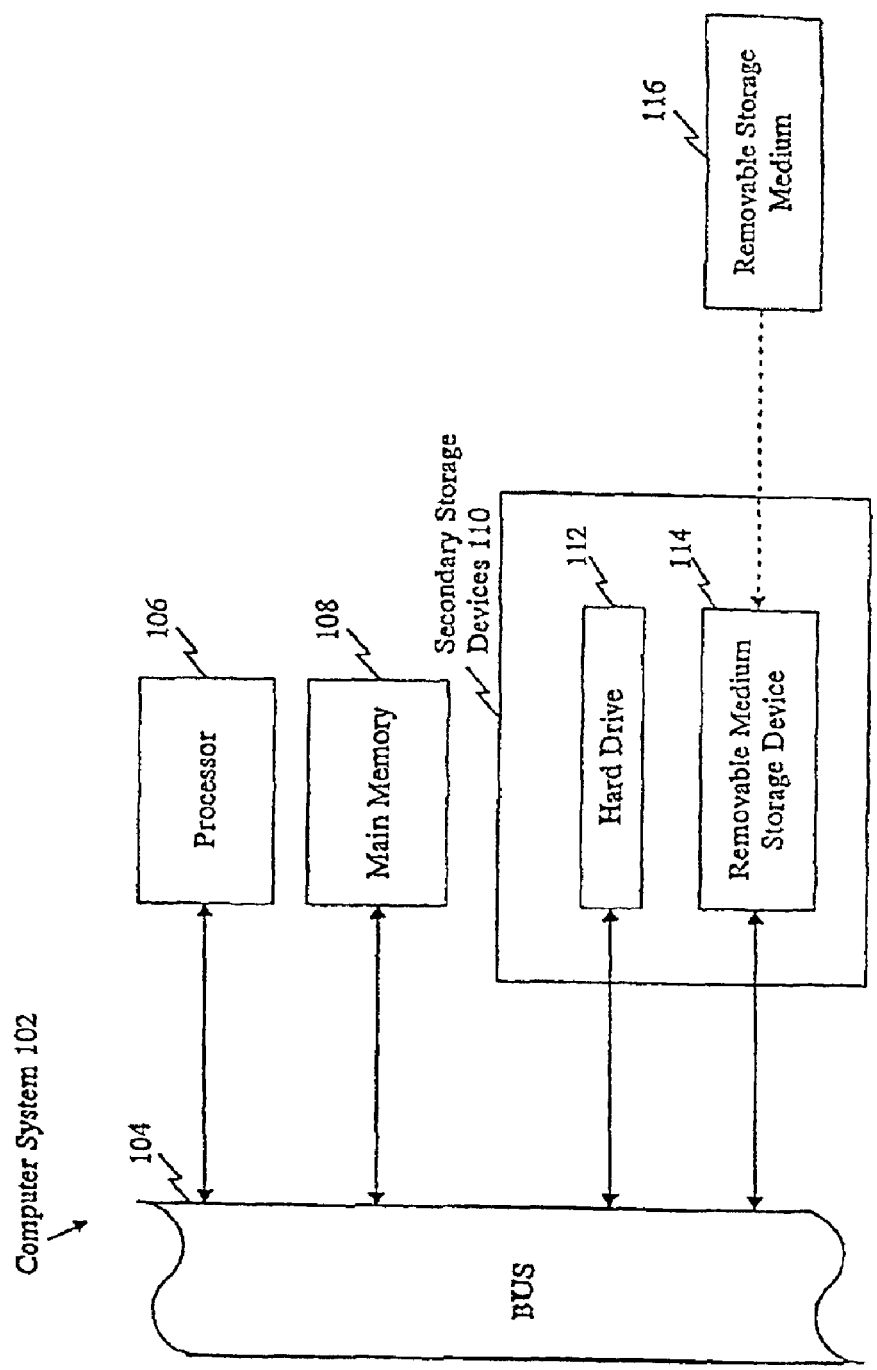
FIG. 1 provides a diagrammatic representation of a discovery system containing the SNP information of the present invention in computer readable form.

The shotgun sequencing method was used to sequence and assemble the human genome. During the sequencing phase, DNA samples from six individuals of various racial backgrounds (Caucasian, Hispanic, Chinese, and Negro) were sequenced to various extents and the sequence fragments were assembled to obtain an assembled consensus genomic sequence for human. Since DNA was sampled from six individuals, and each individual represents two sets of chromosomes, in addition to the consensus, genetic variation was found in the assemblies. These variations were subjected to rigorous analytical selection to lead to the identification of sequence variations that represent SNPs between the individuals whose DNA was sequenced.

The genomic assembly and identified sequence variation was then compared to publicly known genes involved in inflammatory and autoimmune disorders. Regions of the assemblies that represented the corresponding gene were selected and the variations are provided herein.

Based on this work, the present invention provides methods and reagents needed to detect the disclosed SNPs in genes known in the art to contribute to inflammatory and autoimmune disorders (See Background, Table 1, and the Sequence Listing). Such polymorphisms/haplotypes can lead to a variety of disorders that are mediated/modulated by a gene/protein, particularly susceptibility to inflammatory and autoimmune disorders and associated pathologies.

The present invention specifically provides genomic nucleotide sequences, cDNA sequences, amino acid sequences, and context/probes and primer sequences that contain SNPs in the genes provided in Table 1 and the Sequence Listing, methods of detecting these polymorphisms/haplotypes in a sample, methods of determining a risk of having or developing a disorder mediated by a variant gene/protein, methods of treating a disorder mediated by a SNP of the present invention, methods of screening for compounds used to treat disorders mediated by a variant gene/protein of the present invention, and methods of using the SNPs of the present invention for human identification.

Those in the art will readily recognize that nucleic acid molecules may be double stranded molecules and that reference to a particular site on one strand refers, as well, to the corresponding site on a complementary strand. Thus, in defining a polymorphic site, reference to an adenine, a thymine (uridine), a cytosine, or a guanine at a particular site on one strand of a nucleic acid molecule is also intended to include the thymine (uridine), adenine, guanine, or cytosine (respectively) at the corresponding site on a complementary strand of the nucleic acid molecule. Thus, reference may be made to either strand in order to refer to a particular SNP position. Oligonucleotide, such as probes and primers, may be designed to hybridize to either strand and SNP genotyping methods may generally target either strand. Throughout the text, in identifying a polymorphic site, reference is made to the protein encoding strand, only for the purpose of convenience.

References made throughout the text to SNP-containing nucleic acids, variant nucleic acids, or variant genes may include a SNP site alone, as well as one or more SNP sites in combination with neighboring context nucleic acid sequences that contain the SNP site(s). The nucleic acid sequence can be a nucleotide sequence comprising one or more SNPs of the present invention, or a complementary nucleotide sequence comprising a sequence complementary to one or more SNPs of the present invention.

References to either variant peptides/polypeptides, or variant proteins of the present invention includes peptides/polypeptides/proteins, or fragments thereof, that contain an amino acid that differs from the corresponding amino acid found in the "wild-type", "reference", "normal", or previously characterized peptide/polypeptide/protein due to a codon change resulting from a nonsynonymous nucleotide substitution at a SNP position disclosed by the present invention. Variant peptides/polypeptides/proteins of the present invention may also be due to a SNP disclosed by the present that generates a nonsense mutation that leads to a premature stop codon or a SNP that abolishes a stop codon, or due to any SNP disclosed by the present invention that alters the expression, structure, or function of a protein, for example, a SNP in a control element such as a promoter or enhancer or a SNP that leads to defective splicing.

Reagents for Detecting SNP Variants

In Table 1, the present invention provides the name of a kown gene that has been shown to be involved in, or implicated in, inflammatory and autoimmune disorders, its chromosomal position, a citation or public reference identifier, the transcript and protein sequence of the encoded gene products, the consensus human genome assembly containing the known gene and the SNP information of the present invention.

The SNP information is provided as context 300 base pair sequences found 3' and 5' of the variant, the alleles present at the site, and additional information about the variant, such as the nature of the SNP (coding, missense, etc.), population it was found in, etc.

The SNP information provided herein can be provided as reagents needed for detecting the variant in the form of sequence probes and primers specific for the variant sequence or antibodies specific for the variant protein, as information in discovery systems for analyzing this and/or other variants in these important genes. These reagents can be used in methods for detecting the presence of these variants and discriminating them for the art known forms.

Isolated SNP-Containing Nucleic Acid Molecules

The present invention provides isolated nucleic acid molecules that contain one or more SNPs disclosed by the present invention. The present invention further provides isolated nucleic acid molecules that encode the variant protein. Such nucleic acid molecules will consist of, consist essentially of, or comprise one or more SNPs of the present invention. The nucleic acid molecule can have additional nucleic acid residues, such as nucleic acid residues that are naturally associated with it or heterologous nucleotide sequences.

As used herein, an "isolated" SNP-containing nucleic acid molecule is one that contains a SNP of the present invention and is separated from other nucleic acid present in the natural source of the nucleic acid. Generally, the isolated SNP-containing nucleic acid, as used herein, will be comprised of one or more SNP positions disclosed by the present invention with flanking nucleotide sequence on either side of the SNP positions. Preferably the flanking sequence is up to about 300 bases, 100 bases, 50 bases, 30 bases, 15 bases, 10 bases, or 4 bases on either side of a SNP position for detection reagents or as long as the entire protein encoding sequence if it is to be used to produce a protein containing the coding variants disclosed in Table 1 and the Sequence Listing. The important point is that the nucleic acid is isolated from remote and unimportant flanking sequences and is of appropriate length such that it can be subjected to the specific manipulations or uses described herein such as recombinant expression, preparation of probes and primers for the SNP position, and other uses specific to the SNP-containing nucleic acid sequences.

Moreover, an "isolated" nucleic acid molecule, such as a cDNA molecule containing a SNP of the present invention, can be substantially free of other cellular material, or culture medium when produced by recombinant techniques, or chemical precursors or other chemicals when chemically synthesized. However, the nucleic acid molecule can be fused to other coding or regulatory sequences and still be considered isolated. For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated SNP-containing DNA molecules of the present invention. Isolated nucleic acid molecules according to the present invention further include such molecules produced synthetically.

Isolated SNP-containing nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The present invention further provides related nucleic acid molecules that hybridize under stringent conditions to the nucleic acid molecules disclosed herein. As used herein, the term "hybridizes under stringent conditions" is intended to describe conditions for hybridization and washing under which nueleotide sequences encoding a peptide at least 60–70% homologous to each other typically remain hybridized to each other. The conditions can be such that sequences at least about 60%, at least about 70%, or at least about 80%, or at least about 90% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45° C., followed by one or more washes in 0.2×SSC, 0.1% SDS at 50–65° C. Examples of moderate to low stringency hybridization conditions are well known in the art.

Variant Protein/Peptide Molecules

The present invention provides polymorphic, SNP-containing, nucleic acid sequences that encode variants of the inflammatory and autoimmune disorders associated gene product (protein) disclosed herein (See Table 1 and the Sequence Listing). These variant molecules/sequences will be referred to herein as the variants of the present invention, the variant proteins of the present invention, or variant peptides/polypeptides/proteins of the present invention.

The present invention provides isolated variant protein molecules that comprise, consist of or consist essentially of one or more variant amino acids encoded by a nonsynonymous nucleotide substitution at one or more of the SNP positions disclosed herein; also referred to as variant amino acids, peptides/polypeptides, or proteins encoded by SNPs disclosed herein.

Variant proteins include, but are not limited to deletions, additions and substitutions in the amino acid sequence of the protein caused by SNPs of the present invention. Table 1 provides the variant protein information of the present invention. For example, one class of substitutions is conserved amino acid substitutions. Such substitutions are those that substitute a given amino acid in a peptide for another amino acid of like characteristics. Typical conservative substitutions are replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant proteins can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

As used herein, a protein or peptide is said to be "isolated" or "purified" when it is substantially free of cellular material or free of chemical precursors or other chemicals. The variant peptides of the present invention can be purified to homogeneity or other degrees of purity. The level of purification will be based on the intended use. The critical feature is that the preparation allows for the desired function of the variant peptide, even if in the presence of considerable amounts of other components.

In some uses, "substantially free of cellular material" includes preparations of the variant peptide having less than about 30% (by dry weight) other proteins (i.e., contaminating protein), less than about 20% other proteins, less than about 10% other proteins, or less than about 5% other proteins. When the variant peptide is recombinantly produced, it can also be substantially free of culture medium, i.e., culture medium represents less than about 20% of the volume of the protein preparation.

The language "substantially free of chemical precursors or other chemicals" includes preparations of the variant peptide in which it is separated from chemical precursors or other chemicals that are involved in its synthesis. In one embodiment, the language "substantially free of chemical precursors or other chemicals" includes preparations of the variant protein having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated variant proteins can be purified from cells that naturally express it, purified from cells that have been altered to express it (recombinant), or synthesized using known protein synthesis methods. For example, a nucleic acid molecule containing SNP(s) encoding the variant protein is cloned into an expression vector, the expression vector introduced into a host cell and the variant protein expressed in the host cell. The variant protein can then be isolated from the cells by an appropriate purification scheme using standard protein purification techniques. Many of these techniques are described in detail below.

Accordingly, the present invention provides variant proteins that consist of amino acid sequences that contain one or more of the amino acid polymorphisms encoded by a SNP provided in Table 1. A protein consists of an amino acid sequence when the amino acid sequence is the final amino acid sequence of the protein.

The present invention further provides variant proteins that consist essentially of amino acid sequences that contain one or more of the amino acid polymorphisms encoded by a SNP provided in Table 1. A protein consists essentially of an amino acid sequence when such an amino acid sequence is present with only a few additional amino acid residues in the final protein.

The present invention further provides variant proteins that are comprised of amino acid sequences that contain one or more of the amino acid polymorphisms encoded by a SNP provided in Table 1. A protein is comprised of an amino acid sequence when the amino acid sequence is at least part of the final amino acid sequence of the protein. In such a fashion, the protein can be only the variant peptide or have additional amino acid molecules, such as amino acid residues (contiguous encoded sequence) that, are naturally associated with it or heterologous amino acid residues/peptide sequences. Such a protein can have a few additional amino acid residues or can comprise several hundred or more additional amino acids. A brief description of how various types of these proteins can be made/isolated is provided below.

The variant proteins of the present invention can be attached to heterologous sequences to form chimeric or fusion proteins. Such chimeric and fusion proteins comprise a variant protein operatively linked to a heterologous protein having an amino acid sequence not substantially homologous to the variant protein. "Operatively linked" indicates that the variant protein and the heterologous protein are fused in-frame. The heterologous protein can be fused to the N-terminus or C-terminus of the variant protein.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A variant protein-encoding nucleic acid can be cloned into such an expression vector such that the fusion moiety is linked in-frame to the variant protein.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art. Accordingly, the variant peptides of the present invention also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

The present invention further provides fragments of the variant proteins of the present invention, in addition to proteins and peptides that comprise and consist of such fragments, provided that such fragments contain one or more amino acid polymorphisms encoded by a nonsynonymous SNP substitution provided by the present invention. The fragments to which the invention pertains, however, are not to be construed as encompassing fragments that maybe disclosed publicly prior to the present invention.

As used herein, a fragment comprises at least 8 or more contiguous amino acid residues from a variant protein, wherein at least one residue is a variant amino acid encoded by a nonsynonymous nucleotide substitution at a SNP position provided by the present invention. Such fragments can be chosen based on the ability to retain one or more of the biological activities of the variant protein or could be chosen for the ability to perform a function, e.g. act as an immunogen. Particularly important fragments are biologically active fragments. Such fragments will typically comprise a domain or motif of the variant proteins of the present invention, e.g., active site or ligand binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis).

Antibodies

The invention also provides antibodies that selectively bind to the variant proteins of the present invention as well as fragments thereof. Such antibodies may be used to quantitatively or qualitatively detect the variant protein or variant peptide molecules of the present invention. As used herein, an antibody selectively binds a target variant protein when it binds the variant protein and does not significantly bind to non-variant proteins, i.e., the antibody does not bind to normal, wild-type, or previously disclosed proteins that do not contain a variant amino acid encoded by a nonsynonymous nucleotide substitution at a SNP position disclosed herein.

As used herein, an antibody is defined in terms consistent with that recognized within the art: they are multi-subunit proteins produced by a mammalian organism in response to an antigen challenge. The antibodies of the present invention include monoclonal antibodies and polyclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989). In general, to generate antibodies, an isolated peptide is used as an immunogen and is administered to a mammalian organism, such as a rat, rabbit or mouse. Either the full-length protein, an antigenic peptide fragment, or a fusion protein can be used.

Monoclonal antibodies can be produced by hybridomas, which are immortalized cell lines capable of secreting a specific monoclonal antibody. The immortalized cell lines can be created in vitro by fusing two different cell types, usually lymphocytes, one of which is a tumor cell.

Antibodies are preferably prepared from regions or discrete fragments of the variant protein containing a variant amino acid. Antibodies can be prepared from any region of the variant peptide as described herein, provided that the region contains a variant amino acid encoded by a nonsynonymous nucleotide substitution at a SNP position disclosed by the present invention. However, preferred regions will include those involved in function/activity and/or protein/binding partner interaction. An antigenic fragment will typically comprise at least 10 contiguous amino acid residues; at least one of the amino acid residues is an amino acid encoded by a SNP of the present invention. The antigenic peptide can comprise, however, at least 12, 14, 20 or more amino acid residues, provided that at least one amino acid is encoded by a SNP of the present invention. Such fragments can be selected on a physical property, such as fragments corresponding to regions that are located on the surface of the protein, e.g., hydrophilic regions or can be selected based on sequence uniqueness, or based on the position of the variant amino acid residue(s) encoded by the SNPs provided by the present invention.

Detection of an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include 125I, $^{131}$I, $^{35}$S or $^{3}$H.

Design of SNP-Containing Nucleic Acids Detection Methods

The SNP-containing nucleic acid molecules of the present invention are useful as probes, primers, chemical intermediates, and in biological assays for SNPs of the present invention. The probes/primers can correspond to one or more of the SNPs provided in Table 1 and the Sequence Listing or can correspond to a specific region 5' and/or 3' to a SNP position, particularly a region corresponding to the context sequences provided in the Sequence Listing (SEQ ID NOS:859–10,823). However, as discussed above, fragments are not to be construed as encompassing fragments that are not associated with SNPs of the present invention or those known in the art for SNP detection. The SNP-containing nucleic acid molecules and information provided herein are also useful for designing primers for PCR to amplify any given SNP of the present invention and to design any formatted SNP detection reagent/kits.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides. Depending on the particular application, the consecutive nucleotides can either include the target SNP position, or be a specific region in close enough proximity 5' and/or 3' to the SNP position to carry out the desired assay.

Preferred primer and probe sequences can readily be determined using the sequences provided in the Sequence Listing, particularly the SNP context sequences (SEQ ID NOS:859–10,823). It will be apparent to one of skill in the art that such primers and probes are useful as diagnostic probes or amplification primers for genotyping SNPs of the present invention, and can be incorporated into a kit format.

For analyzing SNPs, it may be appropriate to use oligonucleotides specific to alternative SNP alleles (referred to as "allele-specific oligonucleotides", "allele-specific probes", or "allele-specific primers"). The design and use of allele-specific probes for analyzing polymorphisms is described by e.g., Saiki et al., Nature 324, 163–166 (1986); Dattagupta, EP 235,726, Saiki, WO 89/11548.

In a hybridization-based assay, allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles. Some probes are designed to hybridize to a segment of target DNA such that the polymorphic site aligns with a central position (e.g., in a 15-mer at the 7 position; in a 16-mer, at either the 8 or 9 position) of the probe. This design of probe achieves good discrimination in hybridization between different allelic forms.

Allele-specific probes are often used in pairs, the "pairs" may be identical except for a one nucleotide mismatch that represents the allelic variants at the SNP position. One member of a pair perfectly matches a reference form of a target sequence and the other member perfectly matches a variant form. In the case of an array, several pairs of probes can then be immobilized on the same support for simultaneous analysis of multiple polymorphisms within the same target sequence.

In one type of PCR-based assay, an allele-specific primer hybridizes to a site on target DNA overlapping the SNP position and only primes amplification of an allelic form to which the primer exhibits perfect complementarity. See Gibbs, Nucleic Acid Res. 17 2427–2448 (1989). This primer is used in conjunction with a second primer that hybridizes at a distal site. Amplification proceeds from the two-primers, resulting in a detectable product that indicates the particular allelic form is present. A control is usually performed with a second pair of primers, one of which shows a single base mismatch at the polymorphic site and the other of which exhibits perfect complementarity to a distal site. The single-base mismatch prevents amplification and no detectable product is formed. The method works best when the mismatch is included in the 3'-most position of the oligonucleotide aligned with the polymorphism because this position is most destabilizing to elongation from the primer (see, e.g., WO 93/22456). This PCR-based assay can be utilized as part of the TaqMan assay, described below.

SNP Detection Kits, Nucleic Acid Arrays, and Integrated Systems

The present invention further provides SNP detection reagents and kits, such as arrays/microarrays of nucleic acid molecules, or probe/primer sets, and other detection reagent sets, that are based on the SNPs provided in Table 1 and the Sequence Listing.

In one embodiment of the present invention, kits are provided which contain the necessary reagents to carry out one or more assays that detect one or more SNPs disclosed herein. The present invention also provides multicomponent integrated systems for analyzing the SNPs provided by the present invention.

SNP detection kits may contain one or more oligonucleotide probes, or pairs of probes, that hybridize at or near each SNP position. Multiple pairs of allele-specific oligonucleotides may be included in the kit to simultaneously assay large numbers of SNPs, at least one of which is one of the SNPs of the present invention. In some kits/detection reagents, such as arrays, the allele-specific oligonucleotides are provided immobilized to a substrate. For example, the same substrate can comprise allele-specific oligonucleotide probes for detecting at least 1; 10; 100; 1000; 10,000; 100,000 or substantially all of the polymorphisms shown in Table 1 and the Sequence Listing.

Specifically, the invention provides a compartmentalized kit to receive, in close confinement, one or more containers which comprises: (a) a first container comprising one of the nucleic acid probes, for example an allele-specific oligonucleotide, that can bind to a fragment of the human genome containing a SNP disclosed herein; and (b) one or more other containers comprising one or more of the following: wash reagents or reagents capable of detecting the presence of a bound probe. Containers may be interchangeably referred to as, for example, "compartments", "chambers", or "channels".

In detail, a compartmentalized kit includes any kit in which reagents are contained in separate containers. Such containers include small glass containers, plastic containers, strips of plastic, glass or paper, or arraying material such as silica. Such containers allow one to efficiently transfer reagents from one compartment to another compartment such that the samples and reagents are not cross-contaminated, and the agents or solutions of each container can be added in a quantitative fashion from one compartment to another. Such containers may include a container which will accept the test sample, a container which contains the SNP probe, containers which contain wash reagents (such as phosphate buffered saline, Tris-buffers, etc.), and containers which contain the reagents used to detect the bound probe. The kit can further comprise reagents for PCR or other enzymatic reactions, and instructions for using the kit. One skilled in the art will readily recognize that the previously unidentified SNPs of the present invention can be routinely identified using the sequence information disclosed herein and can be readily incorporated into one of the established kit formats which are well known in the art.

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522. Arrays or microarrays are commonly referred to as "DNA chips". As used herein, arrays/microarrays may be interchangeably referred to as detection reagents or kits.

Any number of oligonucleotide probes, such as allele-specific oligonucleotides, may be implemented in an array, wherein each probe or pair of probes corresponds to a different SNP position. The oligonucleotides are synthesized at designated areas on a substrate using a light-directed chemical process. The substrate may be paper, nylon or other type of membrane, filter, chip, glass slide or any other suitable solid support.

Hybridization assays based on oligonucleotide arrays rely on the differences in hybridization stability of short oligonucleotides probes to perfectly matched and mismatched target sequence variants. Efficient access to polymorphism information is obtained through a basic structure comprising high-density arrays of oligonucleotide probes attached to a solid support (e.g., a chip) at selected positions. Each DNA chip can contain thousands to millions of individual synthetic DNA probes arranged in a grid-like pattern and miniaturized to the size of a dime, each corresponding to a particular SNP position or allelic variant. Preferably, probes are attached to a solid support in an ordered, addressable array.

The array/chip technology has already been applied with success in numerous cases. For example, the screening of mutations has been undertaken in the BRCA1 gene, in *S. cerevisiae* mutant strains, and in the protease gene of HIV-I virus (Hacia et al., 1996; Shoemaker et al., 1996; Kozal et al., 1996). Chips of various formats for use in detecting SNPs can be produced on a customized basis.

An array-based tiling strategy useful for detecting SNPs is described in EP 785280. Briefly, arrays may generally be "tiled" for a large number of specific polymorphisms. "Tiling" refers to the synthesis of a defined set of oligonucleotide probes that are made up of a sequence complementary to the target sequence of interest, as well as preselected variations of that sequence, e.g., substitution of one or more given positions with one or more members of the basis set of monomers, i.e. nucleotides. Tiling strategies are further described in PCT application No. WO 95/11995. In a particular aspect, arrays are tiled for a number of specific SNPs. In particular, the array is tiled to include a number of detection blocks, each detection block being specific for a specific SNP or a set of SNPs. For example, a detection block may be tiled to include a number of probes that span the sequence segment that includes a specific SNP. To ensure probes that are complementary to each allele, the probes are synthesized in pairs differing at the SNP position. In addition to the probes differing at the SNP position, monosubstituted probes are also generally tiled within the detection block. Such methods can readily be applied to the SNP information disclosed herein.

These monosubstituted probes have bases at and up to a certain number of bases in either direction from the polymorphism, substituted with the remaining nucleotides (selected from A, T, G, C and U). Typically the probes in a tiled detection block will include substitutions of the sequence positions up to and including those that are 5 bases away from the SNP. The monosubstituted probes provide internal controls for the tiled array, to distinguish actual hybridization from artefactual cross-hybridization. Upon completion of hybridization with the target sequence and washing of the array, the array is scanned to determine the position on the array to which the target sequence hybridizes. The hybridization data from the scanned array is then analyzed to identify which allele or alleles of the SNP are present in the sample. Hybridization and scanning may be carried out as described in PCT application No. WO 92/10092 and WO 95/11995 and U.S. Pat. No. 5,424,186.

Thus, in some embodiments, the chips may comprise an array of nucleic acid sequences of fragments of about 15 nucleotides in length. In further embodiments, the chip may comprise an array including at least one of the sequences selected from the group consisting of those disclosed in Table 1 and the Sequence Listing, and the sequences complementary thereto, or a fragment thereof, said fragment comprising at least about 8 consecutive nucleotides, preferably 10, 15, 20, more preferably 25, 30, 40, 47, or 50 consecutive nucleotides and containing a polymorphic base. In some embodiments the polymorphic base is within 5, 4, 3, 2, or 1 nucleotides from the center of the polynucleotide, more preferably at the center of said polynucleotide. In other embodiments, the chip may comprise an array containing any number of polynucleotides of the present invention.

An oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number which lends itself to the efficient use of commercially available instrumentation.

Using such arrays, the present invention provides methods of identifying the SNPs of the present invention in a sample. Such methods comprise incubating a test sample with an array comprising one or more oligonucleotide probes corresponding to at least one SNP position of the present invention, and assaying for binding of a nucleic acid from the test sample with one or more of the oligonucleotide probes. Such assays will typically involve arrays comprising oligonucleotides probes corresponding to many SNP positions and/or allelic variants of those SNP positions, at least one of which is a SNP of the present invention.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel SNPs disclosed herein. Examples of such assays can be found in Chard, T, An Introduction to Radioimmunoassay and Related Techniques, Elsevier Science Publishers, Amsterdam, The Netherlands (1986); Bullock, G. R. et al., Techniques in Immunocytochemistry, Academic Press, Orlando, Fla. Vol. 1 (1982), Vol. 2 (1983), Vol. 3 (1985); Tijssen, P., Practice and Theory of Enzyme Immunoassays: Laboratory Techniques in Biochemistry and Molecular Biology, Elsevier Science Publishers, Amsterdam, The Netherlands (1985).

The test samples of the present invention include, but are not limited to, nucleic acid extracts, cells, and protein or membrane extracts from cells, which may be obtained from any bodily fluids (such as blood, urine, saliva, phlegm, gastric juices, etc.), cultured cells, biopsies, or other tissue preparations. The test sample used in the above-described methods will vary based on the assay format, nature of the detection method and the tissues, cells or extracts used as the sample to be assayed. Methods of preparing nucleic acid, protein, or cell extracts are well known in the art and can be readily be adapted in order to obtain a sample that is compatible with the system utilized.

Multicomponent integrated systems, such as microfluidic-based systems or "lab on a chip" systems, are an exemplary type of kit provided by the present invention for analyzing SNPs. Such systems miniaturize and compartmentalize processes such as PCR and capillary electrophoresis reactions in a single functional device. An example of such technique is disclosed in U.S. Pat. No. 5,589,136, which describes the integration of PCR amplification and capillary electrophoresis in chips.

Integrated systems can be envisaged mainly when microfluidic systems are used. These systems comprise a pattern of microchannels designed onto a glass, silicon, quartz, or plastic wafer included on a microchip. The movements of the samples are controlled by electric, electroosmotic or hydrostatic forces applied across different areas of the microchip to create functional microscopic valves and pumps with no moving parts. Varying the voltage controls the liquid flow at intersections between the micro-machined channels and changes the liquid flow rate for pumping across different sections of the microchip. In such a system, the containers/compartments of the kit may be embodied as chambers and/or channels of the microfluidic system.

For genotyping SNPs, the microfluidic system may integrate, for example, nucleic acid amplification, minisequencing primer extension, capillary electrophoresis, and a detection method such as laser induced fluorescence detection.

In a first step, the DNA samples are amplified, preferably by PCR. Then, the amplification products are subjected to automated minisequencing reactions using ddNTPs (specific fluorescence for each ddNTP) and the appropriate oligonucleotide minisequencing primers which hybridize just upstream of the targeted polymorphic base. Once the extension at the 3' end is completed, the primers are separated from the unincorporated fluorescent ddNTPs by capillary electrophoresis. The separation medium used in capillary electrophoresis can be, for example, polyacrylamide, polyethyleneglycol or dextran. The incorporated ddNTPs in the single nucleotide primer extension products are identified by laser-induced fluorescence detection. This microchip can be used to process at least 96 to 384 samples, or more, in parallel.

Vectors/Host Cells

The invention also provides vectors containing the SNP-containing nucleic acid molecules described herein. The term "vector" refers to a vehicle, preferably a nucleic acid molecule, that can transport the SNP-containing nucleic acid molecules. When the vector is a nucleic acid molecule, the SNP-containing nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the SNP-containing nucleic acid molecules. Alternatively, the vector may integrate into the host cell genome and produce additional copies of the SNP-containing nucleic acid molecules when the host cell replicates.

The invention provides vectors for the maintenance (cloning vectors) or vectors for expression (expression vectors) of the SNP-containing nucleic acid molecules. The vectors can function in procaryotic or eukaryotic cells or in both (shuttle vectors).

Expression vectors contain cis-acting regulatory regions that are operably linked in the vector to the SNP-containing nucleic acid molecules such that transcription of the SNP-containing nucleic acid molecules is allowed in a host cell. The SNP-containing nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the SNP-containing nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the SNP-containing nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., Molecular Cloning: A Laboratory Manual. 2nd. ed., Cold Spring Harbor Laboratory Press, Cold Spring Harbor, N.Y., (1989).

A variety of expression vectors can be used to express a SNP-containing nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, eg. cosmids and phagemids. Appropriate cloning and expression vectors for prokaryotic and eukaryotic hosts are described in Sambrook et al., Molecular Cloning: A Laboratory Manual. 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors that provide constitutive and inducible expression in prokaryotic and eukaryotic hosts are well known to those of ordinary skill in the art.

The SNP-containing nucleic acid molecules can be inserted into the vector nucleic acid by well-known methodology. Generally, the DNA sequence containing the SNP position that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the variant peptide as a fusion protein. Accordingly, the invention provides fusion vectors that allow for the production of the variant peptides. Fusion vectors can increase the expression of a recombinant protein, increase the (solubility of the recombinant protein, and aid in the purification of the protein by acting, for example, as a ligand for affinity purification. A proteolytic cleavage site may be introduced at the junction of the fusion moiety so that the desired variant peptide can ultimately be separated from the fusion moiety. Proteolytic enzymes include, but are not limited to, factor Xa, thrombin, and enterokinase. Typical fusion expression vectors include pGEX (Smith et al., Gene 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., Gene 69:301–315 (1988)) and pET 11d (Studier et al., Gene Expression Technology: Methods in Enzymology 185:60–89 (1990)).

Recombinant protein expression can be maximized in a host bacteria by providing a genetic background wherein the host cell has an impaired capacity to proteolytically cleave the recombinant protein. (Gottesman, S., Gene Expression Technology: Methods in Enzymology 185, Academic Press, San Diego, Calif. (1990)119–128). Alternatively, the sequence of the SNP-containing nucleic acid molecule of interest can be altered to provide preferential codon usage for a specific host cell, for example *E. coli*. (Wada et al., Nucleic Acids Res. 20:2111–2118 (1992)).

The SNP-containing nucleic acid molecules can also be expressed by expression vectors that are operative in yeast. Examples of vectors for expression in yeast e.g., *S. cerevisiae* include pYepSec1 (Baldari, et al., EMBO J. 6:229–234 (1987)), pMFa (Kurjan et al., Cell 30:933–943(1982)), pJRY88 (Schultz et al., Gene 54:113–123 (1987)), and pYES2 (Invitrogen Corporation, San Diego, Calif.).

The SNP-containing nucleic acid molecules can also be expressed in insect cells using, for example, baculovirus expression vectors. Baculovirus vectors available for expression of proteins in cultured insect cells (e.g., Sf9 cells) include the pAc series (Smith et al., Mol. Cell Biol. 3:2156–2165 (1983)) and the pVL series (Lucklow et al., Virology 170:31–39 (1989)).

In certain embodiments of the invention, the SNP-containing nucleic acid molecules described herein are expressed in mammalian cells using mammalian expression vectors. Examples of mammalian expression vectors include pCDM8 (Seed, B. Nature 329:840(1987)) and pMT2PC (Kaufman et al., EMBO J. 6:187–195 (1987)).

The expression vectors listed herein are provided by way of example only of the well-known vectors available to those of ordinary skill in the art that would be useful to express the SNP-containing nucleic acid molecules. The person of ordinary skill in the art would be aware of other vectors suitable for maintenance propagation or expression of the SNP-containing nucleic acid molecules described herein. These are found for example in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989.

The invention also encompasses vectors in which the SNP-containing nucleic acid sequences described herein are cloned into the vector in reverse orientation, but operably linked to a regulatory sequence that permits transcription of anti sense RNA. Thus, an antisense transcript can be produced to the SNP-containing nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction infection, lipofection, and other techniques such as those found in Sambrook, et al. (Molecular Cloning: A Laboratory Manual. 2nd, ed., Cold Spring Harbor Laboratory, Cold Spring Harbor Laboratory Press, Cold Spring Harbor, N.Y., 1989).

Host cells can contain more than one vector. Thus, different SNP-containing nucleotide sequences can be introduced on different vectors of the same cell. Similarly, the SNP-containing nucleic acid molecules can be introduced either alone or with other nucleic acid molecules that are not related to the SNP-containing nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the SNP-containing nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature variant proteins can be produced in bacteria, yeast, mammalian cells, and other cells under the control of the appropriate regulatory sequences, cell-free transcription and translation systems can also be used to produce these variant proteins using RNA derived from the DNA constructs described herein.

It is also understood that, depending upon the host cell in which recombinant production of the variant peptides described herein occurs, the variant peptides can have various glycosylation patterns, depending upon the cell, or maybe non-glycosylated as when produced in bacteria. In addition, the variant peptides may include an initial modified methionine in some cases as a result of a host-mediated process.

Uses of SNP Detection Reagents

SNP Genotyping

The process of determining which nucleotide(s) is/are present at one or more of the SNP positions disclosed in Table 1 and the Sequence Listing is referred to by such terms as SNP genotyping, SNP haplotyping, SNP typing, SNP scoring, SNP assaying, SNP profiling, SNP identification, and SNP screening. The invention provides methods for detecting which nucleotide is present at the SNP positions provided by the present invention, such as for use in screening for or treating a inflammatory and autoimmune disorders condition, or susceptibility thereto, associated with the SNPs of the present invention, or in genome mapping.

After a SNP position has been identified in a specific DNA sequence (as shown in Table 1 and the Sequence Listing), DNA samples can be genotyped to determine which allele is present at that SNP position. The neighboring sequence can be used to design a SNP detection reagent/kit. Preferred SNP genotyping methods include, but are not limited to, TaqMan, oligonucleotide arrays, and mass spectrometry (Mass Spec). Further, various primer extension strategies are known in the art and can be utilized in combination with Mass Spec or other approaches.

The TaqMan assay, also known as the 5' nuclease PCR assay, provides a sensitive and rapid means of genotyping SNPs. The TaqMan assay detects the accumulation of a specific amplified product during PCR. The TaqMan assay utilizes an oligonucleotide probe labeled with a fluorescent reporter dye at the 5' end of the probe and a quencher dye at the 3' end of the probe. The proximity of the quencher to the reporter in the intact probe maintains a reduced fluorescence for the reporter. During the PCR reaction, the 5' nuclease activity of DNA polymerase cleaves the probe, thereby separating the reporter dye and the quencher dye and resulting in increased fluorescence of the reporter. Accumulation of PCR product is detected directly by monitoring the increase in fluorescence of the reporter dye. The 5' nuclease activity of DNA polymerase cleaves the probe between the reporter and the quencher only if the probe hybridizes to the target and is amplified during PCR. The probe is designed to straddle a target SNP position and hybridize to the nucleic acid molecule only if a particular SNP allele is present.

Preferred TaqMan primer and probe sequences can readily be determined using the nucleic acid information provided herein. A number of computer programs, such as Primer-Express, can be readily used to obtain optimal primer/probe sets. It will be apparent to one of skill in the art that the primers and probes based on the nucleic acid information provided herein are useful as diagnostic probes or amplification primers for screening for SNPs of the present invention, and can be incorporated into a kit format.

Another method used for SNP typing is based on mass spectrometry. Mass spectrometry ("mass spec") takes advantage of the unique mass of each of the four nucleotides of DNA. SNPs can be unambiguously genotyped by mass spectrometry by measuring the differences in the mass of nucleic acids having alternate SNP alleles. MALDI-TOF (Matrix Assisted Laser Desorption Ionization-Time of Flight) mass spectrometry technology is preferred for extremely precise determinations of molecular mass, such as SNPs. Numerous approaches to SNP analysis have been developed based on mass spectrometry. A preferred mass spectrometry based method of SNP analysis is mini-sequencing primer extension, which can also be utilized in combination with other approaches, such as traditional gel-based formats and microarrays.

The mini-sequencing primer extension reaction involves designing and annealing a primer to a template PCR amplicon downstream from a target SNP position. A mix of dideoxynucleotide triphosphates (ddNTPs) and/or deoxynucleotide triphosphates (dNTPSs) are added to a reaction mixture containing PCR template, primer, and DNA polymerase. Extension of the primer terminates at the first position in the PCR template where a nucleotide complementary to one of the ddNTPs in the mix occurs. The primer can be either immediately 3' or several nucleotides removed from the SNP position. If the primer is several nucleotides removed from the target SNP, the only limitation is that the template sequence between the 3' end of the primer and the SNP position can not contain a nucleotide of the same type as the one to be detected, or this will cause premature termination of the extension primer. Alternatively, if all four ddNTPs alone, with no dNTPs, are added to the reaction mixture, the primer will always be extended by only one nucleotide, corresponding to the target SNP position. In this instance, primers are designed to bind one nucleotide downstream from the SNP position. Extension by only one nucleotide is preferable, as it minimizes the overall mass of the extended primer, thereby increasing the resolution of mass differences between alternative SNP nucleotides. Furthermore, mass-tagged dideoxynucleoside triphosphates (ddNTPs) can be employed in the primer extension reactions in place of unmodified ddNTPs. This increases the mass difference between primers extended with these ddNTPs, thereby providing increased sensitivity and accuracy, and is particularly useful for typing heterozygous base positions. Mass-tagging also alleviates the need for intensive sample-preparation procedures and decreases the necessary resolving power of the mass spectrometer.

The extended primers are then purified and analyzed by MALDI-TOF mass spectrometry to determine the identity of the nucleotide present at the SNP position. In one method of analysis, the products from the primer extension reaction are combined with light absorbing crystals that form a matrix. The matrix is then hit with an energy source such as a laser to ionize and desorb the nucleic acid molecules into the gas-phase. The ionized molecules are then ejected into a flight tube and accelerated down the tube towards a detector. The time between the ionization event, such as a laser pulse, and collision of the molecule with the detector is the time of flight of that molecule. The time of flight is precisely correlated with the mass-to-charge ratio (m/z) of the ionized molecule. Ions with smaller mass-to-charge ratios travel down the tube faster than ions with larger m/z and therefore the lighter ions reach the detector before the heavier ions. The time-of-flight is then converted into a corresponding, and highly precise, m/z. In this manner, SNPs can be identified based on the slight differences in mass, and the corresponding time of flight differences, inherent in nucleic acid molecules having different nucleotides at a single base position.

SNPs can also be scored by direct DNA sequencing. A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Further examples of methods that can be used to screen for the SNPs of the present invention include single-strand conformational polymorphism (SSCP), and denaturing gradient gel electrophoresis (DGGE) (Myers et al., *Nature* 313:495 (1985)). SSCP identifies base differences by alteration in electrophoretic migration of single stranded PCR products, as described in Orita et al., *Proc. Nat. Acad.* Single stranded PCR products can be generated by heating or otherwise denaturing double stranded PCR products. Single-stranded nucleic acids may refold or form secondary structures that are partially dependent on the base sequence. The different electrophoretic mobilities of single-stranded amplification products are related to base-sequence differences at SNP positions. DGGE differentiates SNP alleles based on the different sequence-dependent stabilities and melting properties inherent in polymorphic DNA and the corresponding differences in electrophoretic migration patterns in a denaturing gradient gel. (Erlich, ed., PCR Technology, Principles and Applications for DNA Amplification, (W.H. Freeman and Co, New York, 1992), Chapter 7).

Sequence-specific ribozymes (U.S. Pat. No. 5,498,531) can be used to score SNPs based on the development or loss of a ribozyme cleavage site. Perfectly matched sequences can be distinguished from mismatched sequences by nuclease cleavage digestion assays or by differences in melting temperature. If the SNP affects a restriction enzyme cleavage site, the SNP can be identified by alterations in restriction enzyme digestion patterns, and the corresponding changes in nucleic acid fragment lengths determined by gel electrophoresis In scoring SNPs, genomic DNA can be analyzed directly or can be amplified using PCR prior to analysis. RNA or cDNA can be used in the same way. In some uses, detection of the SNP involves the use of a probe/primer in a polymerase chain reaction (PCR) (see, e.g. U.S. Pat. Nos. 4,683,195 and 4,683,202) or ligase chain reaction (LCR) (see, e.g., Landegran et al., *Science* 241:1077–1080 (1988); Nakazawa et al., *PNAS* 91:360–364 (1994); and Abravaya et al., *Nucleic Acids Res.* 23:675–682 (1995); Barany, F., *Proc. Natl. Acad. Sci.* (U.S.A.) 88, 189–193 (1991)). Southern and Northern blot analysis can also be utilized for nucleic acid analysis.

SNP genotyping can include the steps of collecting a sample of cells from a patient, isolating nucleic acid (e.g., genomic, mRNA or both) from the cells of the sample, contacting the nucleic acid sample with one or more primers which specifically hybridize to a region of the isolated nucleic acid containing a target SNP under conditions such that hybridization and amplification of the gene occurs, and determining the nucleotide present at the SNP position, or, in some instances, detecting the presence or absence of an amplification product.

SNP Genotyping and Association

Association, or correlation, of particular SNP genotypes with a particular phenotype is performed for a population of individuals who have been tested for the presence or absence of a phenotypic trait of interest and for SNP marker sets (e.g., one or more of the SNPs disclosed in Table 1 and the Sequence Listing). To perform such analysis, the presence or absence of a set of polymorphisms (i.e. a polymorphic set) is determined for a set of the individuals, some of whom exhibit a particular trait, and some of whom exhibit lack of the trait. The alleles of each polymorphism of the set are then reviewed to determine whether the presence or absence of a particular allele is associated with the trait of interest. Correlation can be performed by standard statistical methods such as a chi-squared test and statistically significant correlations between polymorphic form(s) and phenotypic characteristics are noted. For example, it might be found that the presence of allele A1 at SNP position A correlates with heart disease. As a further example, it might be found that the combined presence of allele A1 at SNP position A and allele B1 at SNP position B correlates with increased susceptibility to inflammatory and autoimmune disorders.

Such correlation can be exploited in several ways. For example, in the case of a strong correlation between a set of one or more polymorphic forms and a disease for which treatment is available, detection of the polymorphic form set in a patient may justify immediate administration of treatment, or at least the institution of regular monitoring of the patient. Detection of a polymorphic form correlated with serious disease in a couple contemplating a family may also be valuable to the couple in their reproductive decisions. For example, the female partner might elect to undergo in vitro fertilization to avoid the possibility of transmitting such a polymorphism from her husband to her offspring. In the case of a weaker, but still statistically significant correlation between a polymorphic set and human disease, immediate therapeutic intervention or monitoring may not be justified. Nevertheless, the patient can be motivated to begin simple life-style changes (e.g., diet, exercise) that can be accomplished at little cost to the patient but confer potential benefits in reducing the risk of conditions to which the patient may have increased susceptibility by virtue of variant alleles.

Uses of SNP Genotypes

After determining which alleles are present in an individual at one or more SNP positions, or which alleles are present at one or more SNP positions in many individuals of a population, this information can be used in a number of methods, as described below. Examples of such methods include disease susceptibility screening, disease diagnosis, individualizing drug therapy based on an individual's genotype ("pharmacogenomics"), developing drugs based on a greater understanding of SNPs associated with a disease, human identification applications such as forensics, and grouping SNPs into haplotype groups.

For example, the SNP information provided by the present invention, particularly the mapping of each SNP to a precise nucleotide position in the human genome, provides the basis for haplotyping projects. For example, the information provided herein enables the SNPs of the present invention to be readily genotyped in multiple individuals, who may optionally represent diverse racial/ethnic groups, in order to classify groups of SNPs that are generally inherited together into haplotypes. Such haplotypes can further be studied for correlations with diseases or other phenotypic effects. See, for example, Stephens et al. (*Science* 293, 489–493, 20 Jul. 2001) for further information regarding SNP haplotypes.

Disease Susceptibility Screening/Diagnosis

The polymorphisms of the invention may contribute to the phenotype, for example, a disease condition such as inflammatory and autoimmune disorders, of an individual in different ways. Some polymorphisms occur within a protein coding sequence and contribute to phenotype by affecting protein structure. Other polymorphisms occur in noncoding regions but may exert phenotypic effects indirectly via influence on replication, transcription, and translation. A single polymorphism may affect more than one phenotypic trait. Likewise, a single phenotypic trait may be affected by polymorphisms in different genes.

The contribution or association of particular SNPs with disease phenotypes, such as inflammatory and autoimmune disorders, enables the SNPs of the present invention to be used to develop superior diagnostic tests capable of identifying individuals who express a detectable trait, such as inflammatory and autoimmune disorders, as the result of a specific genotype or a individuals whose genotype places them at risk of developing a detectable trait at a subsequent time. As described herein, the diagnostics may be based on a single SNP or a group of SNPs. Combined detection of a plurality of SNPs (for example, 2, 5, 10, 20 or more of the SNPs provided in Table 1 and the Sequence Listing) typically increases the probability of an accurate diagnosis. For example, the presence of a single polymorphic form known to correlate with inflammatory and autoimmune disorders might indicate a probability of 20% that an individual has or is susceptible to inflammatory and autoimmune disorders, whereas detection of five polymorphic forms, each of which correlates with inflammatory and autoimmune disorders, might indicate a probability of 80% that an individual has or is susceptible to inflammatory and autoimmune disorders. To further increase the accuracy of diagnosis or susceptibility screening, analysis of the SNPs of the present invention can be combined with that of other polymorphisms or other risk factors of inflammatory and autoimmune disorders, such as family history, diet, or lifestyle factors.

It will of course be understood by practitioners skilled in the treatment or diagnosis of inflammatory and autoimmune disorders that the present invention does not intend to provide an absolute identification of individuals who could be at risk of developing a particular disease such as inflammatory and autoimmune disorders and disorders related to inflammatory and autoimmune disorders but rather to indicate a certain degree or likelihood of developing a disease. However, this information is extremely valuable as it can, in certain circumstances, be used to initiate preventive treatments or to allow an individual carrying a significant haplotype to foresee warning signs such as minor symptoms. In diseases in which attacks may be extremely violent and sometimes fatal if not treated on time, the knowledge of a potential predisposition, even if this predisposition is not absolute, might contribute in a very significant manner to treatment efficacy.

The diagnostic techniques of the present invention may employ a variety of methodologies to determine whether a test subject has a SNP pattern associated with an increased risk of developing a detectable trait or whether the individual suffers from a detectable trait as a result of a particular mutation, including methods which enable the analysis of individual chromosomes for haplotyping, such as family studies, single sperm DNA analysis or somatic hybrids. The trait analyzed using the present diagnostics may be any detectable trait, including pathologies and disorders related to inflammatory and autoimmune disorders.

Another aspect of the present invention relates to a method of determining whether an individual is at risk of developing a trait or whether an individual expresses a trait as a consequence of possessing a particular trait-causing allele. The present invention relates to a method of determining whether an individual is at risk of developing a plurality of traits or whether an individual expresses a plurality of traits as a result of possessing a particular trait causing allele. These methods involve obtaining a nucleic acid sample from the individual and determining whether the nucleic acid sample contains one or more alleles of one or more SNPs indicative of a risk of developing the trait or indicative that the individual expresses the trait as a result of possessing a particular trait-causing allele.

In another embodiment, the agents of the present invention are used to determine whether an individual has a SNP affecting the level (i.e., the concentration of mRNA or protein in a sample, etc.) or pattern (i.e., the kinetics of expression, rate of decomposition, stability profile, Km, Vmax, etc.) of gene expression (collectively, the "gene response" of a cell or bodily fluid) (for example, a SNP in a gene, or in a regulatory region(s) or other gene(s) that control or affect the expression of the gene). Such an analysis of gene expression can be conducted by screening for mRNA corresponding to the SNP-containing gene or variant pep tides encoded thereby.

Therapies/Pharmacogenomics/Drug Development

The invention provides methods for assessing the pharmacogenomic susceptibility of a subject harboring a particular SNP, or SNP haplotype, of the present invention to a particular pharmaceutical compound, or to a class of such compounds. Pharmacogenomics deals with clinically significant hereditary variations, such as SNPs, in the response to drugs due to altered drug disposition and abnormal action in affected persons. See, e.g., Roses, *Nature* 405, 857–865 (2000); Gould Rothberg, *Nature Biotechnology* 19, 209–211 (2001); Eichelbaum, *Clin. Exp. Pharmacol. Physiol.* 23(1011):983–985 (1996); and Linder, *Clin. Chem.* 43(2):254266 (1997). The clinical outcomes of these variations result in severe toxicity of therapeutic drugs in certain individuals or therapeutic failure of drugs in certain individuals as a result of individual variation in metabolism. Thus, the SNP genotype of an individual can determine the way a therapeutic compound acts on the body or the way the body metabolizes the compound. Further, the activity of drug metabolizing enzymes affects both the intensity and duration of drug action.

The discovery of SNPs in drug metabolizing enzymes, drug transporters, proteins for pharmaceutical agents, and other drug targets has explained why some patients do not obtain the expected drug effects, show an exaggerated drug effect, or experience serious toxicity from standard drug dosages. SNPs can be expressed in the phenotype of the extensive metabolizer and in the phenotype of the poor metabolizer. Accordingly, SNPs may lead to allelic protein variants of a protein in which one or more of the protein functions in one population is different from those in another population. The SNPs and corresponding variant peptides thus provide a target to ascertain a genetic predisposition that can affect treatment modality. Thus, in a ligand-based treatment, SNPs may give rise to amino terminal extracellular domains and/or other ligand-binding regions that are more or less active in ligand binding, and protein activation. Accordingly, ligand dosage would necessarily be modified to maximize the therapeutic effect within a given population containing a SNP/haplotype. As an alternative to genotyping, specific variant peptides containing variant amino acids encoded by the SNPs could be identified. Thus, pharmacogenomic characterization of an individual permits the selection of effective compounds and effective dosages of such compounds for prophylactic or therapeutic treatment based on the individual's SNP genotype, thereby enhancing and optimizing the therapeutic effectiveness of the therapy. Furthermore, the production of recombinant cells and transgenic animals containing these SNPs/haplotypes allow effective clinical design of treatment compounds and dosage regimens. For example, transgenic animals can be produced that differ only in specific SNP alleles in a gene that is orthologous to a human disease susceptibility gene.

Pharmacogenomic uses of the SNPs of the present invention provide several significant advantages for patient care, particularly in treating inflammatory and autoimmune disorders. Pharmacogenomic characterization of an individual, based on an individual's SNP genotype, identifies those individuals unlikely to respond to treatment with a particular medication and thereby allows doctors to avoid prescribing the medication to those individuals. SNP genotyping of an individual thereby enables doctors to select the appropriate medication and dosage regimen that will be most effective based on an individual's SNP genotype. This increases doctor's confidence in prescribing medications and motivates patients to comply with their drug regimens. Furthermore, pharmacogenomics will identify patients predisposed to toxicity and adverse reactions to particular drugs or drug dosages. Adverse drug reactions lead to more than 100,000 avoidable deaths per year in the United States alone and therefore represent a significant cause of hospitalization and death, as well as a significant economic burden on the healthcare system (Pfost et. al., *Trends in Biotechnology*, August 2000.). Thus pharmacogenomics has the potential to both save lives and reduce costs substantially.

A subject suffering from a pathological condition, such as inflammatory and autoimmune disorders, ascribed to a SNP may be treated so as to correct the genetic defect. (See Kren et al., *Proc. Natl. Acad. Sci. USA* 96:10349–10354 (1999)). Such a subject is identified by any method that can detect the polymorphism in a sample drawn from the subject. Such a genetic defect may be permanently corrected by administering to such a subject a nucleic acid fragment incorporating a repair sequence that supplies the wild-type nucleotide at the position of the SNP. This site-specific repair sequence encompasses an RNA/DNA oligonucleotide which operates to promote endogenous repair of a subject's genomic DNA. The site-specific repair sequence is administered in an appropriate vehicle, such as a complex with polyethylenimine, encapsulated in anionic liposomes, a viral vector such as an adenovirus, or other pharmaceutical composition that promotes intracellular uptake of the administered nucleic acid. A genetic defect leading to an inborn pathology may then be overcome, as the chimeric oligonucleotides induces incorporation of the wild type sequence into the subject's genome. Upon incorporation, the wild type gene product is expressed, and the replacement is propagated, thereby engendering a permanent repair and therapeutic enhancement of the clinical condition of the subject.

In cases in which a cSNP leads to a variant protein that is ascribed to be the cause of, or a contributing factor to, a pathological condition, a method of treating such a condition includes administering to a subject experiencing the pathology the wild type cognate of the variant protein. Once administered in an effective dosing regimen, the wild type cognate provides complementation or remediation of the pathological condition.

The invention further provides a method for identifying a compound that can be used to treat a disorder associated with expression of a variant gene, such as inflammatory and autoimmune disorders. The method typically includes assaying the ability of the compound to modulate the activity and/or expression of the SNP-containing nucleic acid and thus identifying a compound that can be used to treat a disorder characterized by undesired activity or expression of the SNP-containing nucleic acid. The assays can be performed in cell-based and cell-free systems. Cell-based assays include cells naturally expressing the SNP-containing nucleic acid molecule or recombinant cells genetically engineered to express the SNP-containing nucleic acid sequences.

The assay for variant nucleic acid expression can involve direct assay of nucleic acid levels, such as mRNA levels, or on collateral compounds involved in the signal pathway. Further, the expression of genes that are up- or down regulated in response to the variant protein signal pathway can also be assayed. In this embodiment the regulatory regions of these genes can be operably linked to a reporter gene such as luciferase.

Thus, modulators of variant gene expression can be identified in a method wherein a cell is contacted with a candidate compound and the expression of mRNA determined. The level of expression of variant mRNA in the presence of the candidate compound is compared to the level of expression of variant mRNA in the absence of the candidate compound. The candidate compound can then be identified as a modulator of SNP-containing nucleic acid expression based on this comparison and be used, for example to treat a disorder characterized by expression of the SNP-containing nucleic acid, such as inflammatory and autoimmune disorders. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the SNP as a target, using a compound identified through drug screening as a gene modulator to modulate variant nucleic acid expression. Modulation includes both up-regulation (i.e. activation or agonization) or down-regulation (suppression or antagonization) of nucleic acid expression. Alternatively, a modulator of variant nucleic acid expression can be a small molecule or drug identified using the screening assays described herein as long as the drug or small molecule modulates the expression of variant nucleic acid.

Expression of proteins, either wild type or variant, may be altered in individuals with a particular SNP allele in a control element, such as a promoter, that regulates expression. In this situation, methods of treatment and compounds are identified, as discussed herein, that regulate or overcome the variant control element, thereby generating normal, or healthy, expression levels of either the wild type or variant protein.

The SNP-containing nucleic acid molecules are useful for monitoring the effectiveness of modulating compounds on the expression or activity of the variant gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

According to another aspect of the present invention, there is provided a pharmaceutical pack comprising a drug and a set of instructions for administration of the drug to humans diagnostically tested for one or more SNPs provided by the present invention.

The SNPs of the present invention are useful for improving the process of drug development. Individuals can be selected for clinical trials based on their SNP genotype. Individuals with SNP genotypes that indicate that they are most likely to respond to the drug can be included in the trials and those individuals whose SNP genotypes indicate that they would not respond to the drug, or suffer adverse reactions, can be eliminated from the clinical trials. This not only improves the safety of clinical trials, but also will enhance the chances that the trial will demonstrate statistically significant efficacy. Furthermore, the SNPs of the present invention may help explain why certain, previously developed drugs performed poorly in clinical trials and may help identify a subset of the population that would benefit from a drug that had previously performed poorly in clinical trials, thereby "rescuing" previously developed drugs.

Human Identification

In addition to their value related to inflammatory and autoimmune disorders and associated pathologies, the SNPs provided by the present invention are also valuable as human identification markers for such applications as forensics and paternity testing. Genetic variations in the nucleic acid sequences between individuals can be used as genetic markers to identify individuals and to associate a biological sample with an individual. Determination of which nucleotides occupy a set of SNP positions in an individual identifies a set of SNP markers that distinguishes the individual. The more SNP positions that are analyzed, the lower the probability that the set of SNPs in one individual is the same as that in an unrelated individual. Preferably, if multiple sites are analyzed, the sites are unlinked. Thus, SNPs of the invention may be used in conjunction with polymorphisms in distal genomic regions.

SNPs have numerous advantages over other types of polymorphic markers, such as short tandem repeats (STRs), and therefore SNPs are the preferred markers for forensic and human identification applications. SNPs can be easily scored and are amenable to automation, making SNPs the markers of choice for large-scale forensic databases. SNPs are found in much greater abundance throughout the genome than repeat polymorphisms. Population frequencies of two polymorphic forms can usually be determined with greater accuracy than those of multiple polymorphic forms at multi-allelic loci. SNPs are mutationaly more stable than repeat polymorphisms. SNPs are not susceptible to artifacts such as stutter bands that can hinder analysis. Stutter bands are frequently encountered when analyzing repeat polymorphisms, and are particularly troublesome when analyzing samples such as crime scene samples that may contain mixtures of DNA from multiple sources. Another significant advantage of SNP markers over STR markers is the much shorter length of nucleic acid needed to score a SNP. For example, STR markers are generally several hundred base pairs in length. SNPs, on the other hand, comprise a single base pair, and generally a short conserved region on either side of the SNP position for primer and/or probe binding. This makes SNPs more amenable to typing in highly degraded or aged biological samples that are frequently encountered in forensic casework in which DNA may be fragmented into short pieces. SNPs also are not subject to microvariant and "off-ladder" alleles frequently encountered when analyzing STR loci. Microvariants are deletions or insertions within a repeat unit that change the size of the amplified DNA product so that the amplified product does not migrate at the same rate as reference alleles with normal sized repeat units. When separated by size, such as by electrophoresis on a polyacrylamide gel, microvariants do not align with a reference allelic ladder of standard sized repeat units, but rather migrate between the reference alleles. The reference allelic ladder is used for precise sizing of alleles for allele classification; therefore alleles that do not align with the reference allelic ladder lead to substantial analysis problems. Furthermore, when analyzing multi-allelic repeat polymorphisms, occasionally an allele is found that consists of more or less repeat units that has been previously seen in the population. These alleles will migrate outside the size range of known alleles in a reference allelic ladder, and therefore are referred to as "off-ladder" alleles. In extreme cases, the allele may contain so few or so many repeats that it migrates well out of the range of the reference allelic ladder. In this situation, the allele may not even be observed, or, with multiplex analysis, it may migrate within or close to the size range for another locus, further confounding analysis. SNP analysis avoids the problems of microvariants and off-ladder alleles encountered in STR analysis. Importantly, microvariants and off-ladder alleles may provide significant problems, and may be completely missed, when using analysis methods such as oligonucleotide hybridization arrays, which utilize oligonucleotide probes specific for certain known alleles. Furthermore, off-ladder alleles and microvariants encountered with STR analysis, even when correctly typed, may lead to improper statistical analysis, since their frequencies in the population are generally unknown or poorly characterized, thereby the statistical significance of a matching genotype may be questionable. All these advantages are considerable in light of the consequences of most DNA identification cases, which may lead to life imprisonment for an individual, or re-association of remains to the family of a deceased individual.

DNA can be isolated from biological samples such as blood, bone, hair, saliva, and semen and compared with the DNA from a reference source at particular SNP positions. Multiple SNP markers can be assayed simultaneously in order to increase the power of discrimination and the statistical significance of a matching genotype. For example, oligonucleotide arrays can be used to genotype a large number of SNPs simultaneously. The SNPs provided by the present invention can be assayed in combination with other polymorphic genetic markers, such as other SNPs or short tandem repeats (STRs), in order to identify an individual or to associate an individual with a particular biological sample.

Furthermore, the SNPs provided by the present invention can be typed for inclusion in a database of DNA genotypes, for example a criminal DNA databank. A genotype obtained from a biological sample of unknown source can then be queried against the database to find a matching genotype, with the SNPs of the present invention providing nucleotide positions at which to compare the known and unknown DNA sequences for identity.

SNPs of the present invention can also be assayed for use in paternity testing. The object of paternity testing is usually to determine whether a male is the father of a child. In most cases, the mother of the child is known and thus, the mother's contribution to the child's genotype can be traced. Paternity testing investigates whether the part of the child's genotype not attributable to the mother is consistent with that of the putative father. Paternity testing can be performed by analyzing sets of polymorphisms in the putative father and the child. If the set of polymorphisms in the child attributable to the father does not match the set of polymorphisms of the putative father, it can be concluded, barring experimental error, that the putative father is not the real father. If the set of polymorphisms in the child attributable to the father does match the set of polymorphisms of the putative father, a statistical calculation can be performed to determine the probability of coincidental match.

The uses of the SNPs of the present invention for human identification extends to various authentication systems, commonly referred to as biometric systems. Biometric systems convert physical characteristics of humans (or other organisms) into digital data for precise quantification. Biometric systems include various technological devices that measure such unique anatomical or physiological characteristics as finger, thumb, or palm prints; hand geometry, vein patterning on the back of the hand; blood vessel patterning of the retina and color and texture of the iris; facial characteristics; voice patterns; signature and typing dynamics; and DNA. Such physiological measurements can be used to verify identity and restrict or allow access based on the identification. Examples of applications for biometrics include physical area security, computer and network security, aircraft passenger check-in and boarding, financial transactions, medical records access, government benefit distribution, voting, law enforcement, passports, visas and immigration, prisons, various military applications, and for restricting access to expensive or dangerous items, such as automobiles or guns. For a further review of biometric systems, see O'Connor, *Stanford Technology Law Review*. For an exemplary biometric system, see U.S. Pat. No. 6,119,096, Mann et al., which covers iris recognition for aircraft passenger check-in and boarding security. Large collections of SNPs, particularly the SNPs provided by the present invention, can be typed to uniquely identify an individual for biometric applications such as those described above. Such SNP typing can readily be accomplished using DNA chips as described above. Preferably, a minimally invasive means for obtaining a DNA sample is utilized. For example, PCR amplification enables sufficient DNA for analysis to be obtained from fingerprints, which contain DNA-containing skin cells and oils that are naturally transferred during contact.

Variant Protein/Peptide Uses

The variant proteins of the present invention can be used in assays to determine the biological activity of the variant protein, including in a panel of multiple proteins for high-throughput screening; to raise antibodies or to elicit another immune response; as a reagent (including the labeled reagent) in assays designed to quantitatively determine levels of the variant protein (or its binding partner or protein) in biological fluids; and as markers for tissues in which the corresponding variant protein is preferentially expressed (either constitutively or at a particular stage of tissue differentiation or development or in a disease state). Any or all of these research utilities are capable of being developed into reagent grade or kit format for commercialization as research products. Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The variant proteins of the present invention provide a target for diagnosing a disease or predisposition to disease mediated by a variant inflammatory and autoimmune disorders associated gene/protein. Accordingly, the invention provides methods for detecting the presence, or levels of, the variants of the present invention (or encoding nucleic acid) in a cell, tissue, or organism. The method involves contacting a biological sample with a compound capable of interacting with the variant protein (or SNP-containing gene or mRNA encoding the variant protein) such that the interaction can be detected. The variant protein can be isolated from a biological sample and assayed for the presence of a variant amino acid encoded by a nucleic acid containing a SNP disclosed by the present invention that results in aberrant protein activity. SNPs and corresponding amino acid variations are provided in Table 1 and the Sequence Listing. The SNPs may result in changes to the protein and the corresponding protein activity, such as through non-synonymous substitutions in protein coding regions, formation of non-sense mutations, or by altering control elements such as promoters. Analytic methods of detecting amino acid variants include altered electrophoretic mobility, altered tryptic peptide digest, altered protein activity in cell-based or cell-free assay, alteration in ligand or antibody-binding pattern, altered isoelectric point, direct amino acid sequencing, and any other of the known assay techniques useful for detecting mutations in a protein.

One agent for detecting a variant protein in a sample is an antibody capable of selectively binding to a variant form of the protein. Such samples include tissues, cells, and biological fluids isolated from a subject, as well as tissues, cells and fluids present within a subject.

In vitro techniques for detection of the specific allelic variants of the inflammatory and autoimmune disorders associated protein, and fragments thereof, disclosed herein include enzyme linked immunosorbent assays (ELISAs), Western blots, immunoprecipitations and immunofluorescence. Alternatively, the variant peptide can be detected in vivo in a subject by introducing into the subject a labeled antibody to the variant peptide. For example, the antibody can be labeled with a radioactive marker whose presence and location in a subject can be detected by standard imaging techniques.

The variant proteins of the present invention are also useful for biological assays. Such assays involve any of the known functions or activities or properties useful for the diagnosis and treatment of inflammatory and autoimmune disorders and associated conditions.

The variant proteins of the present invention are also useful in drug screening assays, in cell-based or cell-free systems. Cell-based systems can be native, i.e., cells that normally express the protein, as a biopsy or expanded in cell culture. In one embodiment, however, cell-based assays involve recombinant host cells expressing the variant protein. Cell-free assays can be used to detect the ability of a compound to directly bind to a variant protein or the corresponding SNP-containing nucleic acid fragment.

The variant proteins of the present invention can be used to identify compounds that modulate protein activity. Both the variant protein of the present invention and appropriate fragments can be used in high-throughput screens to assay candidate compounds for the ability to bind and/or modulate the activity of the variant protein. These compounds can be further screened against a functional, or a non-variant, protein to determine the effect of the compound on the protein activity. Further, these compounds can be tested in animal or invertebrate systems to determine activity/effectiveness. Compounds can be identified that activate (agonist) or inactivate (antagonist) the variant protein to a desired degree.

Further, the variant protein polypeptides can be used to screen a compound for the ability to stimulate or inhibit interaction between the variant protein and a target molecule that normally interacts with the protein. The target can be a ligand or a binding partner that the protein normally interacts with (for example, epinephrine or norepinephrine). Such assays typically include the steps of combining the variant protein with a candidate compound under conditions that allow the variant protein, or fragment, to interact with the target molecule, and to detect the formation of a complex between the protein and the target or to detect the biochemical consequence of the interaction with the variant protein and the target, such as any of the associated effects of signal transduction.

Candidate compounds include, for example, 1) peptides such as soluble peptides, including Ig-tailed fusion peptides and members of random peptide libraries (see, e.g., Lam et al., Nature 354:82–84 (1991); Houghten et al., Nature 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the variant protein that competes for ligand binding. Other candidate compounds include mutant proteins or appropriate fragments containing mutations that affect variant protein function and thus compete for ligand. Accordingly, a fragment that competes for ligand, for example with a higher affinity, or a fragment that binds ligand but does not allow release, is encompassed by the invention.

The invention further includes other end point assays to identify compounds that modulate (stimulate or inhibit) variant protein activity. The assays typically involve an assay of events in the signal transduction pathway that indicate protein activity. Thus, the expression of genes that are up or down-regulated in response to the variant protein dependent signal cascade can be assayed. In one embodiment, the regulatory region of such genes can be operably linked to a marker that is easily detectable, such as luciferase. Alternatively, phosphorylation of the variant protein, or a variant protein target, could also be measured. Any of the biological or biochemical functions mediated by the variant protein can be used as an endpoint assay. These include all of the biochemical or biological events described herein, in the references cited herein, incorporated by reference for these endpoint assay targets, and other functions known to those of ordinary skill in the art.

The variant protein polypeptides are also useful in competition binding assays in methods designed to discover compounds that interact with the variant protein. Thus, a compound is exposed to a variant protein polypeptide under conditions that allow the compound to bind or to otherwise interact with the variant polypeptide. Ligands to the variant protein are also added to the mixture. If the test compound interacts with the variant protein or ligand, it decreases the amount of complex formed or activity from the variant protein target. This type of assay is particularly useful in cases in which compounds are sought that interact with specific regions of the variant protein. See Hodgson, Bio/technology, 1992, September 10(9), 973–80 for a review of competition binding assays and other receptor screening assays.

To perform cell free drug screening assays, it is sometimes desirable to immobilize either the variant protein, or fragment, or its target molecule to facilitate separation of complexes from uncomplexed forms of one or both of the proteins, as well as to accommodate automation of the assay.

Techniques for immobilizing variant proteins on matrices can be used in drug screening assays. In one embodiment, a fusion protein can be provided which adds a domain that allows the protein to be bound to a matrix. For example, glutathione-S-transferase/I125 fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and a candidate compound, such as a drug candidate, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of protein-binding protein found in the bead fraction quantitated from the gel using standard electrophoretic techniques. For example, either the variant polypeptide or its target molecule can be immobilized utilizing conjugation of biotin and streptavidin using techniques well known in the art. Alternatively, antibodies reactive with the variant protein but which do not interfere with binding of the variant protein to its target molecule can be derivatized to the wells of the plate, and the variant protein trapped in the wells by antibody conjugation. Preparations of a protein-binding protein and a candidate compound are incubated in the variant protein-presenting wells and the amount of complex trapped in the well can be quantitated. Methods for detecting such complexes, in addition to those described above for the GST-immobilized complexes, include immunodetection of complexes using antibodies reactive with the protein target molecule, or which are reactive with variant protein and compete with the target molecule, as well as enzyme-linked assays that rely on detecting an enzymatic activity associated with the target molecule.

Agents that modulate the variant protein of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of variant protein activity identified according to these drug screening assays can be used to treat a subject with a disorder mediated by the protein pathway, such as inflammatory and autoimmune disorders, by treating cells that express the variant protein. These methods of treatment include the steps of administering the modulators of protein activity in a pharmaceutical composition as described herein, to a subject in need of such treatment.

This invention further pertains to novel agents identified by the above-described screening assays. Accordingly, it is within the scope of this invention to further use an agent identified as described herein in an appropriate animal model. For example, an agent identified as described herein (e.g., a variant modulating agent, a variant antisense nucleic acid molecule, a variant inflammatory and autoimmune disorders associated protein-specific antibody, or a variant inflammatory and autoimmune disorders associated protein-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

Antibody Uses

The antibodies can be used to isolate the variant proteins of the present invention by standard techniques, such as affinity chromatography or immunoprecipitation. The antibodies can facilitate the purification of the natural variant protein from cells and recombinantly produced variant protein expressed in host cells. In addition, such antibodies are useful for detecting the presence of the variant protein of the present invention in cells or tissues to determine the pattern of expression of the variant protein among various tissues in an organism and over the course of normal development or disease progression. Further, such antibodies can be used to detect variant protein in situ, in vitro, or in a cell lysate or supernatant in order to evaluate the abundance and pattern of expression. Also, such antibodies can be used to assess abnormal tissue distribution, abnormal expression during development, or expression in an abnormal condition, such as inflammatory and autoimmune disorders. Antibody detection of circulating fragments of the full length variant protein can be used to identify turnover.

Antibodies to the variant proteins of the present invention are useful in pharmacogenomic analysis. Thus, antibodies prepared against variant proteins encoded by the SNPs of the present invention can be used to identify individuals that require modified treatment modalities.

Further, the antibodies can be used to assess expression of the variant protein in disease states such as in active stages of the disease or in an individual with a predisposition toward disease related to the protein's function, particularly inflammatory and autoimmune disorders. Antibodies specific for a variant protein, encoded by a SNP of the present invention, can be used to assay for the presence of the variant protein, such as to screen for susceptibility to a disease associated with the presence of the variant protein, such as inflammatory and autoimmune disorders.

The antibodies are also useful as an immunological marker for variant protein analyzed by electrophoretic mobility, isoelectric point, tryptic peptide digest, and other physical assays known to those in the art.

The antibodies can also be used to assess aberrant subcellular localization of the variant protein in cells in various tissues. The diagnostic uses can be applied, not only in genetic testing, but also in monitoring a treatment modality. Accordingly, where treatment is ultimately aimed at correcting the expression level or the presence of variant protein or aberrant tissue distribution or developmental expression of the variant protein, antibodies directed against the variant protein or relevant fragments can be used to monitor therapeutic efficacy.

The antibodies are also useful for inhibiting variant protein function, for example, blocking the binding of the variant protein to a binding partner such as epinephrine or norepinephrine. These uses can also be applied in a therapeutic context in which treatment involves inhibiting the variant protein's function. An antibody can be used, for example, to block binding, thus modulating (agonizing or antagonizing) the variant peptides activity. Antibodies can be prepared against specific fragments containing sites required for function or against intact variant protein that is associated with a cell or cell membrane.

The invention also encompasses kits for using antibodies to detect the presence of a variant protein in a biological sample. The kit can comprise antibodies such as a labeled or labelable antibody and a compound or agent for detecting variant protein in a biological sample; means for determining the amount of variant protein in the sample; means for comparing the amount of variant protein in the sample with a standard; and instructions for use.

Uses of Vectors and Host Cells

The recombinant host cells expressing the variant peptides described herein have a variety of uses. First, the cells are useful for producing a variant protein or peptide that can be further purified to produce desired amounts of variant protein or fragments. Thus, host cells containing expression vectors are useful for variant peptide production.

Host cells are also useful for conducting cell-based assays involving the variant protein or variant protein fragments, such as those described above as well as other formats known in the art. Thus, a recombinant host cell expressing a variant protein is useful for assaying compounds that stimulate or inhibit variant protein function which may not be apparent by their effect on the native variant protein. Recombinant host cells are also useful for assaying functional alterations in the variant proteins compared with normal function.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA containing a SNP of the present invention which is integrated into the genome of a cell from which a transgenic animal develops and which remains in the genome of the mature animal in one or more cell types or tissues of the transgenic animal. These animals are useful for studying the function of a variant protein and identifying and evaluating modulators of variant protein activity. Other examples of transgenic animals include non-human primates, sheep, dogs, cows, goats, chickens, and amphibians.

A transgenic animal can be produced by introducing SNP-containing nucleic acid into the male pronuclei of a fertilized oocyte, e.g., by microinjection, retroviral infection, and allowing the oocyte to develop in a pseudopregnant female foster animal. Any protein nucleotide sequences that contain a SNP of the present invention can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the variant protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. PNAS 89:6232–6236 (1992). Another example of a. recombinase system is the FLP recombinase system of S. cerevisiae (O'Gorman et al. Science 251:1351–1355 (1991). If a cre/oxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. Nature 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the variant peptides described herein are useful to conduct the assays described herein in an in vivo context. Accordingly, the various physiological factors that are present in vivo and that could effect ligand binding, variant protein activation, and signal transduction, may not be evident from in vitro cell-free or cell-based assays. Accordingly, it is useful to provide non-human transgenic animals to assay in vivo variant protein function, including ligand interaction, and the effect of chimeric variant protein. It is also possible to assess the effect of null mutations, that is mutations that substantially or completely eliminate one or more variant protein functions.

Computer Related Embodiments

The SNPs provided in the present invention may be "provided" in a variety of mediums to facilitate use thereof. As used herein, "provided" refers to a manufacture, other than an isolated nucleic acid molecule, that contains a SNP of the present invention. Such a manufacture provides the SNPs in a form that allows a skilled artisan to examine the manufacture using means not directly applicable to examining the SNPs or a subset thereof as they exists in nature or in purified form.

In one application of this embodiment, the SNPs of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable media can be used to create a manufacture comprising computer readable medium having recorded thereon a nucleotide sequence of the present invention. One such medium is provided with the present application, namely, the present application contains computer readable medium (CD-R) that has the sequence fragments containing SNPs provided/recorded thereon in ASCII text format in a Sequence Listing.

As used herein, "recorded" refers to a process for storing information on computer readable medium. A skilled artisan can readily adopt any of the presently known methods for recording information on computer readable medium to generate manufactures comprising the SNP information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as OB2Sybase, Oracle, or the like. A skilled artisan can readily adapt any number of data processor structuring formats (e.g. text file or database) in order to obtain computer readable medium having recorded thereon the SNP information of the present invention.

By providing the SNPs of the present invention in computer readable form, a skilled artisan can routinely access the SNP information for a variety of purposes. Computer software is publicly available which allows a skilled artisan to access sequence information provided in a computer readable medium. Examples of publicly available computer software include BLAST (Altschul et at, *J. Mol. Biol.* 215:403–410 (1990)) and BLAZE (Brutlag et at, *Comp. Chem.* 17:203–207 (1993)) search algorithms.

The present invention further provides systems, particularly computer-based systems, which contain the SNP information described herein. Such systems may be designed to store and/or analyze information on a large number of SNP positions, or information on SNP genotypes from a large number of individuals. The SNP information of the present invention represents a valuable information source. The SNP information of the present invention stored/analyzed in a computer-based system may be used for such computer-intensive applications as determining SNP allele frequencies in a population, for mapping disease genes, for genotype-phenotype association studies, for correlating SNP haplotypes with response to particular drugs, or for various other bioinformatic, pharmacogenomic, or forensic applications.

As used herein, "a computer-based system" refers to the hardware means, software means, and data storage means used to analyze the SNP information of the present invention. The minimum hardware means of the computer-based systems of the present invention comprises a central processing unit (CPU), input means, output means, and data storage means. A skilled artisan can readily appreciate that any one of the currently available computer-based systems are suitable for use in the present invention. Such a system can be changed into a system of the present invention by utilizing the SNP information provided on the CD-R, or a subset thereof without any experimentation.

As stated above, the computer-based systems of the present invention comprise a data storage means having stored therein SNPs of the present invention and the necessary hardware means and software means for supporting and implementing a search means. As used herein, "data storage means" refers to memory which can store SNP information of the present invention, or a memory access means which can access manufactures having recorded thereon the SNP information of the present invention.

As used herein, "search means" refers to one or more programs that are implemented on the computer-based system to score SNPs in a target sequence based on the SNP information stored within the data storage means. Search means are used to determine which nucleotide is present at a particular SNP position in the target sequence.

As used herein, a "target sequence" can be any DNA sequence containing the SNP position(s) to be scored.

As used herein, "a target structural motif," or "target motif," refers to any rationally selected sequence or combination of sequences containing the SNP position in which the sequence(s) is chosen based on a three-dimensional configuration which is formed upon the folding of the target motif. There are a variety of target motifs known in the art. Protein target motifs include, but are not limited to, enzymatic active sites and signal sequences. Nucleic acid target motifs include, but are not limited to, promoter sequences, hairpin structures, and inducible expression elements (protein binding sequences).

A variety of structural formats for the input and output means can be used to input and output the information in the computer-based systems of the present invention. A preferred format for an output means is presence or absence of specified nucleotides at particular polymorphic positions. Such presentation can provide a rapid scoring system for many SNPs simultaneously.

One application of this embodiment is provided in FIG. 1. FIG. 1 provides a block diagram of a computer system 102 that can be used to implement the present invention. The computer system 102 includes a processor 106 connected to a bus 104. Also connected to the bus 104 are a main memory 108 (preferably implemented as random access memory, RAM) and a variety of secondary storage devices 110, such as a hard drive 112 and a removable medium storage device 114. The removable medium storage device 114 may represent, for example, a floppy disk drive, a CD-ROM drive, a magnetic tape drive, etc. A removable storage medium 116 (such as a floppy disk, a compact disk, a magnetic tape, etc.) containing control logic and/or data recorded therein may be inserted into the removable medium storage device 114. The computer system 102 includes appropriate software for reading the control logic and/or the data from the removable storage medium 116 once inserted in the removable medium storage device 114.

The SNP information of the present invention may be stored in a well-known manner in the main memory 108, any of the secondary storage devices 110, and/or a removable storage medium 116. Software for accessing and processing the SNP information (such as SNP scoring tools, search tools, comparing tools, etc.) preferably resides in main memory 108 during execution.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

SEQUENCE LISTING

The patent contains a lengthy "Sequence Listing" section. A copy of the "Sequence Listing" is available in electronic form from the USPTO web site (http://seqdata.uspto.gov/sequence.html?DocID=6900016B1). An electronic copy of the "Sequence Listing" will also be available from the USPTO upon request and payment of the fee set forth in 37 CFR 1.19(b)(3).

What is claimed is:

1. A detection reagent selected firm the group consisting of:
   (a) a detection reagent comprising at least about 15 contiguous nucleotides of SEQ ID NO:1574, wherein the at least about 15 contiguous nucleotides include position 301 of SEQ ID NO:1574, and wherein position 301 of SEQ ID NO:1574 is 'G';
   (b) a detection reagent comprising at least about 15 contiguous nucleotides of SEQ ID NO:1574, wherein the at least about 15 contiguous nucleotides include position 301 of SEQ ID NO:1574, and wherein position 301 of SEQ ID NO:1574 is 'T'; and
   (c) a detection reagent which is entirely complementary to the detection reagent of (a) or (b).

2. An isolated polynucleotide selected from the group consisting of:
   (a) an isolated polynucleotide consisting of a segment of SEQ ID NO:1574, wherein the segment comprises at least about 12 contiguous nucleotides of SEQ ID NO:1574, and wherein the at least about 12 contiguous nucleotides include position 301 of SEQ ID NO:1574, and wherein position 301 of SEQ ID NO:1574 is 'G';
   (b) an isolated polynucleotide consisting of a sent of SEQ ID NO:1574, wherein the segment comprises at least about 12 contiguous nucleotides of SEQ ID NO:1574, and wherein the at least about 12 contiguous nucleotides include position 301 of SEQ ID NO:1574, and wherein position 301 of SEQ ID NO:1574 is 'T'; and
   (c) an isolated polynucleotide which is entirely complementary to the isolated polynucleotide of (a) or (b).

3. A detection reagent selected from the group consisting of:
   (a) a detection reagent comprising at least about 20 contiguous nucleotides of SEQ ID NO:1574, wherein the at least about 20 contiguous nucleotides include position 301 of SEQ ID NO:1574, and wherein position 301 of SEQ ID NO:1574 is 'G';
   (b) a detection reagent comprising at least about 20 contiguous nucleotides of SEQ ID NO:1574, wherein the at least about 20 contiguous nucleotides include position 301 of SEQ ID NO:1574, and wherein position 301 of SEQ ID NO:1574 is 'T'; and
   (c) a detection reagent which is entirely complementary to the detection reagent of (a) or (b).

4. An isolated polynucleotide consisting of a nucleotide sequence selected from the group consisting of:
   (a) the nucleotide sequence of SEQ ID NO:1574, wherein position 301 of SEQ ID NO:1574 is 'G';
   (b) the nucleotide sequence of SEQ ID NO:1574, wherein position 301 of SEQ ID NO:1574 is 'T'; and
   (c) a nucleotide sequence which is entirely complementary to the nucleotide sequence of (a) or (b).

5. An isolated polynucleotide consisting of a segment of a nucleotide sequence selected from the group consisting of SEQ ID NOS:602 and 764, wherein the segment comprises a nucleotide sequence selected from the group consisting of:
   (a) the nucleotide sequence of SEQ ID NO:1574, wherein position 301 of SEQ ID NO:1574 is 'G';
   (b) the nucleotide sequence of SEQ ID NO:1574, wherein position 301 of SEQ ID NO:1574 is 'T'; and
   (c) a nucleotide sequence which is entirely complementary to (a) or (b).

6. An amplified polynucleotide selected from the group consisting of:
   (a) an amplified polynucleotide comprising at least about 30 contiguous nucleotides of SEQ ID NO:1574, wherein the at least about 30 contiguous nucleotides include position 301 of SEQ ID NO:1574, and wherein position 301 of SEQ ID NO:1574 is 'G';
   (b) an amplified polynucleotide comprising at least about 30 contiguous nucleotides of SEQ ID NO:1574, wherein the at least about 30 contiguous nucleotides include position 301 of SEQ ID NO:1574, and wherein position 301 of SEQ ID NO:1574 is 'T'; and
   (c) an amplified polynucleotide which is entirely complementary to the amplified polynucleotide of (a) or (b).

7. An extension primer selected from the group consisting of:
   (a) an extension primer comprising at least about 12 contiguous nucleotides of SEQ ID NO:1574, wherein the at least about 12 contiguous nucleotides include position 301 of SEQ ID NO:1574, and wherein position 301 of SEQ ID NO:1574 is 'G', and wherein position 301 of SEQ ID NO:1574 is a ddNTP at the 3' end of the extension prier, and
   (b) an extension primer which is entirely complementary to the extension primer of (a).

8. An extension primer selected from the group consisting of:
   (a) an extension primer comprising at least about 20 contiguous nucleotides of SEQ ID NO:1574, wherein the at least about 20 contiguous nucleotides include position 301 of SEQ ID NO:1574, and wherein position 301 of SEQ ID NO:1574 is 'G', and wherein position 301 of SEQ ID NO:1574 is a ddNTP at the 3' end of the extension primer; and
   (b) an extension primer which is entirely complementary to the extension primer of (a).

9. An extension primer selected from the group consisting of:
   (a) an extension primer comprising at least about 12 contiguous nucleotides of SEQ ID NO:1574, wherein the at least about 12 contiguous nucleotides include position 301 of SEQ ID NO:1574, and wherein position 301 of SEQ ID NO:1574 is 'T', and wherein position 301 of SEQ ID NO:1574 is a ddNTP at the 3' end of the extension primer, and
   (b) an extension primer which is entirely complementary to the extension primer of (a).

10. An extension primer selected from the group consisting of:
    (a) an extension primer comprising at least about 20 contiguous nucleotides of SEQ ID NO:1574, wherein the at let about 20 contiguous nucleotides include position 301 of SEQ ID NO:574, and wherein position 301 of SEQ ID NO:1574 is 'T', and wherein position 301 of SEQ ID NO:1574 is a ddNTP at the 3' end of the extension primer; and
    (b) an extension primer which is entirely complementary to the extension primer of (a).

11. The extension primer of claim 6, wherein the ddNTP is delectably labeled.

12. The extension primer of claim 11, wherein the ddNTP is labeled with a mass tag.

13. The detection reagent of claim 1 wherein position 301 of SEQ ED NO:1574 is about at the center of the detection reagent.

14. The detection reagent of claim 1 wherein position 301 of SEQ ID NO:1574 is about at the 3' end of the detection reagent.

15. The detection reagent of claim 1 wherein the detection reagent is detectably labeled.

16. The detection reagent of claim 15, wherein the detection reagent is labeled with a reporter.

17. The detection reagent of claim 16, wherein the reporter is fluorescent.

18. The detection reagent of claim 16, wherein the detection reagent is further labeled with a quencher.

19. The detection reagent of claim 1, wherein the detection reagent is bound to a solid support.

20. The detection reagent of claim 19, wherein the solid support comprises a nucleic acid array.

* * * * *